United States Patent
Salituro et al.

(10) Patent No.: US 10,201,550 B2
(45) Date of Patent: Feb. 12, 2019

(54) OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Cambridge, MA (US); Gabriel Martinez Botella, Wayland, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/742,425

(22) PCT Filed: Jul. 6, 2016

(86) PCT No.: PCT/US2016/041168
§ 371 (c)(1),
(2) Date: Jan. 5, 2018

(87) PCT Pub. No.: WO2017/007836
PCT Pub. Date: Jan. 12, 2017

(65) Prior Publication Data
US 2018/0200267 A1 Jul. 19, 2018

Related U.S. Application Data

(60) Provisional application No. 62/189,048, filed on Jul. 6, 2015, provisional application No. 62/280,394, filed on Jan. 19, 2016.

(51) Int. Cl.
A61K 31/575 (2006.01)
C07J 9/00 (2006.01)
C07J 7/00 (2006.01)

(52) U.S. Cl.
CPC ............... *A61K 31/575* (2013.01); *C07J 9/00* (2013.01); *C07J 7/002* (2013.01); *C07J 9/005* (2013.01)

(58) Field of Classification Search
CPC .................................................. A61K 31/575
USPC ........................................................ 514/182
See application file for complete search history.

(56) References Cited

U.S. PATENT DOCUMENTS

| | | | |
|---|---|---|---|
| 2,594,323 | A | 4/1952 | Levin et al. |
| 3,079,385 | A | 2/1963 | Bertin et al. |
| 3,206,459 | A | 9/1965 | Cross |
| 4,071,625 | A | 1/1978 | Grunwell et al. |
| 5,888,996 | A | 3/1999 | Farb |
| 5,925,630 | A | 7/1999 | Upasani et al. |
| 8,247,436 | B2 | 8/2012 | Baettig et al. |
| 8,604,011 | B2 | 12/2013 | Mellon |
| 2006/0199790 | A1 | 9/2006 | Baulieu et al. |
| 2008/0193423 | A1 | 8/2008 | Brunton et al. |
| 2008/0269183 | A1 | 10/2008 | Mellon et al. |
| 2008/0319026 | A1 | 12/2008 | Gant et al. |
| 2010/0034781 | A1 | 2/2010 | Parhami et al. |
| 2012/0041016 | A1 | 2/2012 | Frincke |
| 2012/0115169 | A1 | 5/2012 | Mullenix et al. |
| 2013/0210792 | A1 | 8/2013 | Song et al. |
| 2014/0235600 | A1 | 8/2014 | Covey et al. |
| 2014/0335050 | A1 | 11/2014 | Haggerty et al. |
| 2015/0158903 | A1 | 6/2015 | Upasani et al. |
| 2015/0291654 | A1 | 10/2015 | Upasani et al. |
| 2016/0022701 | A1 | 1/2016 | Reddy et al. |
| 2016/0031930 | A1* | 2/2016 | Martinez Botella ....... C07J 9/00 514/182 |

FOREIGN PATENT DOCUMENTS

| | | |
|---|---|---|
| FR | 2850023 A1 | 7/2004 |
| JP | 8268917 A | 10/1996 |
| JP | 2005508368 A | 3/2005 |
| RU | 2194712 C2 | 12/2002 |
| WO | 9427608 A1 | 12/1994 |
| WO | 1995002409 A2 | 1/1995 |
| WO | 1995021617 A1 | 8/1995 |

(Continued)

OTHER PUBLICATIONS

Leaoni et al Chemistry and Physics of Lipids 2011, 164, 515-524 (Year: 2011).*
Olkkonen et al, Biomolecules, 2012, 2(1), 76-103 (Year: 2012).*
U.S. Appl. No. 14/775,401, filed Sep. 11, 2015, Kiran Reddy et al., Pending.
U.S. Appl. No. 15/319,504, filed Dec. 16, 2016, Boyd L. Harrison et al., Pending.
U.S. Appl. No. 16/028,790, filed Jul. 6, 2018, Boyd L. Harrison et al., Pending.
U.S. Appl. No. 14/343,603, filed Nov. 25, 2014, Ravindra B. Upasani., Pending.

(Continued)

*Primary Examiner* — Yevgeny Valenrod
(74) *Attorney, Agent, or Firm* — Goodwin Procter LLP

(57) ABSTRACT

Compounds are provided according to Formula (I): Formula (I) and pharmaceutically acceptable salts thereof, and pharmaceutical compositions thereof; wherein $R^1$, $R^2$, $R^3$, $R^6$, $R^7$, $R^8$, and n are as defined herein. Compounds of the present invention are contemplated useful for the prevention and treatment of a variety of conditions.

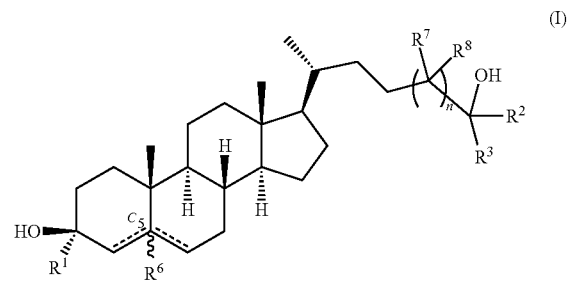

2 Claims, No Drawings

(56) References Cited

FOREIGN PATENT DOCUMENTS

| | | | |
|---|---|---|---|
| WO | 9612705 A1 | 5/1996 | |
| WO | 199905849 | 11/1999 | |
| WO | 2000068246 A1 | 11/2000 | |
| WO | 2001049703 A2 | 7/2001 | |
| WO | 0211708 A2 | 2/2002 | |
| WO | 02053577 A2 | 7/2002 | |
| WO | 2003039480 A2 | 5/2003 | |
| WO | 03049685 A2 | 6/2003 | |
| WO | 2004055201 A2 | 7/2004 | |
| WO | 2005079810 A1 | 9/2005 | |
| WO | 2009090063 A1 | 7/2009 | |
| WO | 2010075282 A1 | 7/2010 | |
| WO | 2011067501 A1 | 6/2011 | |
| WO | 2012142039 A1 | 10/2012 | |
| WO | 2013036835 A1 | 3/2013 | |
| WO | 2013056181 A1 | 4/2013 | |
| WO | 2013163455 A2 | 10/2013 | |
| WO | 2014115167 A2 | 7/2014 | |
| WO | 2014160480 A1 | 10/2014 | |
| WO | WO-2014160441 A1 * | 10/2014 | ............... C07J 9/00 |
| WO | 2015195967 A1 | 12/2015 | |
| WO | 2016007762 A1 | 1/2016 | |
| WO | 2017007836 A1 | 1/2017 | |
| WO | 2017037465 A1 | 3/2017 | |

OTHER PUBLICATIONS

U.S. Appl. No. 15/917,263, filed Mar. 9, 2018, Gabriel Martinez Botella et al., Pending.
U.S. Appl. No. 15/517,886, filed Apr. 7, 2017, Michael C. Quirk et al., Pending.
U.S. Appl. No. 15/742,422, filed Jan. 5, 2018, Francesco G. Salituro et al., Pending.
U.S. Appl. No. 15/742,424, filed Jan. 5, 2018, Francesco G. Salituro et al., Pending.
Pubchem, CID 71508953, pp. 1-13.
Reddy, "Pharmacology of endogenous neuroactive steroids, Crit Rev Neurobiol", 2003;15(3-4) pp. 197-234.
Schmidt et al., "Inhibitory effect of oxygenated cholestan-3b-ol derivatives on the growth of Mycobacterium tuberculosis", Bioorganic & Medicinal Chemistry Letters, vol. 23, No. 22, (2013), pp. 6111-6113.
Stamp et al., "Plasma Levels and Therapeutic Effect of 25-Hydroxycholecalciferol in Epileptic Patients taking Anticonvulsant Drugs", British Medical Journal, vol. 4, 1972, pp. 9-12.
Stastna et al., "Synthesis of C3, C5, and C7 pregnane derivatives and their effect on NMDA receptor responses in aultured rat hippocampal neurons", Steroids, Elsevier Science Publishers, vol. 74, No. 2, (2008), pp. 256-263.
Steinrauf et al., "Synthesis and Evaluation of Sulfur-Containing Steroids Against Methylmercuric Chloride Toxicity", Journal of Pharmaceutical Sciences, vol. 67, No. 12, pp. 1739-1743, (1978).
Takano et al., "Simple Synthesis of 3b, 24-Dihydroxychol-5-EN-7-ONE by Oxidative Cleavage of the Side Chain of Cholesterol", Chemistry Letters, vol. 14, No. 8, (1985), pp. 1265-1266.
Tierney et al., "Abnormalities of Cholesterol Metabolism in Autism Spectrum Disorders", Am J Med Genet B Neuropsychiatr Genet. vol. 1418, No. 6, (2006), pp. 666-668.
Vincent Chen et al., "The chemical biology of clinicall tolerated NMDA receptor antagonists", Journal of Neurochemistry, (2006), pp. 1611-1626.
Wolozin et al., "The Cellular Biochemistry of Cholesterol and Statins: Insights into the Pathophysiology and Therapy of Alzheimer's Disease" vol. 10, No. 2, 2004, pp. 127-146.
Wong et al., An efficient and convenient transformation of a-haloketones to a-hydroxyketones using cesium formate. Journal of Organometallic Chemistry 2006, 694, 3452-3455.
Xilouri et al., "Neuroprotective effects of steroid analogues on P19-N neurons", Neurochemistry International, (2007), vol. 50, No. 4, pp. 660-670.

Yang et al., "New cytotoxic oxygenated sterols from marine bryozoan Bugula neritina", Natural Product Research, vol. 25, No. 16, (2011), pp. 1505-1511.
Yoon-Seok et al., "Neuroprotective Effects of Ginsenoside Rg3 against 24-0H-cholesterol-induced Cytotoxicity in Cortical Neurons", Journal of Ginseng Research, vol. 34, No. 3, pp. 246-253, (2010).
Zuliani et al., "Plasma 24S-hydroxycholesterol levels in elderly subjects with late onset Alzheimer's disease or vascular dementia: a case-control study" BMC Neurology, vol. 11, No. 121, pp. 1-8, (2011).
Cecil Textbook of Medicine, 20th edition (1996), vol. 2, pp. 1992-1996.
Cecil Textbook of Medicine, 20th edition (1996), vol. 2, pp. 2050-2057.
Citraro et al., "Effects of some neurosteroids injected into some brain areas of WAG/Rij rats, an animal model of generalized absence epilepsy", Neuropharmacology, (2006), vol. 50, No. 8, pp. 1059-1071.
Collingridge, "The NMDA receptor as a target for cognitive enhancement", Neuropharmacology. (2013), pp. 13-26, abstract.
Connick et al., "Program No. 613 1/B86", 2009 Neuroscience Meeting Planner. Chicago, IL: Society for Neuroscience, (2009).
Corman et al., "Structure-Activity Relationships for Side Chain Oxysterol Agonists of the Hedgehog Signaling Pathway", ACS Medicinal Chemistry Letters, Aug. 28, 2012, 3, 828-833.
Cross et al., "Steroids CCLXXIN 1. Biologically-Active Labile Ethers IV2. The Synthesis of 22-Oxa-25-Azacholesterol and Related Compounds", Steroids, Elsevier Science Publishers, vol. 5, No. 5, pp. 585-598, (1965).
Database Chemical Abstracts Service, Xiangdong et al. "Highly stereoselective synthesis of 24R,25- and 24S, 25-dihydroxysteroid", Database acession No. 2001:174431, (2000).
Dayal et al., "Stereospecific synthesis of 3b-hydroxylated bile alcohols", Journal of Lipid Research, vol. 25, No. 6, (1984), pp. 646-650.
Extended European Search Report for Application No. 15809462.3 dated Nov. 29, 2017.
Extended European Search Report for European Application No. 14775126.7.
Extended European Search Report for European Application No. 15849514.3 dated May 23, 2018.
Extended European Search Report for PCTUS2014/026784 dated Aug. 17, 2016.
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.
Festa et al., "Exploitation of Cholane Scaffold for the Discovery of Potent and Selective Farnesoid X Receptor (FXR) and G-Protein Coupled Bile Acid Receptor 1 (GP-BAR1) Ligands", Journal of Medicinal Chemistry, vol. 57, No. 20, (2014), pp. 8477-8495.
Foster et al., "Effect of steroids on 13-adrenoceptor-mediated relaxation of pig bronchus", Br. J. Pharmac. vol. 78, 1983, pp. 441-445.
Gunatilaka et al., "Bioactive Ergost-5-ENE-3b, 7a-DIOL Derivatives from Pseudobersama Mossambicensis", Journal of Natural Products, vol. 55, No. 11, (1992), pp. 1648-1654.
Hoffmeister et al., "Zur Chemie des Ecdysons, III: Vergleichende spektrometrische Untersuchungen an a.b-ungesättigten Steroidketonen", Chemische Berichte, (1965), vol. 98, pp. 2361-2375.
International Search Report and Written Opinion for corresponding International Application No. PCT/US14/26633 dated Jul. 14, 2014.
International Search Report and Written Opinion for corresponding International Application No. PCT/US15/36510 dated Sep. 15, 2015.
International Search Report and Written Opinion for corresponding International Application No. PCT/US17/25535 dated Jul. 3, 2017.
International Search Report and Written Opinion for corresponding International Application No. PCT/US17/31374 dated Jul. 17, 2017.
International Search Report and Written Opinion for corresponding International Application No. PCT/US2012/054261 dated Nov. 28, 2012.

(56) References Cited

OTHER PUBLICATIONS

International Search Report and Written Opinion for corresponding International Application No. PCT/US2014/026784 dated Jul. 8, 2014.
International Search Report and Written Opinion for corresponding International Application No. PCT/US2015/054551 dated Jan. 8, 2016.
International Search Report and Written Opinion for corresponding International Application No. PCT/US2016/041160 dated Oct. 28, 2016.
International Search Report and Written Opinion for corresponding International Application No. PCT/US2016/041168 dated Sep. 15, 2016.
International Search Report and Written Opinion for corresponding International Application No. PCT/US2016/041175 dated Sep. 16, 2016.
International Search Report and Written Opinion for corresponding International Application No. PCT/US2017/041199 dated Aug. 29, 2017.
International Search Report and Written Opinion for corresponding International Application No. PCT/US2017/054657 dated Nov. 21, 2017.
International Search Report and Written Opinion for corresponding International Application No. PCT/US2017/057276 dated Nov. 12, 2017.
International Search Report and Written Opinion for corresponding International Application No. PCT/US2017/057277 dated Feb. 20, 2018.
Karaki et al., "Structure-activity relationship studies of Niemann-Pick type C1-like 1 (NPC1L1) ligands identified by screening assay monitoring pharmacological chaperone effect", Bioorganic & Medicinal Chemistry, vol. 21, Issue 17, (2013), pp. 5297-5309.
Khripach et al., "Synthesis of (24S)-Hydroxy-and (24S)-24,25-Epoxycholesterol Analogues, Potential Agonists of Nuclear LXR Receptors", Russian Journal of Bioorganic Chemistry, Kluwer Academic Publishers-Plenum Publishers, NE, vol. 32, No. 6, pp. 586-594, (2006).
Kurosawa et al., "Synthesis of 19-Hydroxylated Bile Acids and Identification of 3a,7a,12a,19-Tetrahydroxy-5b-cholan-24oic Acid in Human Neonatal Urine" 1995, Chem. Pharm. Bull, vol. 43, No. 9, pp. 1551-1557.
Lettré, et al., "Mehrwertige Alkohole aus Sterinen und Sterinderivaten, VI Steroide mit Strukturmerkmalen des Ecdysons und der Elatericine", Justus Liebigs Annalen der Chemie, (1972), vol. 758, pp. 89-110. English Abstract.
Li et al., "Synthesis of 7a-hydroxy derivatives of regulatory oxysterols", Steroids, vol. 65, No. 9, (2000), pp. 529-535.
Mouriño et al., "Studies on vitamin D (calciferol) and its analogs. 15. 24-Nor-1a.,25-dihydroxyvitamin D3 and 24-nor-25-hydroxy-5,6-trans-vitamin D3", J. Med. Chem., (1978), vol. 21, No. 10, pp. 1025-1029.
Nagano et al., "Chemistry and Biochemistry of Chinese Drugs. Part II. Hydroxylated Sterols, Cytotoxic Towards Cancerous Cells: Synthesis and Testing", Journal of Chemical Research, vol. 9, pp. 218 (1977).
Park-Chung et al., "Distinct sites for inverse modulation of N-methyl-D-aspartate receptors by sulfated steroids", Molecular Pharmacology, vol. 52, No. 6, (1997), pp. 1113-1123.
Partial International Search Report and Provisional Opinion for corresponding Internation Application No. PCT/US2017/057277 dated Dec. 20, 2017.
Partial Supplementary European Search Report for European Application No. 14775126.7 dated Sep. 14, 2016.
Paul et al., "The Major Brain Cholesterol Metabolite 24 (S)-Hydroxycholesterol is a Potent Allosteric Modulator of N-Methyl-D-Aspartate Receptors", Journal of Neuroscience, vol. 33, No. 44, pp. 17290-17300, (2013).
Pubchem, 25-Hydroxycholesterol, CID 65094, pp. 1-6.
Pubchem, CID 132021, pp. 1-15.
Pubchem, CID 54083335, pp. 1-3.
Pubchem, CID 54160779, pp. 1-3.
Pubchem, CID 58455549, pp. 1-4.
Pubchem, CID 66966798, pp. 1-3.
Pubchem, CID 70604305, pp. 1-3.

\* cited by examiner

OXYSTEROLS AND METHODS OF USE THEREOF

RELATED APPLICATIONS

The present application is a U.S. National Phase Application under 35 U.S.C. § 371 of International Application No. PCT/US2016/041168, filed Jul. 6, 2016, which claims the benefit of and priority to U.S. Provisional Application No. 62/189,048 filed Jul. 6, 2015, and 62/280,394 filed Jan. 19, 2016, the contents of each of which are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are derived from cholesterol and have been shown to potently and selectively modulate NMDA receptor function. New and improved oxysterols are needed that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols. Further provided are pharmaceutical compositions comprising the compounds of the present invention, and methods of their use and treatment.

In one aspect, provided herein are compounds according to Formula (I):

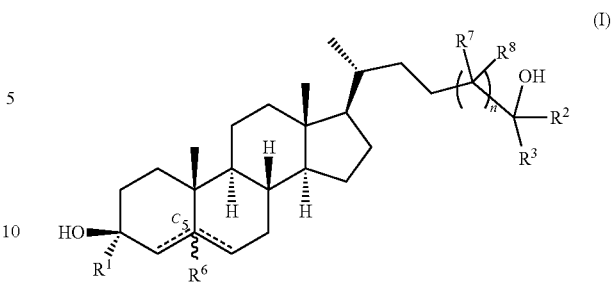

or a pharmaceutically acceptable salt thereof, wherein: $R^1$ is $C_{1-6}$ alkyl; each of $R^2$ and $R^3$ is independently hydrogen, $C_{1-6}$ alkyl, or carbocyclyl; or $R^2$ and $R^3$, together with the carbon atom to which they are attached, form a 3-8 membered ring; $R^6$ is absent or hydrogen; each of $R^7$ and $R^8$ is independently hydrogen, halogen, $C_{1-6}$ alkyl, or carbocyclyl; or each of $R^7$ and $R^8$, together with the carbon atom to which they are attached, form a 3-8 membered ring; or $R^2$ and $R^7$, together with the carbon atoms to which they are attached, form a 3-8 membered ring; n is 1, 2, or 3; and ==== represents a single or double bond, wherein when one ==== is a double bond, the other ==== is a single bond; and when one of the ==== is a double bond, $R^6$ is absent.

In some embodiments, $R^1$ is substituted $C_{1-6}$ alkyl. In some embodiments, $R^1$ is unsubstituted $C_{1-6}$ alkyl. In some embodiments, $R^1$ is methyl (e.g., —CHF$_2$, —CH$_3$, —CF$_3$, —CH$_2$OCH$_3$, or —CH$_2$OCH$_2$CH$_3$), ethyl, or isopropyl. In some embodiments, $R^1$ is —CH$_3$. In some embodiments, $R^1$ is ethyl.

In some embodiments, each of $R^2$ and $R^3$ is independently hydrogen, $C_{1-6}$ alkyl, or carbocyclyl, or wherein $R^2$ and $R^3$ are taken together with the carbon atom to which they are attached form a 3-8 membered ring. In some embodiments, the 3-8 membered ring is a carbocyclyl ring (e.g., cyclopropyl). In some embodiments, each of $R^2$ and $R^3$ is independently hydrogen, $C_{1-6}$ alkyl, or carbocyclyl. In some embodiments, each of $R^2$ and $R^3$ is independently hydrogen, methyl (e.g., —CH$_3$, —CF$_3$), ethyl (e.g., —CH$_2$CH$_3$, CH$_2$CF$_3$), propyl, isopropyl, cyclopropyl, or butyl.

In some embodiments, $R^2$ substituted $C_{1-6}$ alkyl. In some embodiments, $R^2$ unsubstituted $C_{1-6}$ alkyl.

In some embodiments, $R^2$ is hydrogen, methyl (e.g., —CH$_3$, —CF$_3$), ethyl, or isopropyl-.

In some embodiments, $R^3$ substituted $C_{1-6}$ alkyl. In some embodiments, $R^3$ unsubstituted $C_{1-6}$ alkyl.

In some embodiments, $R^3$ is methyl (e.g., —CH$_3$, —CF$_3$), ethyl (e.g., —CH$_2$CH$_3$, CH$_2$CF$_3$), propyl, isopropyl, cyclopropyl, or butyl.

In some embodiments, $R^2$ and $R^3$ are hydrogen. In some embodiments, $R^2$ is hydrogen and $R^3$ is $C_{1-6}$ alkyl (e.g., methyl (e.g., —CH$_3$, —CF$_3$), ethyl, isopropyl). In some embodiments, $R^2$ is $C_{1-6}$ alkyl and $R^3$ is $C_{1-6}$ alkyl. In some embodiments, $R^2$ and $R^3$ are —CH$_3$. In some embodiments, $R^2$ is —CH$_3$ and $R^3$ is —CF$_3$. In some embodiments, $R^2$ is —CH$_3$ and $R^3$ is ethyl. In some embodiments, $R^2$ is —CH$_3$ and $R^3$ is isopropyl.

In some embodiments, each of ==== is a single bond.

In some embodiments, $R^6$ is hydrogen. In some embodiments, $R^6$ is in the alpha position. In some embodiments, $R^6$ is in the beta position.

In some embodiments, $R^6$ is absent.

In some embodiments, $R^7$ and $R^8$ are hydrogen.

In some embodiments, n is 1. In some embodiments, n is 1 and $R^7$ and $R^8$ are hydrogen.

In some embodiments, n is 2. In some embodiments, n is 2 and each of $R^7$ and $R^8$ is independently hydrogen, halogen, $C_{1-6}$ alkyl, or carbocyclyl.

In some embodiments, the compound Formula (I) is a compound of Formula (II):

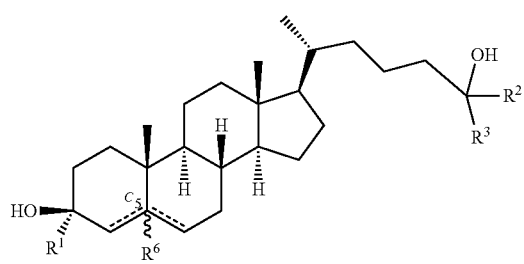

(II)

or a pharmaceutically acceptable salt thereof.

In some embodiments, the compound of Formula (II) is a compound of Formula (II-A) or Formula (II-B):

(II-A)

(II-B)

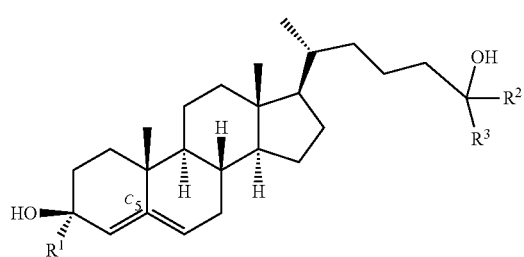

or a pharmaceutically acceptable salt thereof.

In some embodiments, the compound of Formula (I) is a compound of Formula (II-B-i) or Formula (II-B-ii):

(II-B-i)

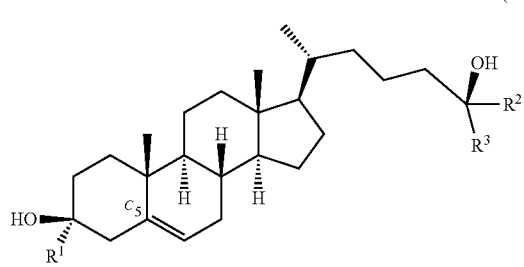

-continued (II-B-ii)

or a pharmaceutically acceptable salt thereof.

In some embodiments, the compound of Formula (I) is a compound of Formula (II-B-iii):

(II-B-iii)

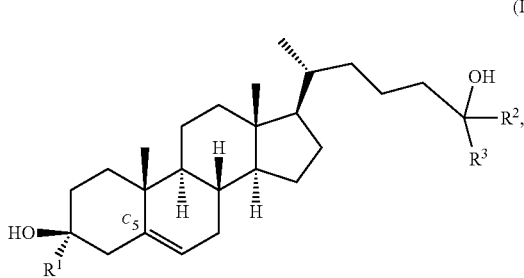

or a pharmaceutically acceptable salt thereof.

In some embodiments, the compound of Formula (I) is a compound of Formula (III):

(III)

or a pharmaceutically acceptable salt thereof.

In some embodiments, the compound of Formula (III) is a compound of Formula (III-A) or Formula (III-B):

(III-A)

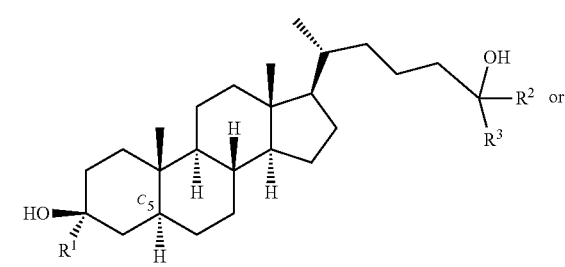

(III-B)

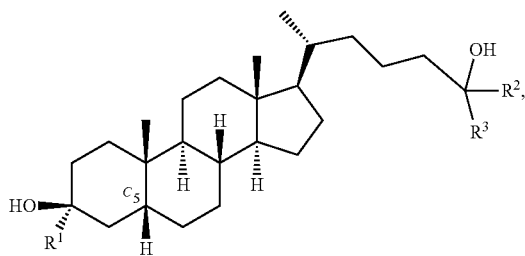

or a pharmaceutically acceptable salt thereof.

In some embodiments, the compound of Formula (III-B) is a compound of Formula (III-C) or Formula (III-D):

(III-C)

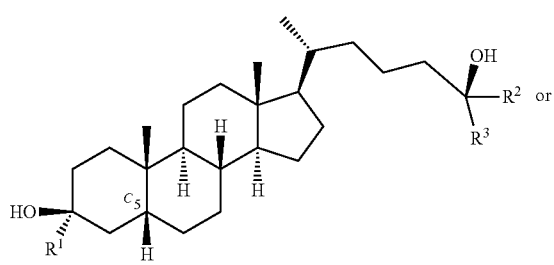

or (III-D)

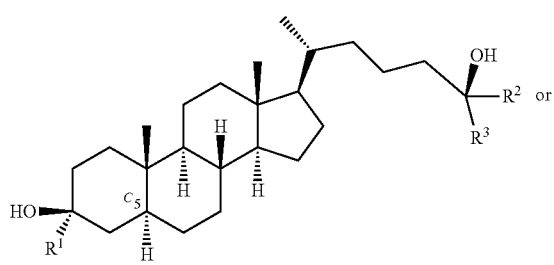

or a pharmaceutically acceptable salt thereof.

In some embodiments, the compound of Formula (III-A) is a compound of Formula (III-E) or Formula (III-F):

(III-E)

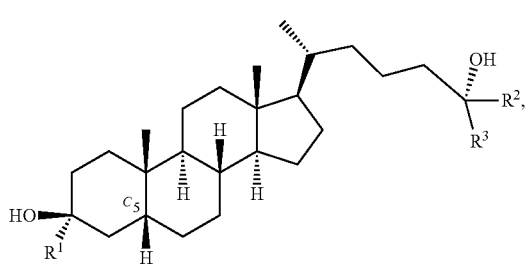

(III-F)

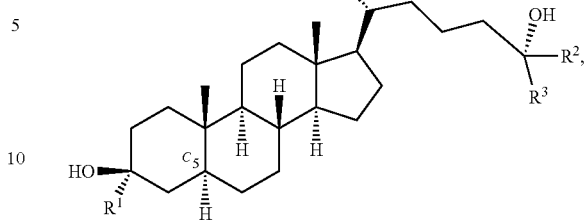

or a pharmaceutically acceptable salt thereof.

In some embodiments, the compound of Formula (III) is a compound of Formula (III-A-i-a) or Formula (III-B-i-a):

(III-A-i-a)

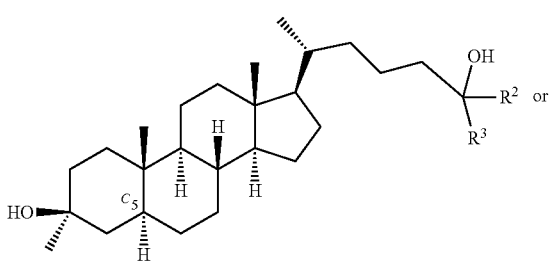

or (III-B-i-a)

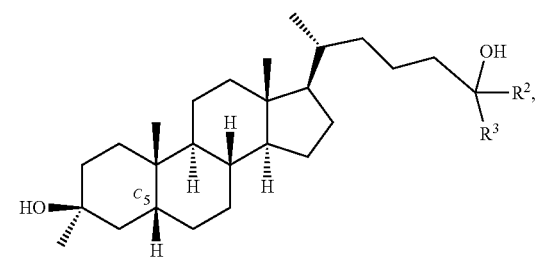

or a pharmaceutically acceptable salt thereof.

In some embodiments, $R^1$ is methyl (e.g., —CHF$_2$, —CF$_3$, —CH$_2$OCH$_3$, or —CH$_2$OCH$_2$CH$_3$), ethyl, or isopropyl.

In some embodiments, each of $R^2$ and $R^3$ is independently hydrogen, $C_{1-6}$ alkyl, or carbocyclyl, or wherein $R^2$ and $R^3$ are taken together with the carbon atom to which they are attached form a 3-8 membered ring.

In some embodiments, each of $R^2$ and $R^3$ is independently hydrogen, $C_{1-6}$ alkyl, or carbocyclyl.

In some embodiments, each of $R^2$ and $R^3$ is independently hydrogen, methyl (e.g., —CH$_3$, —CF$_3$), ethyl (e.g., —CH$_2$CH$_3$, —CH$_2$CF$_3$), propyl, isopropyl, cyclopropyl, or butyl.

In some embodiments, $R^2$ is hydrogen, methyl (e.g., —CH$_3$, —CF$_3$), or ethyl.

In some embodiments, $R^3$ is methyl (e.g., —CH$_3$, —CF$_3$), ethyl (e.g., —CH$_2$CH$_3$, —CH$_2$CF$_3$), propyl, isopropyl, cyclopropyl, or butyl.

In some embodiments, the compound is selected from the group consisting of:

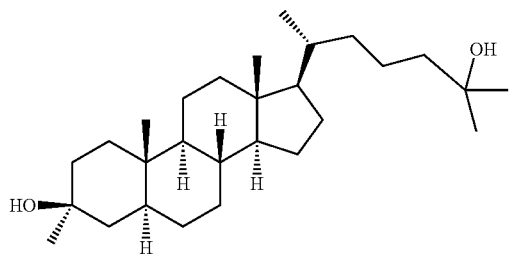 and

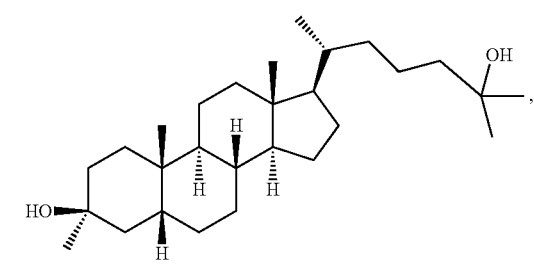, or a pharmaceutically acceptable salt thereof.

In some embodiments, the compound of Formula (I) is a compound of Formula (IV):

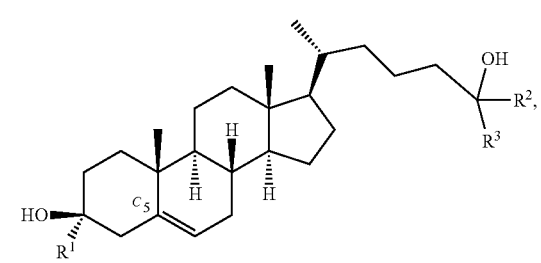

(IV)

or a pharmaceutically acceptable salt thereof.

In some embodiments, $R^1$ is methyl (e.g., —$CHF_2$, —$CF_3$, —$CH_2OCH_3$, or —$CH_2OCH_2CH_3$), ethyl, or isopropyl.

In some embodiments, each of $R^2$ and $R^3$ is independently hydrogen, $C_{1-6}$ alkyl, or carbocyclyl, or wherein $R^2$ and $R^3$ are taken together with the carbon atom to which they are attached form a 3-8 membered ring.

In some embodiments, each of $R^2$ and $R^3$ is independently hydrogen, $C_{1-6}$ alkyl, or carbocyclyl.

In some embodiments, each of $R^2$ and $R^3$ is independently hydrogen, methyl (e.g., —$CH_3$, —$CF_3$), ethyl (e.g., —$CH_2CH_3$, $CH_2CF_3$), propyl, isopropyl, cyclopropyl, or butyl.

In some embodiments, $R^2$ is hydrogen, methyl (e.g., —$CH_3$, —$CF_3$), or ethyl.

In some embodiments, $R^3$ is methyl (e.g., —$CH_3$, —$CF_3$), ethyl (e.g., —$CH_2CH_3$, —$CH_2CF_3$), propyl, isopropyl, cyclopropyl, butyl.

In some embodiments, the compound is:

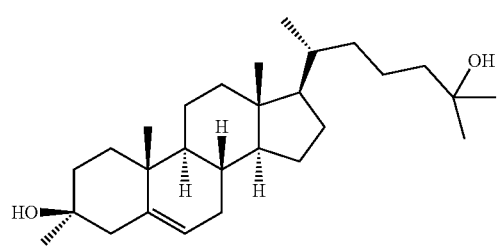, or a pharmaceutically acceptable salt thereof.

In some embodiments, the compound Formula (I) is a compound of Formula (V):

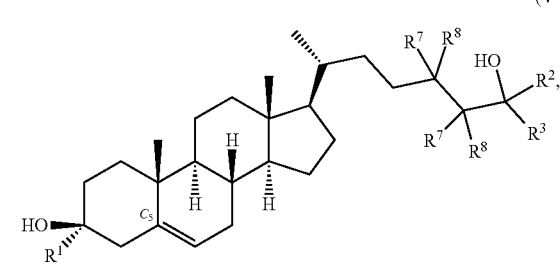

(V)

or a pharmaceutically acceptable salt thereof.

In some embodiments, the compound of Formula (I) is a compound of Formula (V-A):

(V-A)

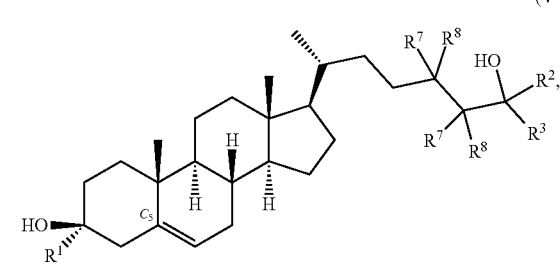

or a pharmaceutically acceptable salt thereof.

In some embodiments, the compound of Formula (I) is a compound of Formula (V-B):

(V-B)

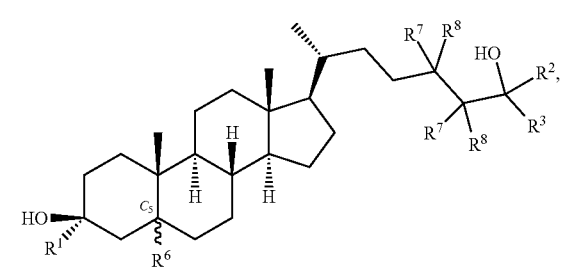

or a pharmaceutically acceptable salt thereof.

In some embodiments, the compound of Formula (III) is a compound of Formula (V-C) or Formula (V-D):

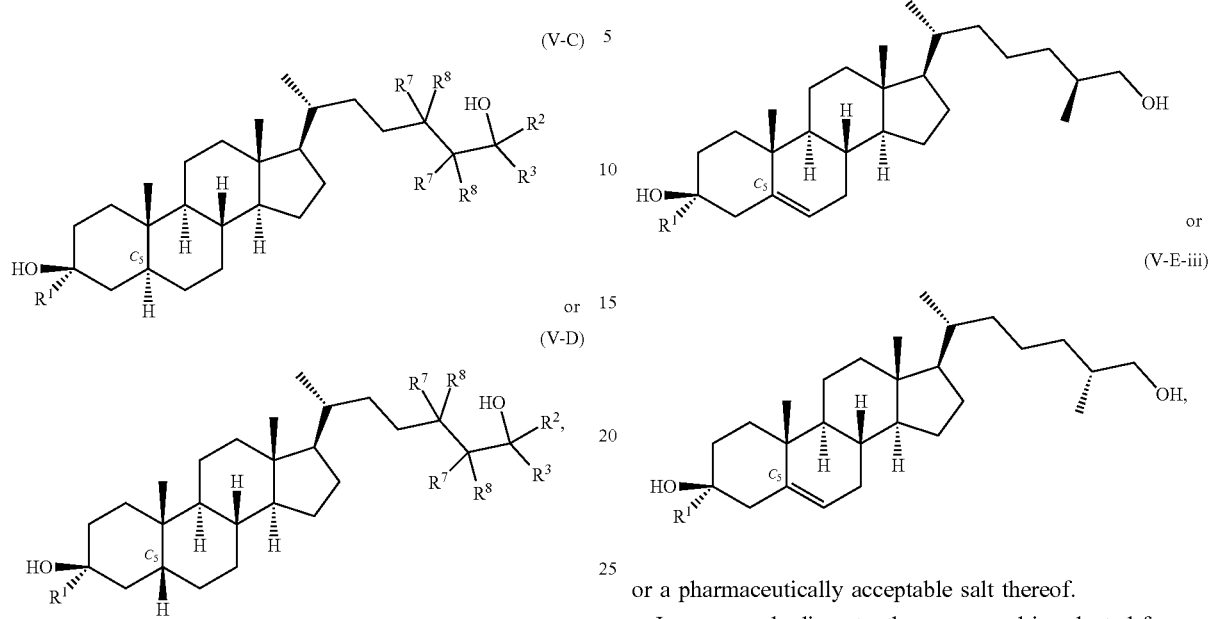

or a pharmaceutically acceptable salt thereof.

In some embodiments, the compound of Formula (I) is a compound of Formula (V-E):

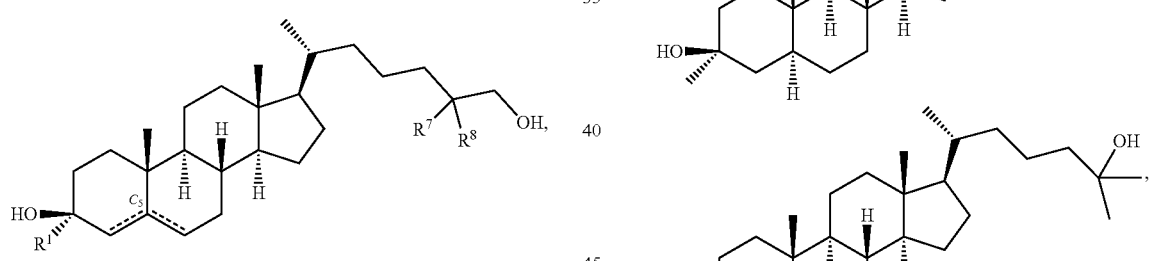

or a pharmaceutically acceptable salt thereof.

In some embodiments, the compound of Formula (V-E) is a compound of Formula (V-E-i):

(V-E-i)

or a pharmaceutically acceptable salt thereof.

In some embodiments, the compound of Formula (I) is a compound of Formula (V-E-ii) or (V-E-iii):

(V-E-ii)

or (V-E-iii)

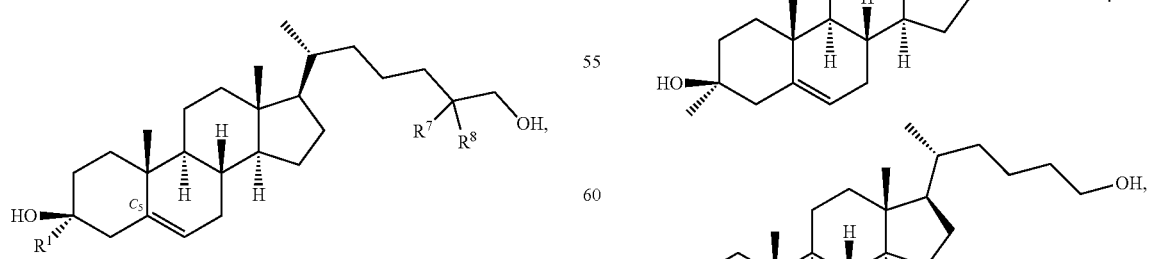

or a pharmaceutically acceptable salt thereof.

In some embodiments, the compound is selected from:

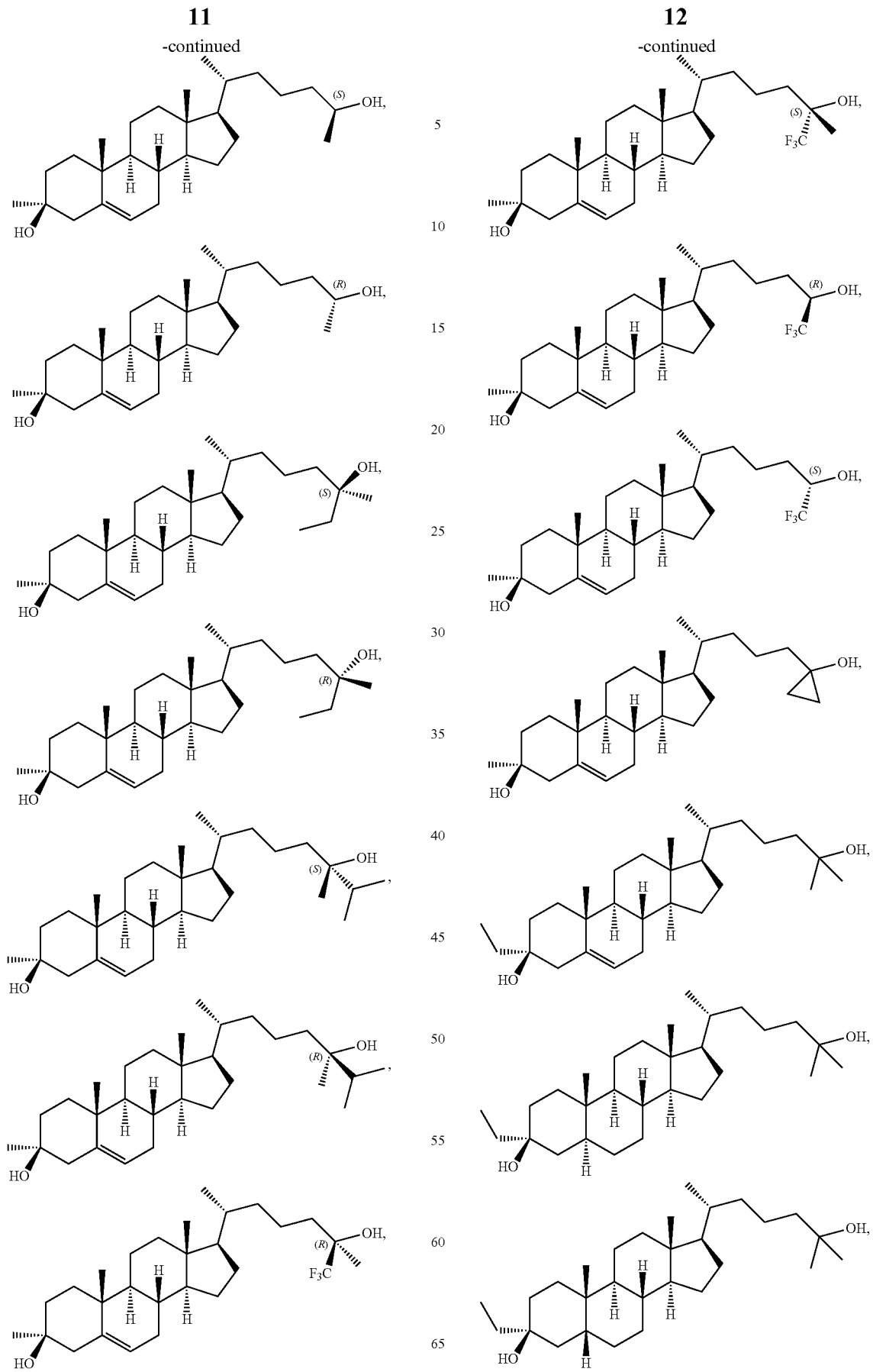

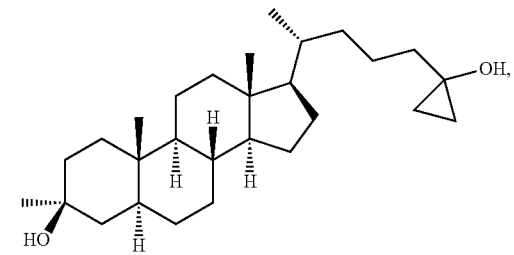
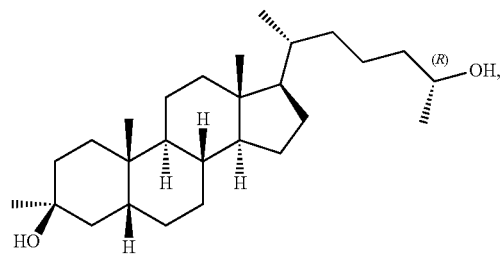
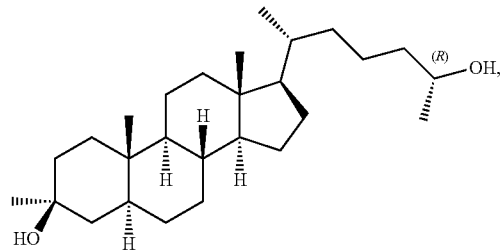
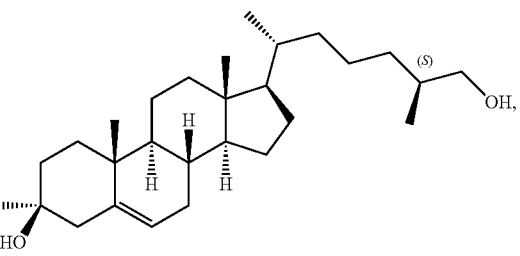
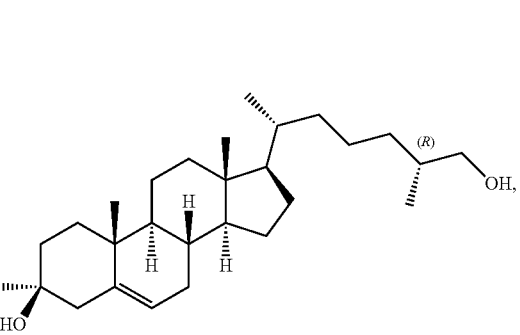
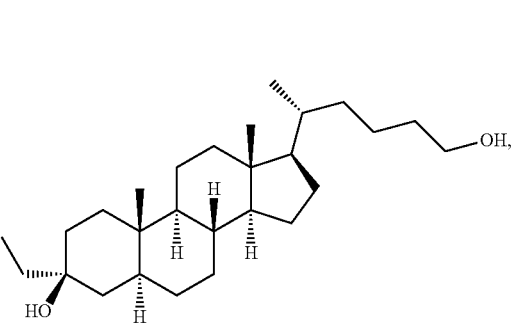
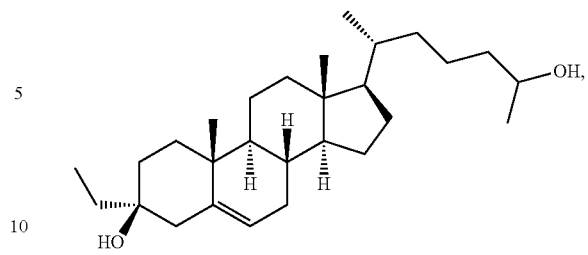
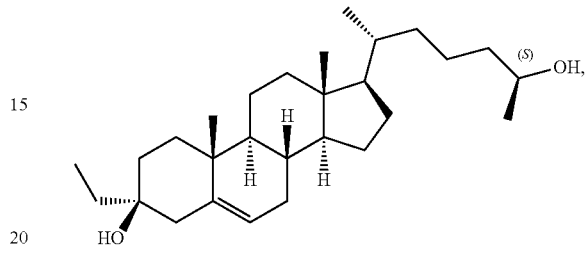
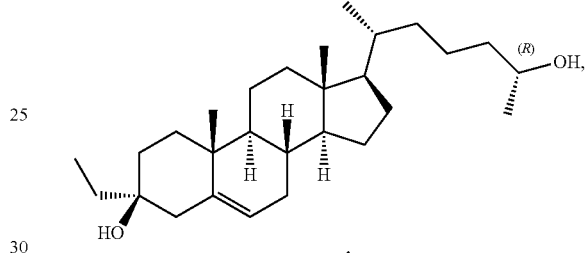
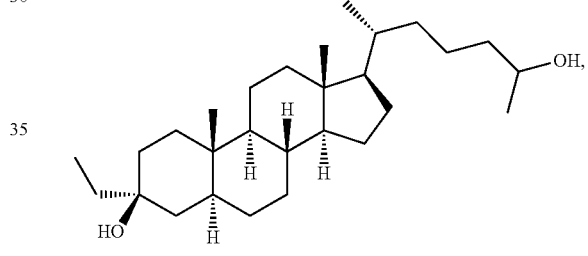
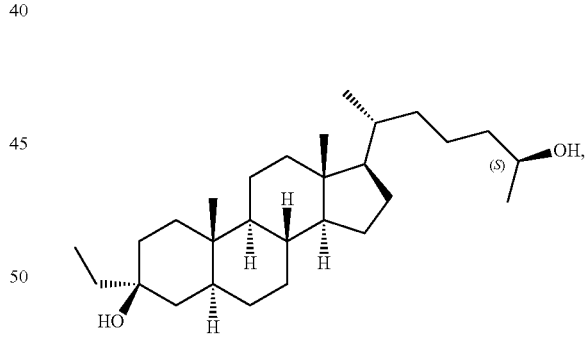
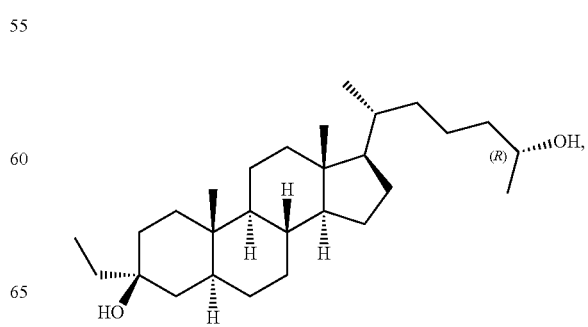

-continued

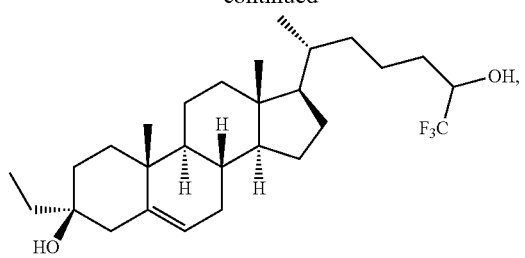
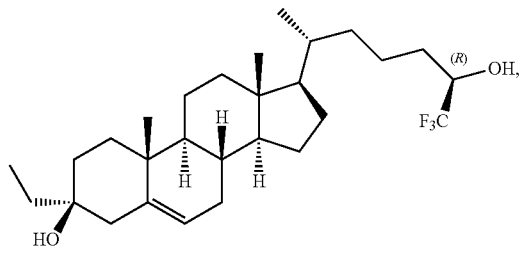
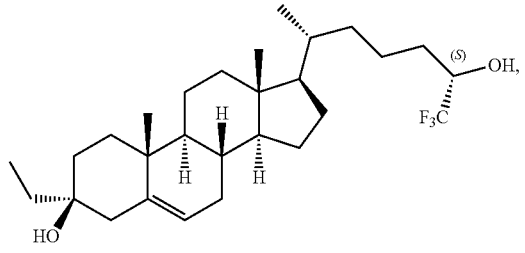
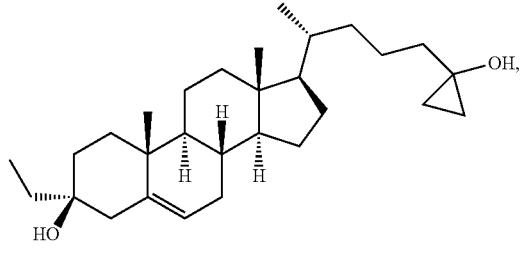
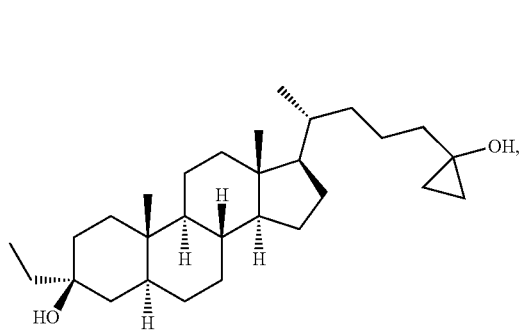
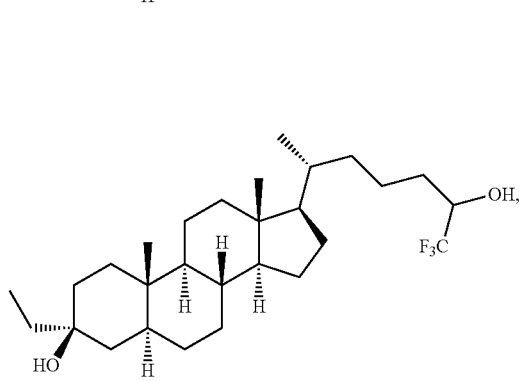

-continued

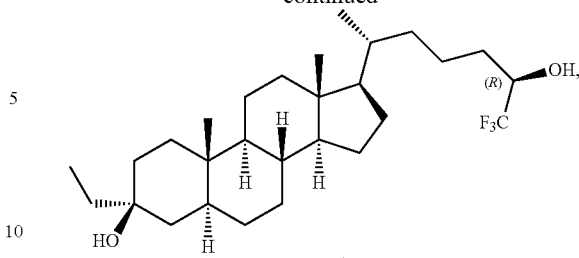
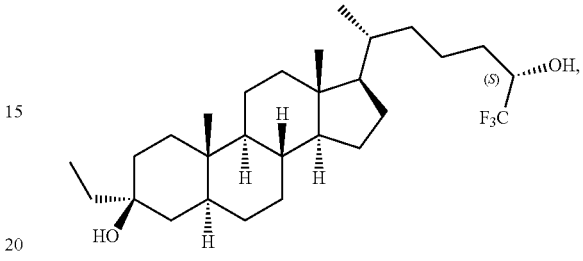

or a pharmaceutically acceptable salt thereof.

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is a metabolic disorder.

In some embodiments, the disorder is a gastrointestinal (GI) disorder e.g., constipation, irritable blowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis.

In some embodiments, the disorder is inflammatory bowel disease.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein, or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia (e.g., frontotemporal dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain; headaches, e.g., migraine headaches), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, and tinnitus.

In some embodiments, the disorder is Huntington's disease. In some embodiments, the disorder is Parkinson's disease. In some embodiments, the disorder is an inflammatory disease (e.g., lupus).

In some embodiments, the disorder is sterol synthesis disorder.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_5$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and for 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

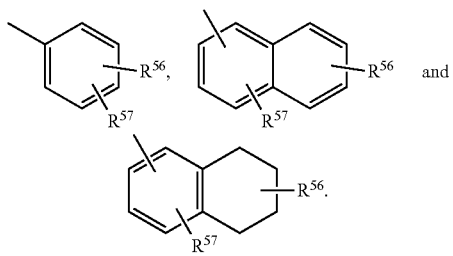

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

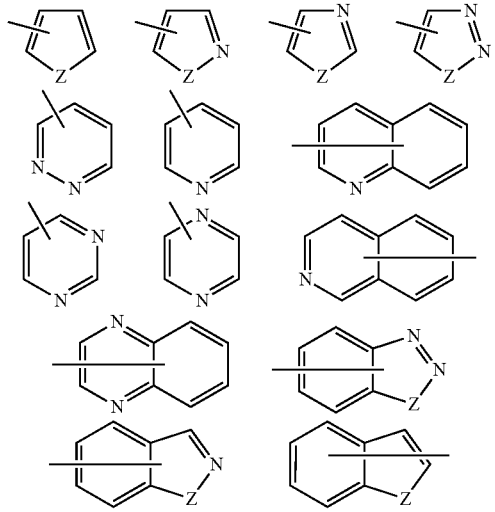

wherein each Z is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O-(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and –O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)

$(NR^{bb})_2$, $-NR^{bb}P(=O)(OR^{cc})_2$, $-NR^{bb}P(=O)(NR^{bb})_2$, $-P(R^{cc})_2$, $-P(R^{cc})_3$, $-OP(R^{cc})_2$, $-OP(R^{cc})_3$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3{}^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of e is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3{}^+X^-$, $-NH(C_{1-6}$ alkyl$)_2{}^+X^-$, $-NH_2(C_{1-6}$ alkyl$)^+X^-$, $-NH_3{}^+X^-$, $-N(OC_{1-6}$ alkyl$)(C_{1-6}$ alkyl$)$, $-N(OH)(C_{1-6}$ alkyl$)$, $-NH(OH)$, $-SH$, $-SC_{1-6}$ alkyl, $-SS(C_{1-6}$ alkyl$)$, $-C(=O)(C_{1-6}$ alkyl$)$, $-CO_2H$, $-CO_2(C_{1-6}$ alkyl$)$, $-OC(=O)(C_{1-6}$ alkyl$)$, $-OCO_2(C_{1-6}$ alkyl$)$, $-C(=O)NH_2$, $-C(=O)N(C_{1-6}$ alkyl$)_2$, $-OC(=O)NH(C_{1-6}$ alkyl$)$, $-NHC(=O)(C_{1-6}$ alkyl$)$, $-N(C_{1-6}$ alkyl$)C(=O)(C_{1-6}$ alkyl$)$, $-NHCO_2(C_{1-6}$ alkyl$)$, $-NHC(=O)N(C_{1-6}$ alkyl$)_2$, $-NHC(=O)NH(C_{1-6}$ alkyl$)$, $-NHC(=O)NH_2$, $-C(=NH)O(C_{1-6}$ alkyl$)$, $-OC(=NH)(C_{1-6}$ alkyl$)$, $-OC(=NH)OC_{1-6}$ alkyl, $-C(=NH)N(C_{1-6}$ alkyl$)_2$, $-C(=NH)NH(C_{1-6}$ alkyl$)$, $-C(=NH)NH_2$, $-OC(=NH)N(C_{1-6}$ alkyl$)_2$, $-OC(NH)NH(C_{1-6}$ alkyl$)$, $-OC(NH)NH_2$, $-NHC(NH)N(C_{1-6}$ alkyl$)_2$, $-NHC(=NH)NH_2$, $-NHSO_2(C_{1-6}$ alkyl$)$, $-SO_2N(C_{1-6}$ alkyl$)_2$, $-SO_2NH(C_1$ alkyl$)$, $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl$)_3$, $-OSi(C_{1-6}$ alkyl$)_3$-$C(=S)N(C_{1-6}$ alkyl$)_2$, $C(=S)NH(C_{1-6}$ alkyl$)$, $C(=S)NH_2$, $-C(=O)S(C_{1-6}$ alkyl$)$, $-C(=S)SC_{1-6}$ alkyl, $-SC(=S)SC_{1-6}$ alkyl, $-P(=O)_2(C_{1-6}$ alkyl$)$, $-P(=O)(C_{1-6}$ alkyl$)_2$, $-OP(=O)(C_{1-6}$ alkyl$)_2$, $-OP(=O)(OC_{1-6}$ alkyl$)_2$, $C_1$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3{}^-$, $ClO_4{}^-$, $OH^-$, $H_2PO_4{}^-$, $HSO_4{}^-$, $SO_4{}^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols.

Compounds

In one aspect, the present invention features a compound of Formula (I):

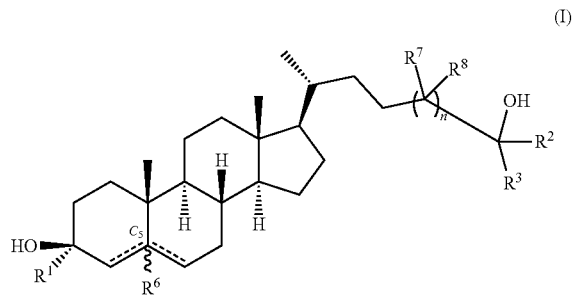

or a pharmaceutically acceptable salt thereof, wherein: $R^1$ is $C_{1-6}$ alkyl; each of $R^2$ and $R^3$ is independently hydrogen, $C_{1-6}$ alkyl, or carbocyclyl; or $R^2$ and $R^3$, together with the carbon atom to which they are attached, form a 3-8 membered ring; $R^6$ is absent or hydrogen; each of $R^7$ and $R^8$ is independently hydrogen, halogen, $C_{1-6}$ alkyl, or carbocyclyl; or each of $R^7$ and $R^8$, together with the carbon atom to which they are attached, form a 3-8 membered ring; or $R^2$ and $R^7$, together with the carbon atoms to which they are attached, form a 3-8 membered ring; n is 1, 2, or 3; and ==== represents a single or double bond, wherein when one ==== is a double bond, the other ==== is a single bond; and when one of the ==== is a double bond, $R^6$ is absent.

In some embodiments, $R^1$ is substituted $C_{1-6}$ alkyl. In some embodiments, $R^1$ is unsubstituted $C_{1-6}$ alkyl. In some embodiments, $R^1$ is methyl (e.g., $-CHF_2$, $-CH_3$, $-CF_3$, $-CH_2OCH_3$, or $-CH_2OCH_2CH_3$), ethyl, or isopropyl. In some embodiments, $R^1$ is $-CH_3$. In some embodiments, $R^1$ is ethyl.

In some embodiments, each of $R^2$ and $R^3$ is independently hydrogen, $C_{1-6}$ alkyl, or carbocyclyl, or wherein $R^2$ and $R^3$ are taken together with the carbon atom to which they are attached form a 3-8 membered ring. In some embodiments, the 3-8 membered ring is a carbocyclyl ring (e.g., cyclopropyl). In some embodiments, each of $R^2$ and $R^3$ is independently hydrogen, $C_{1-6}$ alkyl, or carbocyclyl. In some embodiments, each of $R^2$ and $R^3$ is independently hydrogen, methyl (e.g., $-CH_3$, $-CF_3$), ethyl (e.g., $-CH_2CH_3$, $CH_2CF_3$), propyl, isopropyl, cyclopropyl, or butyl.

In some embodiments, $R^2$ substituted $C_{1-6}$ alkyl. In some embodiments, $R^2$ unsubstituted $C_{1-6}$ alkyl.

In some embodiments, $R^2$ is hydrogen, methyl (e.g., $-CH_3$, $-CF_3$), ethyl, or isopropyl.

In some embodiments, $R^3$ substituted $C_{1-6}$ alkyl. In some embodiments, $R^3$ unsubstituted $C_{1-6}$ alkyl.

In some embodiments, $R^3$ is methyl (e.g., $-CH_3$, $-CF_3$), ethyl (e.g., $-CH_2CH_3$, $-CH_2CF_3$), propyl, isopropyl, cyclopropyl, or butyl.

In some embodiments, $R^2$ and $R^3$ are hydrogen. In some embodiments, $R^2$ is hydrogen and $R^3$ is $C_{1-6}$ alkyl (e.g., methyl (e.g., $-CH_3$, $-CF_3$), ethyl, isopropyl). In some embodiments, $R^2$ is $C_{1-6}$ alkyl and $R^3$ is $C_{1-6}$ alkyl. In some embodiments, $R^2$ and $R^3$ are $-CH_3$. In some embodiments, $R^2$ is $-CH_3$ and $R^3$ is $-CF_3$. In some embodiments, $R^2$ is $-CH_3$ and $R^3$ is ethyl. In some embodiments, $R^2$ is $-CH_3$ and $R^3$ is isopropyl.

In some embodiments, each of ==== is a single bond.

In some embodiments, $R^6$ is hydrogen. In some embodiments, $R^6$ is in the alpha position. In some embodiments, $R^6$ is in the beta position.

In some embodiments, $R^6$ is absent.

In some embodiments, $R^7$ and $R^8$ are hydrogen.

In some embodiments, n is 1. In some embodiments, n is 1 and $R^7$ and $R^8$ are hydrogen.

In some embodiments, n is 2. In some embodiments, n is 2 and each of $R^7$ and $R^8$ is independently hydrogen, halogen, $C_{1-6}$ alkyl, or carbocyclyl.

In some embodiments, the compound Formula (I) is a compound of Formula (II):

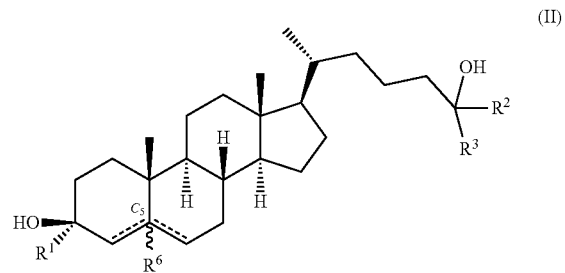
(II)

or a pharmaceutically acceptable salt thereof.

In some embodiments, the compound of Formula (II) is a compound of Formula (II-A) or Formula (II-B):

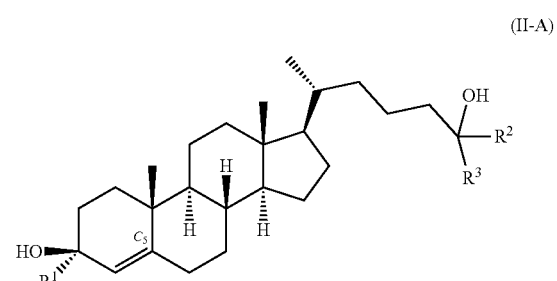
(II-A)

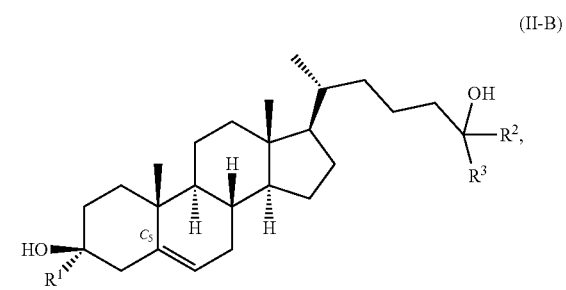
(II-B)

or a pharmaceutically acceptable salt thereof.

In some embodiments, the compound of Formula (I) is a compound of Formula (II-B-i) or Formula (II-B-ii):

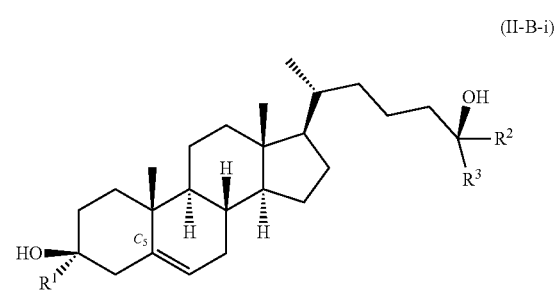
(II-B-i)

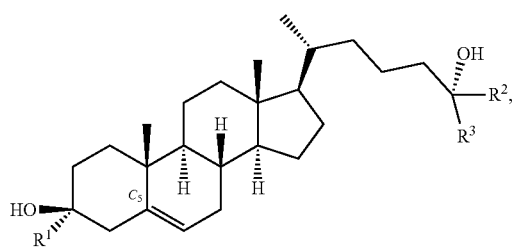

(II-B-ii)

or a pharmaceutically acceptable salt thereof.

In some embodiments, the compound of Formula (I) is a compound of Formula (II-B-iii):

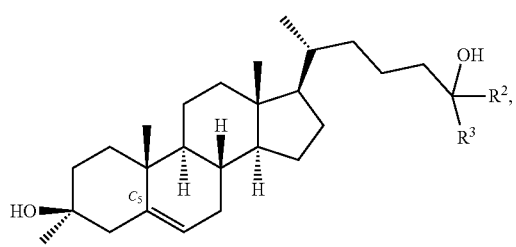

(II-B-iii)

or a pharmaceutically acceptable salt thereof.

In some embodiments, the compound of Formula (I) is a compound of Formula (III):

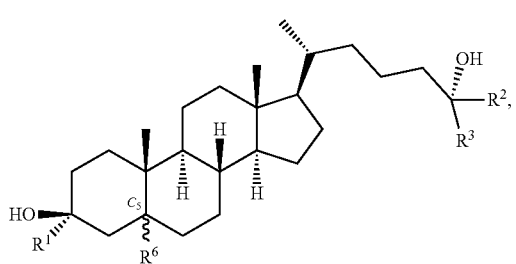

(III)

or a pharmaceutically acceptable salt thereof.

In some embodiments, the compound of Formula (III) is a compound of Formula (III-A) or Formula (III-B):

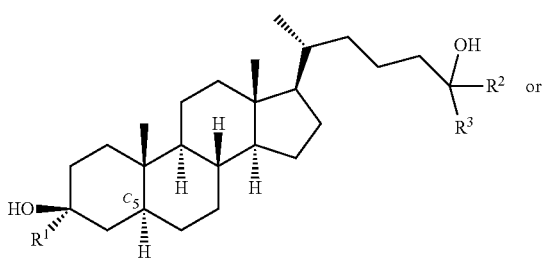

(III-A)

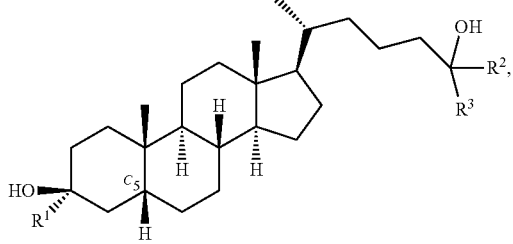

(III-B)

or a pharmaceutically acceptable salt thereof.

In some embodiments, the compound of Formula (III-B) is a compound of Formula (III-C) or Formula (III-D):

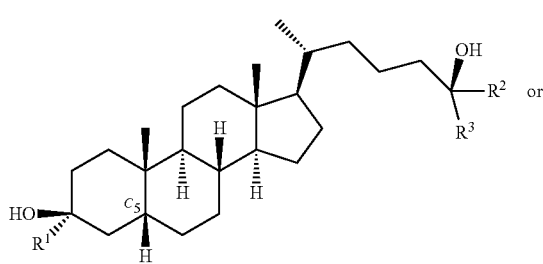

(III-C)

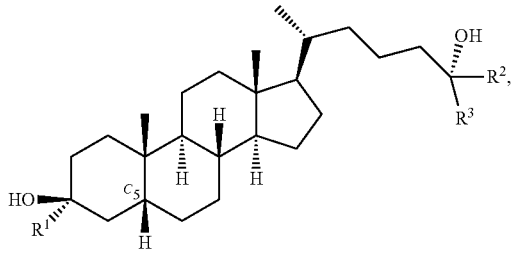

(III-D)

or a pharmaceutically acceptable salt thereof.

In some embodiments, the compound of Formula (III-A) is a compound of Formula (III-E) or Formula (III-F):

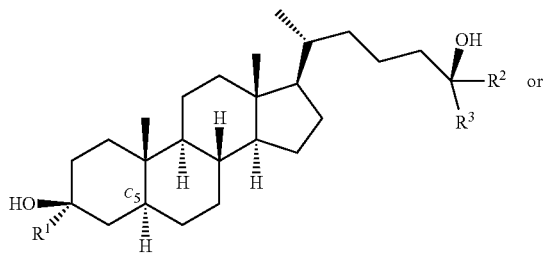

(III-E)

-continued

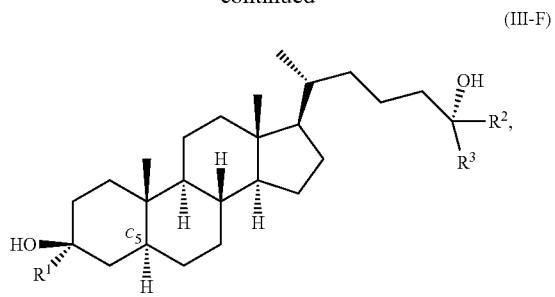
(III-F)

or a pharmaceutically acceptable salt thereof.

In some embodiments, the compound of Formula (III) is a compound of Formula (III-A-i-a) or Formula (III-B-i-a):

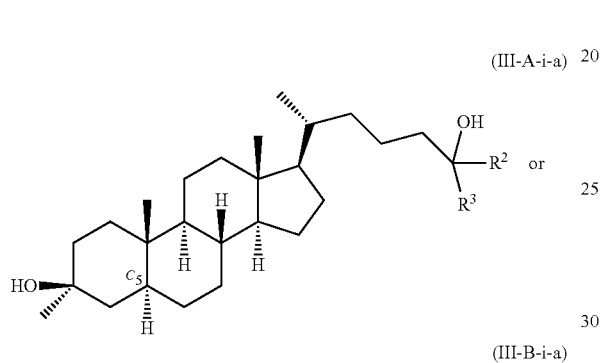
(III-A-i-a)

(III-B-i-a)

or a pharmaceutically acceptable salt thereof.

In some embodiments, $R^1$ is methyl (e.g., —CHF$_2$, —CF$_3$, —CH$_2$OCH$_3$, or —CH$_2$OCH$_2$CH$_3$), ethyl, or isopropyl.

In some embodiments, each of $R^2$ and $R^3$ is independently hydrogen, $C_{1-6}$ alkyl, or carbocyclyl, or wherein $R^2$ and $R^3$ are taken together with the carbon atom to which they are attached form a 3-8 membered ring.

In some embodiments, each of $R^2$ and $R^3$ is independently hydrogen, $C_{1-6}$ alkyl, or carbocyclyl.

In some embodiments, each of $R^2$ and $R^3$ is independently hydrogen, methyl (e.g., —CH$_3$, —CF$_3$), ethyl (e.g., —CH$_2$CH$_3$, —CH$_2$CF$_3$), propyl, isopropyl, cyclopropyl, or butyl.

In some embodiments, $R^2$ is hydrogen, methyl (e.g., —CH$_3$, —CF$_3$), or ethyl.

In some embodiments, $R^3$ is methyl (e.g., —CH$_3$, —CF$_3$), ethyl (e.g., —CH$_2$CH$_3$, —CH$_2$CF$_3$), propyl, isopropyl, cyclopropyl, or butyl.

In some embodiments, the compound is selected from the group consisting of:

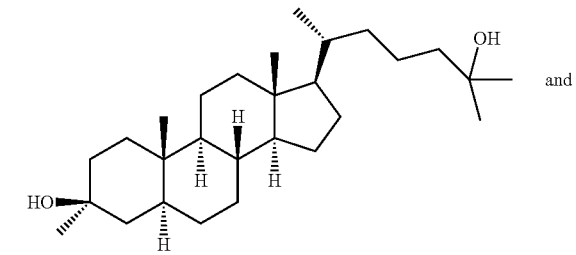
and

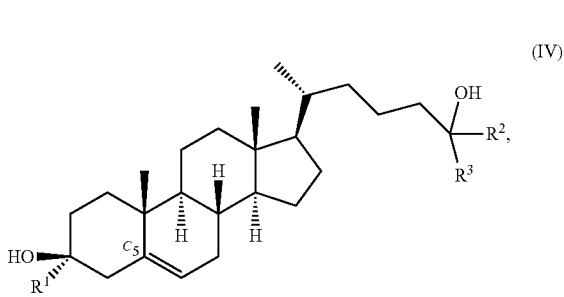

or a pharmaceutically acceptable salt thereof.

In some embodiments, the compound of Formula (I) is a compound of Formula (IV):

(IV)

or a pharmaceutically acceptable salt thereof.

In some embodiments, $R^1$ is methyl (e.g., —CHF$_2$, —CF$_3$, —CH$_2$OCH$_3$, or —CH$_2$OCH$_2$CH$_3$), ethyl, or isopropyl.

In some embodiments, each of $R^2$ and $R^3$ is independently hydrogen, $C_{1-6}$ alkyl, or carbocyclyl, or wherein $R^2$ and $R^3$ are taken together with the carbon atom to which they are attached form a 3-8 membered ring.

In some embodiments, each of $R^2$ and $R^3$ is independently hydrogen, $C_{1-6}$ alkyl, or carbocyclyl.

In some embodiments, each of $R^2$ and $R^3$ is independently hydrogen, methyl (e.g., —CH$_3$, —CF$_3$), ethyl (e.g., —CH$_2$CH$_3$, CH$_2$CF$_3$), propyl, isopropyl, cyclopropyl, or butyl.

In some embodiments, $R^2$ is hydrogen, methyl (e.g., —CH$_3$, —CF$_3$), or ethyl.

In some embodiments, $R^3$ is methyl (e.g., —CH$_3$, —CF$_3$), ethyl (e.g., —CH$_2$CH$_3$, —CH$_2$CF$_3$), propyl, isopropyl, cyclopropyl, butyl.

In some embodiments, the compound is:

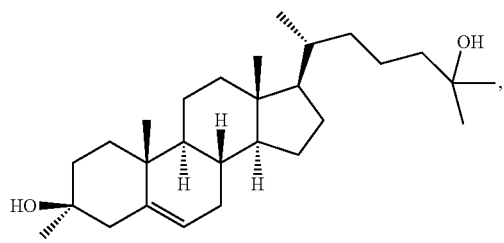

or a pharmaceutically acceptable salt thereof.

In some embodiments, the compound Formula (I) is a compound of Formula (V):

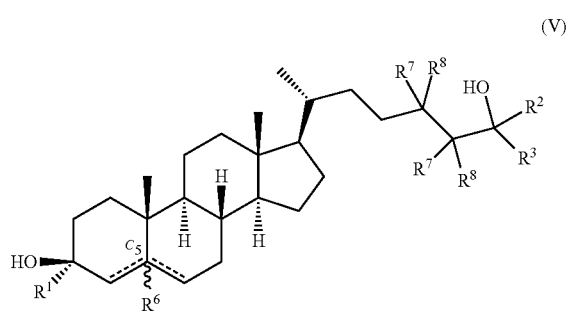

or a pharmaceutically acceptable salt thereof.

In some embodiments, the compound of Formula (I) is a compound of Formula (V-A):

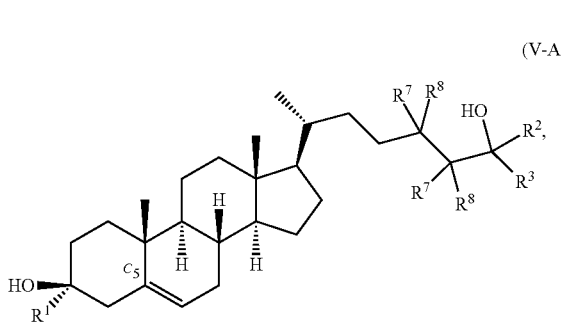

or a pharmaceutically acceptable salt thereof.

In some embodiments, the compound of Formula (I) is a compound of Formula (V-B):

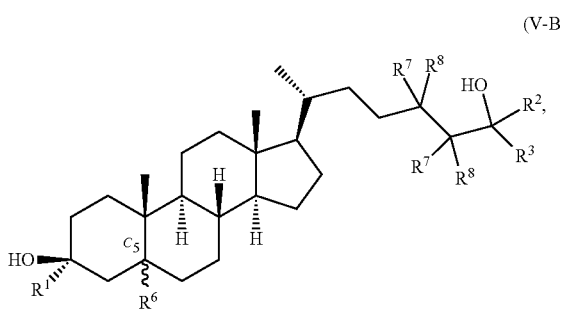

or a pharmaceutically acceptable salt thereof.

In some embodiments, the compound of Formula (III) is a compound of Formula (V-C) or Formula (V-D):

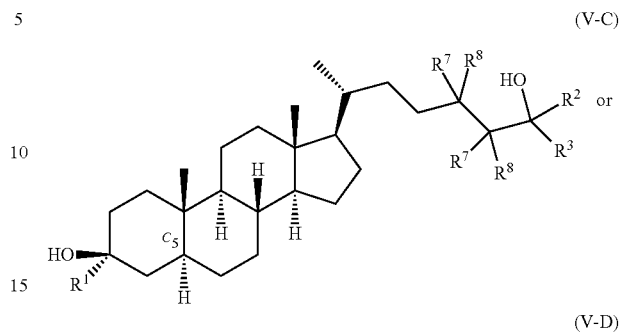

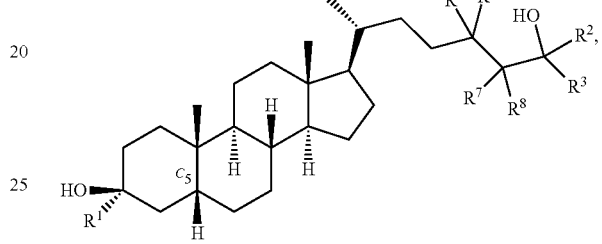

or a pharmaceutically acceptable salt thereof.

In some embodiments, the compound of Formula (I) is a compound of Formula (V-E):

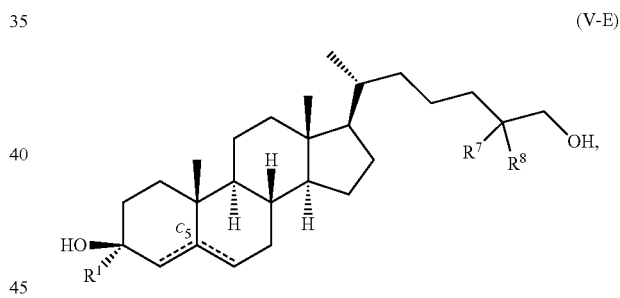

or a pharmaceutically acceptable salt thereof.

In some embodiments, the compound of Formula (V-E) is a compound of Formula (V-E-i):

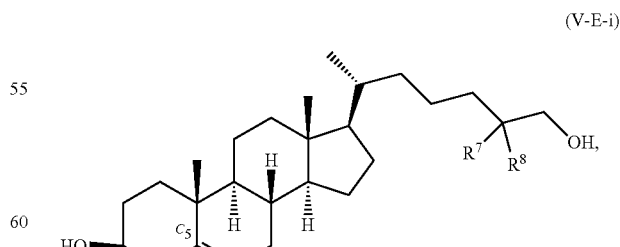

or a pharmaceutically acceptable salt thereof.

In some embodiments, the compound of Formula (I) is a compound of Formula (V-E-ii) or (V-E-iii):

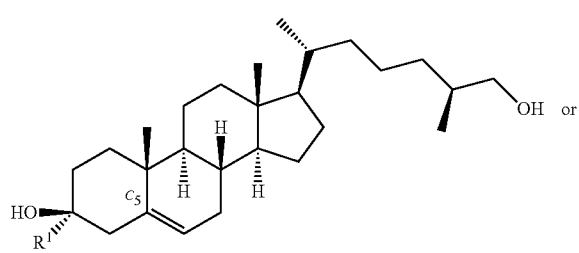
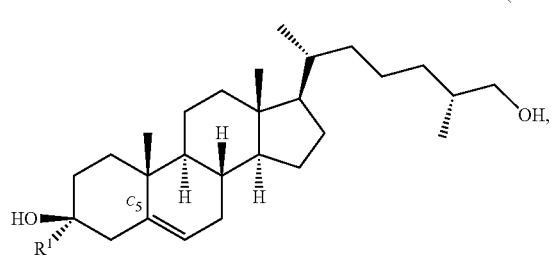
or a pharmaceutically acceptable salt thereof.
In some embodiments, the compound is selected from:
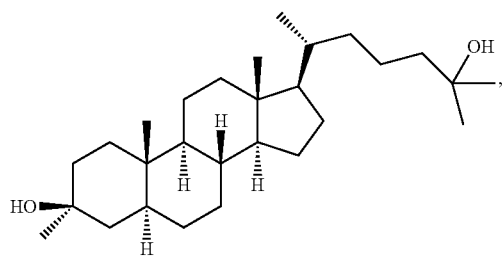
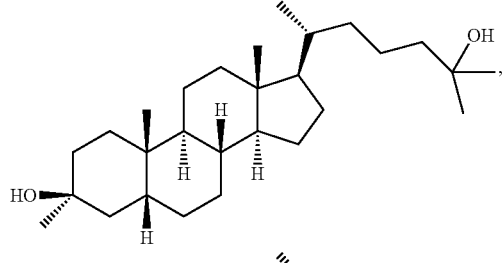
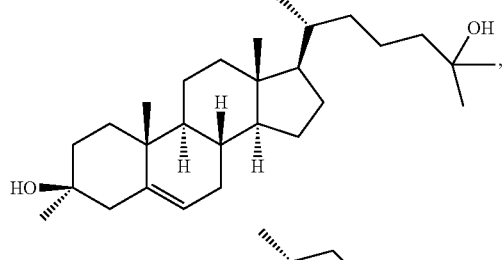
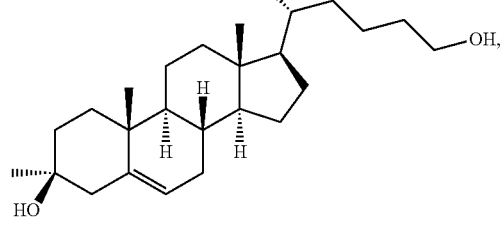
-continued
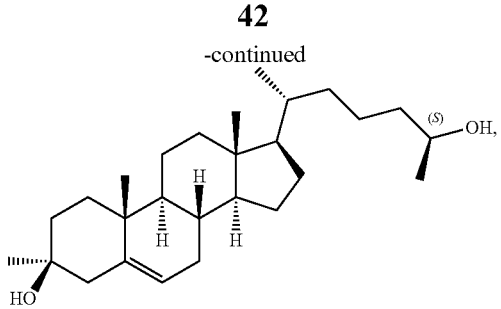
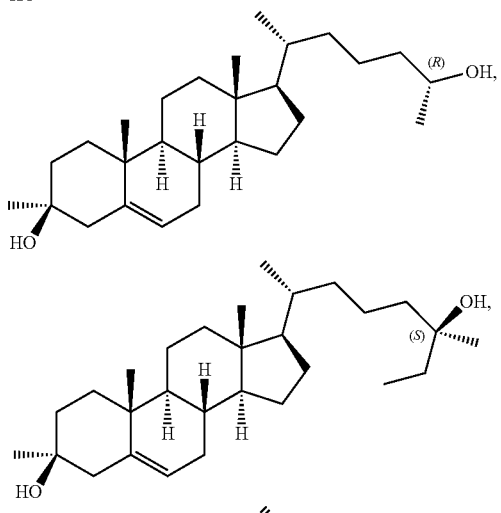
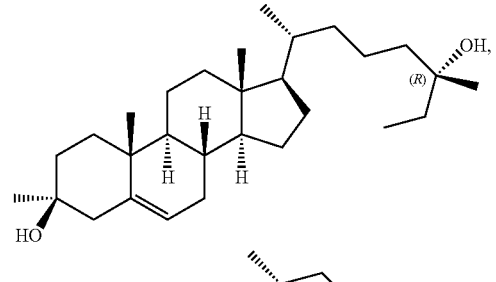
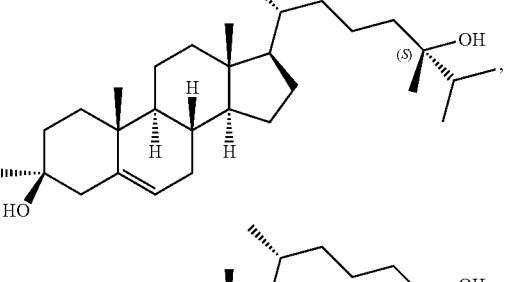
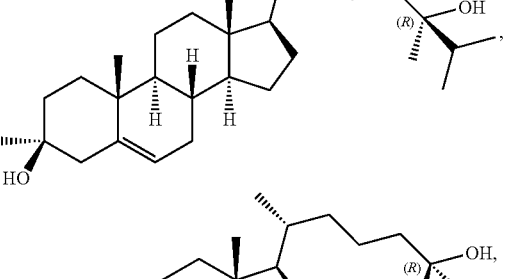
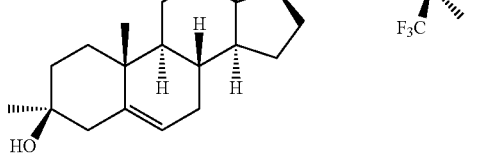

43
-continued
44
-continued
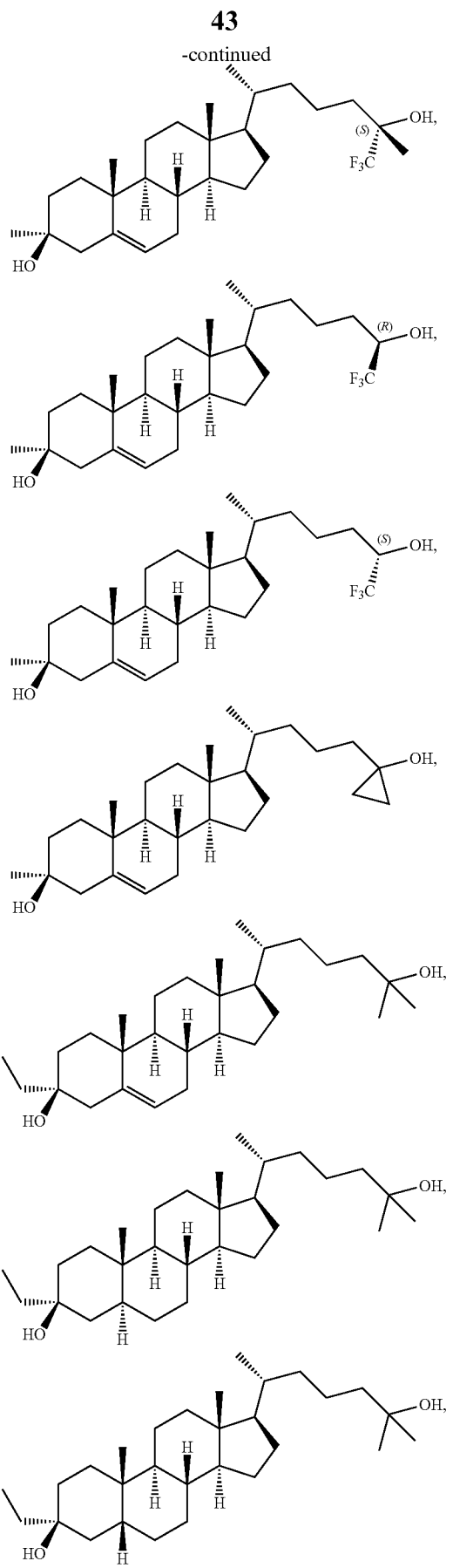
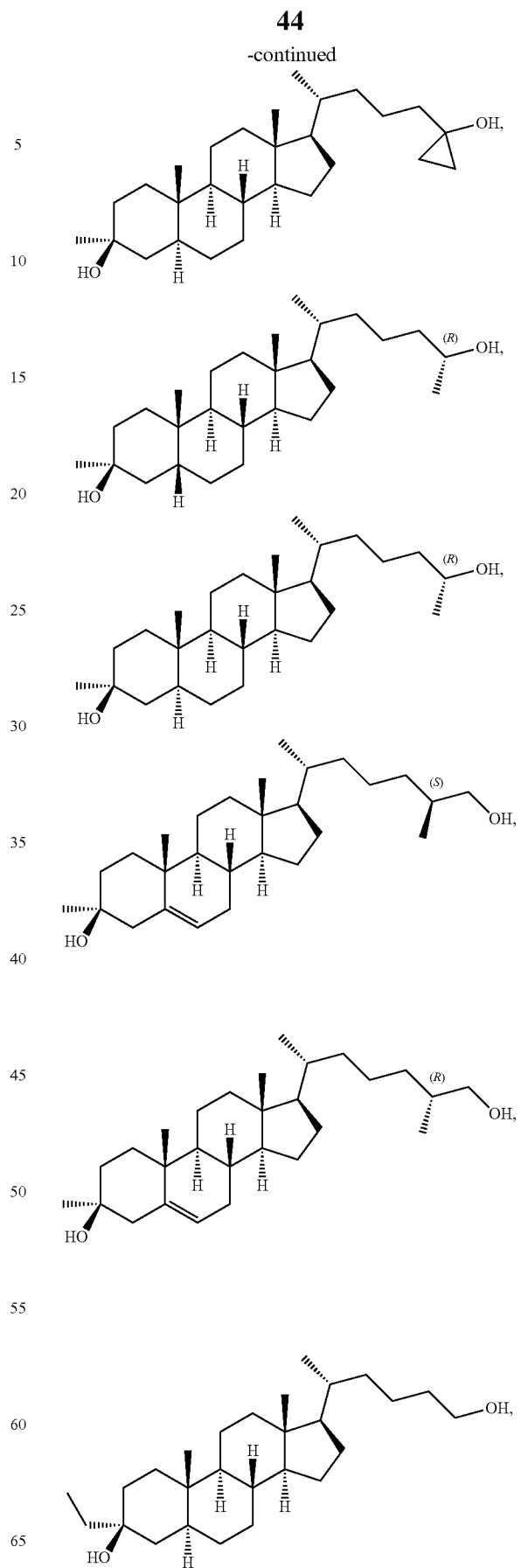

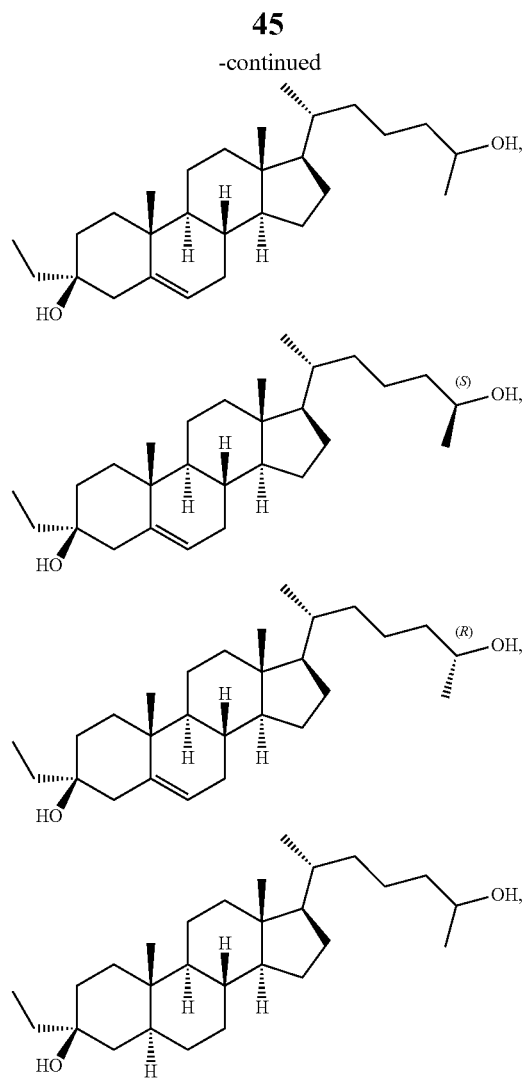
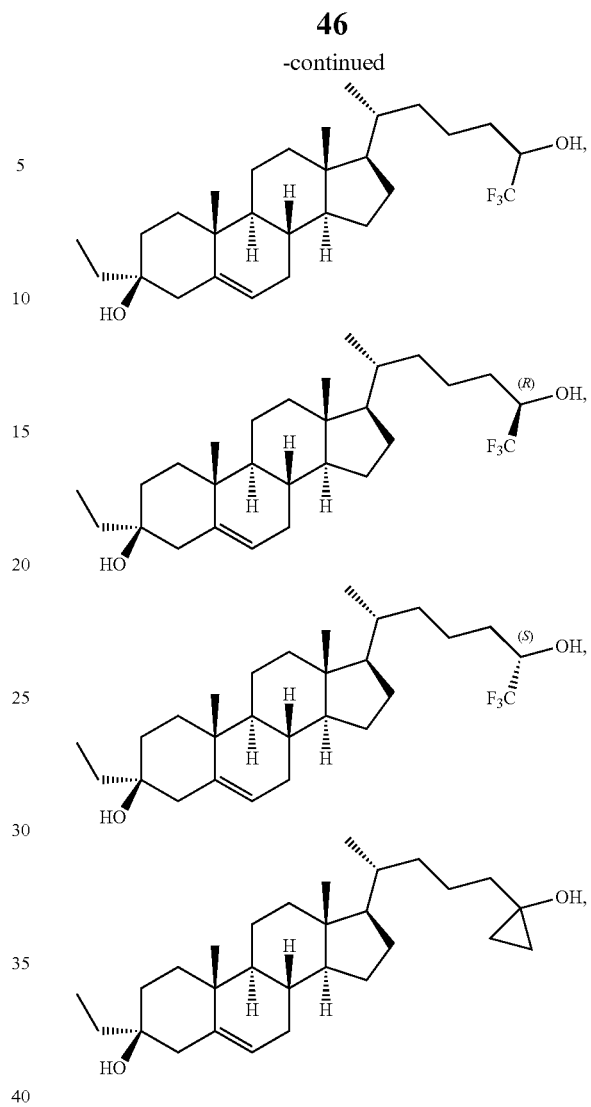
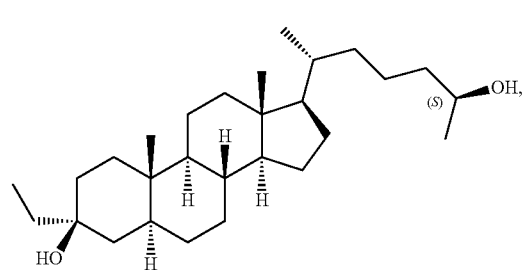
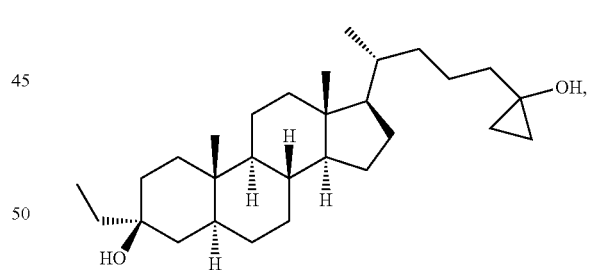
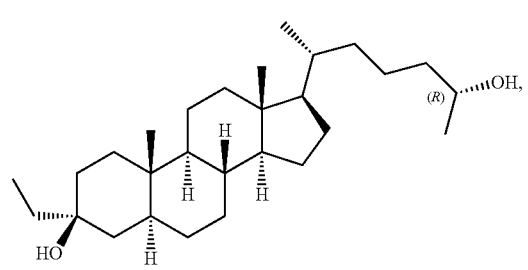
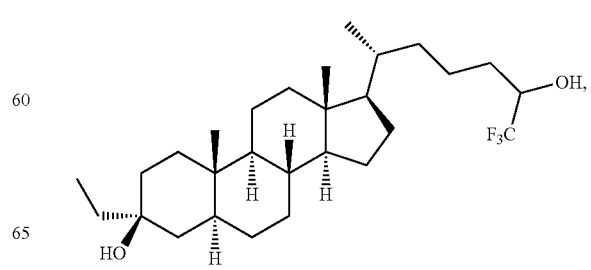

-continued

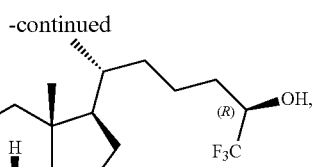

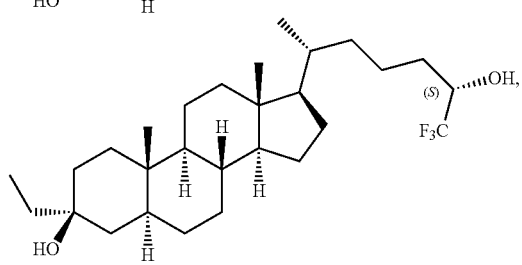

or a pharmaceutically acceptable salt thereof.

Pharmaceutical Compositions

In another aspect, the invention provides a pharmaceutical composition comprising a pharmaceutically acceptable carrier and an effective amount of a compound of Formula (I).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (I) or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of Formula (I). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula (I). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules:

A compound of Formula (I), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid:

A compound of Formula (I), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection:

A compound of Formula (I), or pharmaceutically acceptable salt thereof, may be dissolved or suspended in a buffered sterile saline injectable aqueous medium to a concentration of approximately 5 mg/mL.

Exemplary Formulation 6—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets:

A compound of Formula (I), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (I), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (I), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula (I), or pharmaceutically acceptable salt thereof, may act as a negative allosteric modulator (NAM) of NMDA, and inhibit NMDA receptor function. In certain embodiments, the present invention, e.g., a compound of Formula (I), or pharmaceutically acceptable salt thereof, may act as positive allosteric modulators (PAM) of NMDA, and potentiate NMDA receptor function. In certain embodiments, the compound of Formula (I), or pharmaceutically acceptable salt thereof, modulates NMDA function, but does not act as a negative allosteric modulator (NAM) or positive allosteric modulator (PAM) of NMDA.

In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable blowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Exemplary conditions related to NMDA-modulation includes, but are not limited to, gastrointestinal (GI) disorder, e.g., constipation, irritable blowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary CNS conditions related to NMDA-modulation include, but are not limited to, adjustment disorders, anxiety disorders (including obsessive-compulsive disorder, post-traumatic stress disorder, social phobia, generalized anxiety disorder), cognitive disorders (including Alzheimer's disease and other forms of dementia (e.g., frontotemporal dementia)), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, pain (including acute and chronic pain; headaches, e.g., migraine headaches), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of the present invention, e.g., a compound of Formula (I), or pharmaceutically acceptable salt thereof, can be used to induce sedation or anesthesia. In certain embodiments, the compound of Formula (I), or pharmaceutically acceptable salt thereof, is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, sterol synthesis disorders, pain, seizure disorders, stroke, traumatic brain injury, movement disorders and vision impairment, hearing loss, and tinnitus. In some embodiments, the disorder is Huntington's disease. In some embodiments, the disorder is Parkinson's disease. In some embodiments, the disorder is an inflammatory disease (e.g., lupus).

In another aspect, provided is a method of treating or preventing brain excitability in a subject susceptible to or afflicted with a condition associated with brain excitability, comprising administering to the subject an effective amount of a compound of the present invention, e.g., a compound of Formula (I), or a pharmaceutically acceptable salt thereof.

In yet another aspect, the present invention provides a combination of a compound of the present invention, e.g., a compound of Formula (I), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Diseases and Disorders

Described herein are methods of treating a sterol synthesis disorder. Exemplary disorders are described herein. The methods include administering to a subject, e.g., a subject suffering from a sterol synthesis disorder such as SLOS, a NMDA receptor modulating compound. Exemplary compounds are described herein.

Sterol Synthesis Disorders

In one aspect, described herein are methods for treating a sterol synthesis disorder. Cholesterol has an essential rule in growth and development. It is a membrane lipid and a precursor to many molecules that play important roles in cellular growth and differentiation, protein glycosylation, and signaling pathways. Biosynthesis of cholesterol involves a number of enzymes and intermediates. Disorders resulting from a deficiency in any of the enzymes involved in cholesterol biosynthesis lead to the accumulation of intermediates and imbalance in biomolecules, resulting in disorders including congenital skeletal malformations, dysmorphic facial features, psychomotor retardation, and failure to thrive. In an embodiment, a sterol synthesis disorder or symptom of a sterol synthesis disorder can be treated by administering to a subject suffering from a sterol synthesis disorder a compound described herein, such as a NMDA receptor modulating compound as described herein. Additional disorders are described below.

Smith-Lemli-Opitz Syndrome

In one aspect, described herein are methods for treating Smith-Lemli-Opitz Syndrome (or SLOS, or 7-dehydrocholesterol reductase deficiency). SLOS is an inborn error of cholesterol synthesis. In addition to microcephaly, moderate to severe intellectual disability, sensory hypersensitivity, stereotyped behaviors, dysmorphic facial features, and syndactyly of the second/third toes, a feature of the disease is reduced cerebrosterol (24(S)-hydroxycholesterol) levels. SLOS is an autosomal recessive genetic condition resulting from deficiency in the final enzyme of the cholesterol synthesis pathway, and causes low or low-normal plasma cholesterol levels and increased 7- and 8-dehydrocholesterol (DHC; 7DHC and 8DHC) levels. Common therapies currently used include dietary cholesterol supplementation, treatment with 3-hydroxy-3-methylglutaryl coenzyme A reductase inhibitors (HMG CoA reductase inhibitors, also known as statins), and treatment with agents that enhance cholesterol production and/or accretion; and to decrease the accumulation of 7DHC and 8DHC, the potentially toxic precursors of cholesterol.

Desmosterolosis

Desmosterolosis is a deficiency in desmosterol reductase and has a similar phenotype to SLOS. In one aspect, described herein are methods for treating desmosterolosis with compounds described herein.

Sitosterolemia

Sitosterolemia is a rare autosomal recessive disorder caused by mutations in two ATP-binding cassette (ABC) transporter genes (ABCG5 and ABCG8). Sitosterolemia enhances the absorption of plant sterols and cholesterol from the intestines. Patients typically present with tendon and tuberous xanthomas and premature coronary artery disease. In one aspect, described herein are methods for treating sitosterolemia with compounds described herein.

Cerebrotendinous Xanthomatosis (CTX)

In one aspect, described herein are methods for treating cerebrotendinous xanthomatosis (also referred to as cerebral cholesterosis, or Van Bogaert-Scherer-Epstein syndrome) with compounds described herein. CTX can be caused by a mutation in the CYP27A1 gene, which produces the sterol 27-hydroxylase enzyme. Sterol 27-hydroxylase metabolizes cholesterol into bile acids (e.g., chenodeoxycholic acid) that are important in the absorption of fats in the intestine. Enzyme dysfunction can lead to cholesterol accumulation in tissues. CTX is characterized by childhood diarrhea, cataracts, tendon xanthomas, reduced mental capability and abnormal movements in adults.

Mevalonate Kinase Deficiency Syndromes (MKD)

Mevalonate Kinase Deficiency (also referred to as mevalonic aciduria (a more severe form of MKD), or Hyper IgD Syndrome (HIDS, or hyperimmunoglobulinemia D) with period fever syndrome (a more benign form of MKD)) causes an accumulation of mevalonic acid in the urine as a result of insufficient activity of mevalonate kinase. MKD can result in developmental delay, hypotonia, anemia, hepatosplenomegaly, dysmorphic features, mental retardation, and overall failure to thrive. Mevalonic aciduria is characterized by delayed physical and mental development, failure to thrive, recurrent episodes of fever with vomiting and diarrhea, enlarged liver, spleen and lymph nodes, microcephaly (small head size), cataract, low muscle tone, short statute, distinct facial features, ataxia, and anemia. HIDS is characterized by recurrent episodes of fever associated with swollen lymph nodes, joint pain, gastrointestinal issues and skin rash. In one aspect, described herein are methods for treating MKD with the compounds described herein.

SC4MOL Gene Mutation (SMO Deficiency)

SC4MOL gene deficiency is a genetic disorder in the cholesterol biosynthesis pathway (e.g., mutations in the SC4MOL gene encoding a novel sterol oxidase). SC$MOL deficiency is characterized by the accumulation of dimethyl and monomethyl sterols that can be detected in blood, skin flakes or primary skin fibroblasts. In one aspect, described herein are methods for treating SMO deficiency with compounds described herein.

Niemann-Pick Disease

Niemann-Pick disease is a lysosomal storage disease resulting from a genetic mutation that affects metabolism. Niemann-Pick disease leads to abnormal accumulation of cholesterol and other fatty substances (lipids) due to an inability of the body to transport the substances. The accumulation damages the affected areas.

Autism

In one aspect, described herein are methods for treating autism spectrum disorder or autism. Autism spectrum disorder (ASD) and autism refer to a group of complex disorders of brain development. Autism is typically characterized by difficulties in social interaction, for example in verbal and nonverbal communication. Repetitive behaviors are also often seen in individuals having autism. Autism can be associated with intellectual disability, difficulties in motor coordination and attention and physical health issues, e.g., sleep and gastrointestinal disturbances. Individuals having autism can also excel in visual skills, music, math and art. Autism can refer to autistic disorder, childhood disintegrative disorder, pervasive developmental disorder—not otherwise specified (PDD-NOS), and Asperger syndrome. Autism also refers to monogenetic causes of autism such as synaptophathy's, e.g., Rett syndrome, Fragile X syndrome, Angelman syndrome.

Disorders Associated with Phenylketonuria

In one aspect, described herein are methods for treating disorders associated with phenylketonuria (e.g., cognitive disorders) with compounds described herein. Phenylketonuria can lead to hypochesterolemia and lowered vitamin D status. Total and low-density cholesterols and 25-hydroxy vitamin D have been found to be decreased in subjects suffering from phenylketonuria as compared with subjects not suffering from phenylketonuria (*Clin. Chin. Acta* 2013, 416: 54-59). 24S-hydroxycholesterol and 27S-hydroxycholesterol and 7a-hydroxycholesterol (e.g., representing peripheral and hepatic cholesterol elimination, respectively) have been shown to be significantly decreased in subjects suffering from phenylketonuria, while 7β-hydroxycholesterol (e.g., reflecting oxidative stress) was increased significantly in subjects suffering from phenylketonuria. Changes in the levels of 24S-OHC and 7β-hydroxycholesterol correlate with phenylalanine level, and 27S-hydroxycholesterol levels may correlate with the 25-hydroxy vitamin D level in subjects suffering from phenylketonuria.

Abbreviations

PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)$_4$Ti: titanium tetraisopropoxide; BHT: 2,6-di-t-butyl-4-methylphenoxide; Me: methyl; Ph: phenyl; Et: ethyl; Bz: benzoyl; DCC: dicyclohexylcarbodiimide; DCM: dichloromethane; DMAP: 4-dimethylaminopyridine; DMP: Dess-Martin periodinane; EtOAc: ethyl acetate; TEA: triethylamine; AlaOH: alanine; Boc: t-butoxycarbonyl. Py: pydidine; TBAF: tetra-n-butylammonium fluoride; THF: tetrahydrofuran; TMS: trimethylsilyl. MAD: methyl aluminum bis(2, 6-di-t-butyl-4-methylphenoxide); Na$_2$SO$_4$: sodium sulfate; Na$_2$S$_2$O$_3$: sodium thiosulfate; PE: petroleum ether; MeCN:

acetonitrile; MeOH: methanol; Py: pyridine, Boc: t-butoxycarbonyl; MTBE: methyl tert-butyl ether.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

The stereochemistry assigned herein (e.g., the assignment of "R" or "S" to the C25 or C27 position of the steroid) may be tentatively (e.g., randomly) assigned. For example, a C25 position may be drawn in the "R" configuration when the absolute configuration is "S." A C25 position may also be drawn in the "S" configuration when the absolute configuration is "R."

Example 1. Synthesis of Compound 1

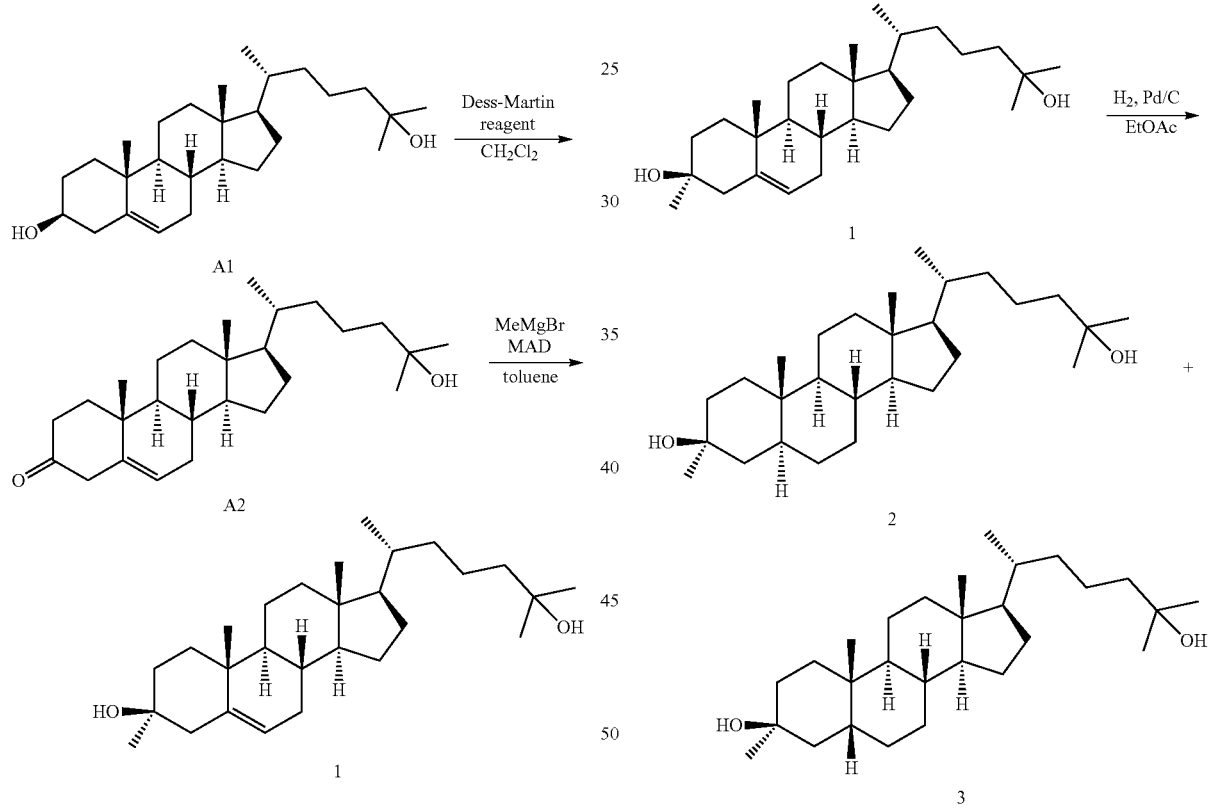

Step 1.
To a solution of reactant A1 (700 mg, 1.73 mmol) in dry $CH_2Cl_2$ (5 mL) was added Dess-Martin reagent (1.09 g, 2.59 mmol) in portions at 0° C. The reaction mixture was stirred at 25° C. for 3 h. The mixture was quenched with saturated aqueous $NaHCO_3/Na_2S_2O_3$ (1:3, 15 mL) and extracted with EtOAc (2×50 mL). The organic phase was then washed with brine (50 mL), dried over $Na_2SO_4$ and concentrated to afford A2 as a crude residue (700 mg), which was directly used in the next step without further purification.

Step 2.
To a solution of BHT (2.29 g, 10.4 mmol) in toluene (10 mL) was added a solution of $AlMe_3$ (2.61 mL, 5.22 mmol) in 2 M in toluene at 25° C. The resulting mixture was stirred at 25° C. for 1 h, after which a solution of A2 (700 mg, 1.74 mmol) in toluene (5 mL) was added at −78° C. under nitrogen. The mixture was stirred for an additional for 30 min, after which MeMgBr (3.0 M in $Et_2O$, 1.74 mL, 5.22 mmol) was added dropwise at −78° C. The reaction mixture was stirred at this temperature for 3 h, then quenched with saturated aqueous $NH_4Cl$ solution (30 mL) at −78° C. The resulting suspension was filtered and the filter cake was washed with EtOAc (2×50 mL). The combined organic phases were dried over $Na_2SO_4$, concentrated and purified by silica gel (PE/EtOAc=10/1 to 8/1) to afford Compound 1 (120 mg, 17%) as an off white solid. $^1$H NMR (400 MHz, $CDCl_3$) δ 5.30 (d, J=3.6 Hz, 1H), 2.40-2.30 (m, 1H), 1.99-1.98 (m, 3H), 1.70-1.57 (m, 4H), 1.46-1.17 (m, 28H), 1.11-0.92 (m, 8H), 0.67 (s, 3H). LCMS Rt=1.503 min in 2 min chromatography, 10-80AB, MS ESI calcd. for $C_{28}H_{49}O_2$ $[M+H]^+$ 417, found $C_{28}H_{45}$ $[M-2H_2O+H]^+$ 381.

Example 2. Synthesis of Compounds 2 and 3

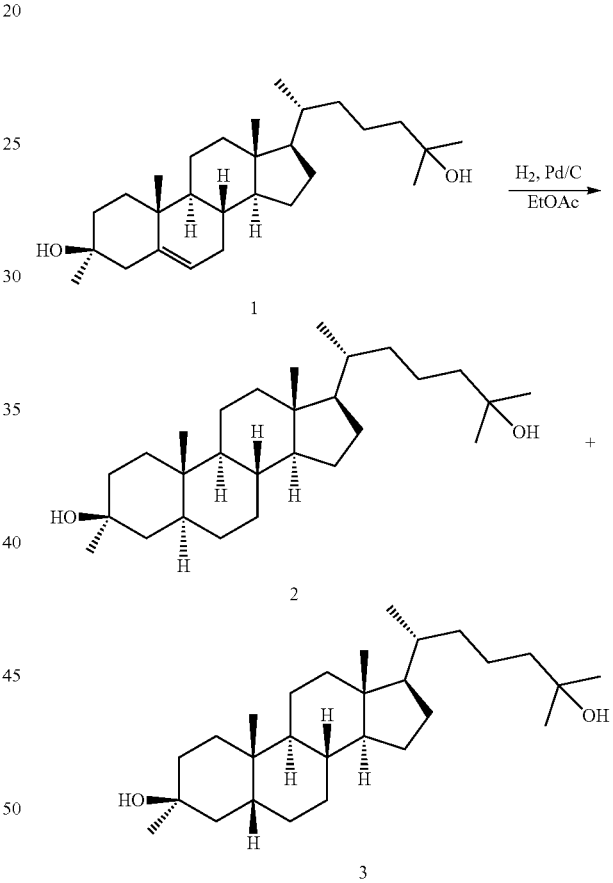

Step 1.
To a solution of Compound 1 (55 mg, 0.131 mmol) in EtOAc (10 mL) was added Pd/C (50 mg). The reaction mixture was stirred under hydrogen (50 psi) at 50° C. for 12 h, after which time it was filtered through a pad of celite. The filtrate was concentrated under reduced pressure and the resulting residue was purified by silica gel (PE/EtOAc=10/1) to afford both Compound 2 (5 mg, 9%) and Compound 3 (47.8 mg, 87%), each as an off white solid. Compound 2: $^1$H NMR (400 MHz, $CDCl_3$) δ 1.96 (d, J=12.4 Hz, 1H), 1.80-1.62 (m, 1H), 1.60-1.57 (m, 3H), 1.46-1.24 (m, 28H), 1.21-0.92 (m, 10H), 0.90 (s, 3H), 0.70-0.64 (m, 4H). LCMS Rt=1.568 min in 2 min chromatography, 10-80AB, MS ESI calcd. for $C_{28}H_{51}O_2$ [M+H]$^+$ 419, found $C_{28}H_{47}$ [M−2H$_2$O+H]$^+$ 383 Compound 3: $^1$H NMR (400 MHz, CDCl$_3$) δ 1.98-1.79 (m, 5H), 1.75-1.57 (m, 2H), 1.55-0.98 (m, 34H), 0.96 (s, 3H), 0.91 (d, J=8.4 Hz, 3H), 0.64 (s, 3H). LCMS Rt=1.590 min in 2 min chromatography, 10-80AB, MS ESI calcd. for $C_{28}H_{51}O_2$ [M+H]$^+$ 419, found $C_{28}H_{47}$ [M−2H$_2$O+H]$^+$ 383.
Example 3. Synthesis of Compounds 4, 5, and 6
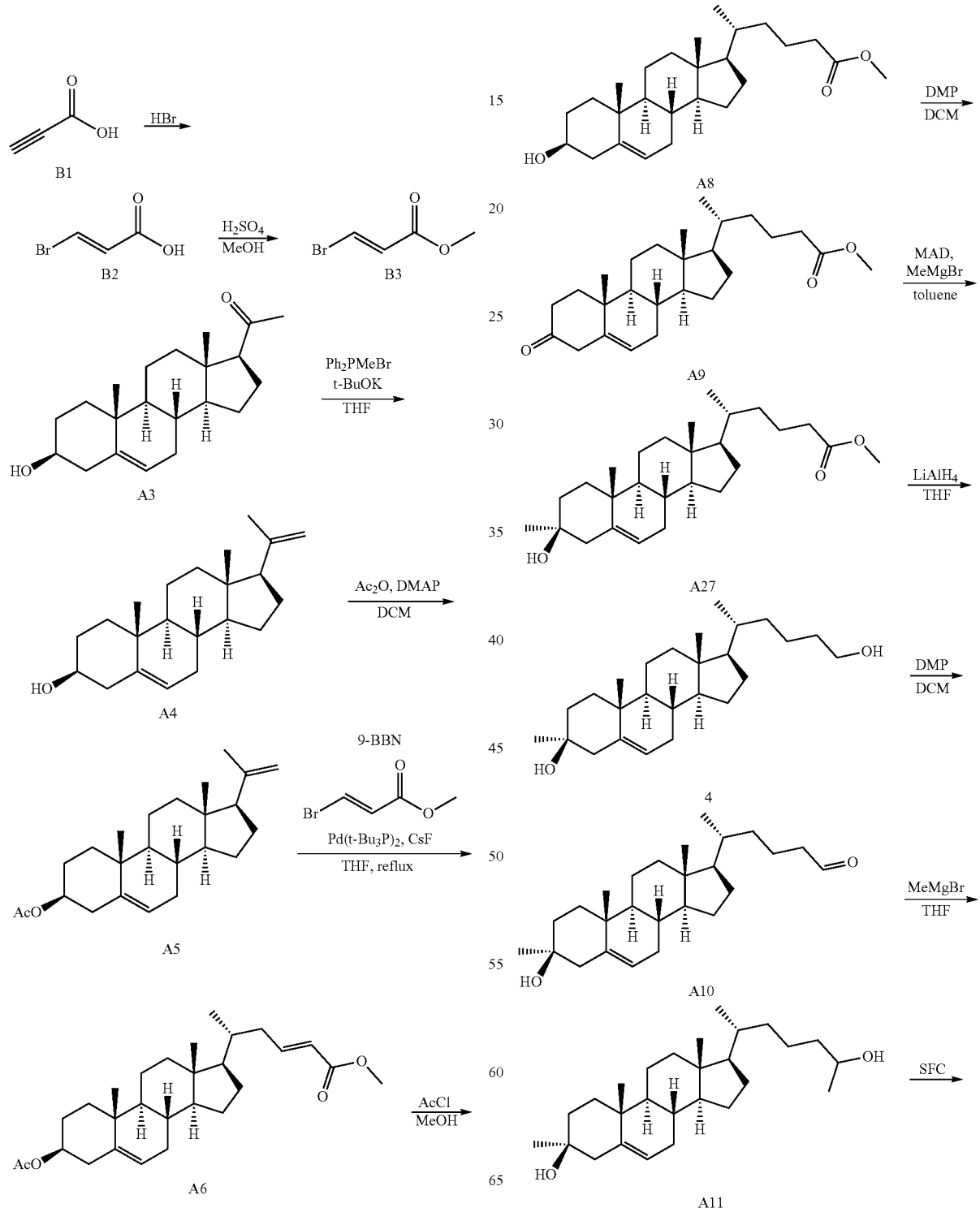

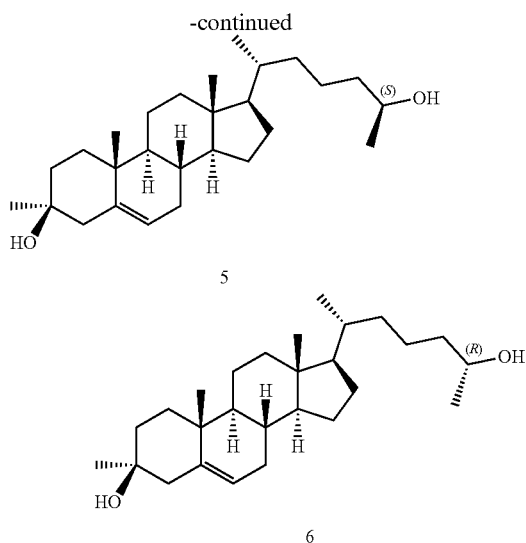

Step 1.

A mixture of propiolic acid B1 (20 g, 285 mmol) in 40% HBr (150 mL) was stirred at 110° C. for 2 hrs. The mixture was cooled in ice water. The precipitated solid was filtered out and washed with excess water to give B2 (25 g, 58%) as a brown solid. $^1$H NMR (400 MHz, CDCl$_3$) δ 9.69 (br. s., 1H), 7.76 (d, J=14.4 Hz, 1H), 6.54 (d, J=13.6 Hz, 1H).

Step 2.

To a suspension of B2 (8.5 g, 56.3 mmol) in MeOH (15 mL) was added 98% H$_2$SO$_4$ (2.80 g, 28.1 mmol). The mixture was stirred at 25° C. for 24 hrs. The reaction mixture was evaporated in vacuum. The distillation was washed with water (20 mL). The organic layer was separated and dried over Na$_2$SO$_4$ to give B3 (7 g, 75%) as colorless oil.

$^1$H NMR (400 MHz, CDCl$_3$) δ 7.61 (d, J=14.0 Hz, 1H), 6.53 (d, J=14.0 Hz, 1H), 3.76 (s, 3H).

Step 3.

To a suspension of Ph$_3$PMeBr (67.5 g, 189 mmol) in anhydrous THF (300 mL) under N$_2$ was added t-BuOK (21.2 g, 189 mmol). After stirred at 60° C. for 30 min, A3 (20 g, 63.1 mmol) was added. The resulting mixture was stirred at 60° C. for 4 hrs. The reaction mixture was poured into ice water (500 mL), extracted with EtOAc (2×500 mL). The combined organic layer was dried over Na$_2$SO$_4$, filtered and concentrated. The residue was purified by column chromatography on silica gel (PE/EtOAc=15/1) to give A4 (18 g, 91%) as an off white solid.

$^1$H NMR (400 MHz, CDCl$_3$) δ 5.39-5.32 (m, 1H), 4.85 (s, 1H), 4.71 (s, 1H), 3.59-3.47 (m, 1H), 2.36-2.17 (m, 2H), 2.07-1.94 (m, 2H), 1.89-1.65 (m, 9H), 1.60-1.39 (m, 6H), 1.26-0.92 (m, 8H), 0.59 (s, 3H).

Step 4.

To a solution of A4 (18 g, 57.2 mmol) in anhydrous DCM (150 mL) was added Ac$_2$O (8.75 g, 85.8 mmol) and DMAP (13.9 g, 114 mmol). The mixture was stirred at 25° C. for 2 hrs. The reaction mixture was diluted with water (200 mL), extracted with DCM (3×150 mL). The combined organic layer was washed with saturated NaHCO$_3$ (150 mL) and brine (150 mL), dried over anhydrous Na$_2$SO$_4$, filtered and concentrated to give A5 (20 g, 99%) as an off white solid.

Step 5.

To solution of A5 (30 g, 84.1 mmol) in anhydrous THF (150 mL) under nitrogen atmosphere at 30° C. was added 9-BBN (0.5 M in THF, 185 mL, 92.5 mmol). The mixture was stirred at 75° C. for 3 hrs. The reaction mixture was cooled to 30° C., and (E)-methyl 3-bromoacrylate (15.2 g, 92.5 mmol), CsF (25.5 g, 168 mmol) and Pd(t-Bu$_3$P)$_2$ (4.55 g, 8.40 mmol) were added. The resulting mixture was stirred at 75° C. for 16 hrs. The reaction was cooled, quenched with water (300 mL), extracted with EtOAc (3×300 mL). The combined organic layer was dried over Na$_2$SO$_4$, filtered through a pad of silica gel and concentrated. The residue was triturated from MeOH to give A6 (20 g, 54%) as an off white solid. $^1$H NMR (400 MHz, CDCl$_3$) δ 7.00-6.90 (m, 1H), 5.81 (d, J=15.6 Hz, 1H), 5.37 (d, J=4.5 Hz, 1H), 4.66-4.53 (m, 1H), 3.73 (s, 3H), 2.36-2.24 (m, 3H), 2.03 (s, 3H), 2.00-1.79 (m, 6H), 1.65-1.38 (m, 8H), 1.34-1.05 (m, 6H), 1.01 (s, 3H), 0.95 (d, J=6.5 Hz, 3H), 0.69 (s, 3H).

Step 6.

To suspension of A6 (20 g, 45.1 mmol) in anhydrous MeOH (250 mL) was added AcCl (2.82 g, 36.0 mmol). The mixture was stirred at 25° C. for 16 hrs. The reaction mixture was concentrated to remove most of MeOH, diluted with EtOAc (500 mL), washed with saturated NaHCO$_3$ (500 mL), brine (300 mL), dried over anhydrous Na$_2$SO$_4$, filtered and concentrated. The residue was purified by column chromatography on silica gel (PE/EtOAc/DCM=8/1/1) to give A7 (12 g, 67%) as a off white solid.

Step 7.

To a solution of A7 (12 g, 29.9 mmol) in THF (150 mL) was added 5% Pt/C (2 g). The mixture was degassed and purged with H$_2$ several times, stirred under a H$_2$ balloon at 25° C. for 4 hrs. The reaction mixture was filtered through a pad of Celite, and the filtrate was concentrated to give A8 (12 g, 100%) as an off white solid. $^1$H NMR (400 MHz, CDCl$_3$) δ 5.34 (d, J=5.0 Hz, 1H), 3.66 (s, 3H), 3.57-3.45 (m, 1H), 2.33-2.21 (m, 4H), 2.05-1.65 (m, 7H), 1.48-1.32 (m, 6H), 1.31-0.88 (m, 17H), 0.67 (s, 3H).

Step 8.

To a solution of A8 (27 g, 67.0 mmol) in DCM (300 mL) was added DMP (85.2 g, 201 mmol) at 25° C. The reaction was stirred at 25° C. for 1 h. The reaction was stirred at 25° C. for 1 h. The mixture was poured into saturated Na$_2$S$_2$O$_3$ (400 ml) at 0° C. and extracted with EtOAc (3×300 mL). The combined organic layers were washed with saturated NaHCO$_3$ (2×250 mL), brine (200 mL), dried over Na$_2$SO$_4$, filtered and concentrated in vacuum to give A9 (27 g, crude) as an oil, which was used for next step directly without further purification.

Step 9.

To a solution of BHT (88.8 g, 403 mmol) in toluene (250 mL) was added AlMe$_3$ (100 mL, 201 mmol, 2 M in toluene) dropwise below 25° C. The solution was stirred at 25° C. for 1 h. A solution of A9 (27 g, 67.3 mmol) in toluene (250 mL) was added dropwise at −78° C. After stirring at −78° C. for 1 h, MeMgBr (67.0 mL, 201 mmol, 3M in ethyl ether) was added dropwise at −78° C. The resulting solution was stirred between −78° C. and −50° C. for 3 hrs. The reaction was quenched by saturated citric acid solution (400 mL) at −78° C. After stirring at 25° C. for 0.5 h, the resulting mixture was filtered and the filtrate was extracted with EtOAc (3×300 mL). The combined organic layer was dried over Na$_2$SO$_4$, filtered and concentrated in vacuum. The crude product was purified by a silica gel column (PE/EtOAc=5/1) to give the product (18.5 g, 66%) and 70 mg of the product was recrystallized (PE/EtOAc=10 mL/2 mL) to give A27 (67 mg) as an off white solid. A27: $^1$H NMR (400 MHz, CDCl$_3$) δ 5.30-5.28 (m, 1H), 3.65 (s, 3H), 2.40-0.91 (m, 37H), 0.66 (s, 3H). LCMS Rt=1.562 min in 2 min chromatography, 10-80AB, MS ESI calcd. for C$_{27}$H$_{43}$O$_2$ [M+H−H$_2$O]$^+$ 399, found 399.

Step 10.

To a solution of LiAlH₄ (6.11 g, 161 mmol) in THF (135 mL) was added dropwise a solution of A27 (27 g, 64.8 mmol) in THF (135 mL) at 0° C. The mixture was stirred at 25° C. for 1 h. H₂O (100 mL) was added at 0° C. The reaction mixture was filtered, washed with THF (2×100 mL). The filtrate was concentrated under vacuum to give crude product, which was washed with EtOAc (100 mL) to give Compound 4 (25 g, 100%) and 30 mg of the product was recrystallized (EtOAc, 3 mL) to give Compound 4 (27 mg) as an off white solid.

Compound 4:
¹H NMR (400 MHz, CDCl₃) δ 5.31-5.29 (m, 1H), 3.70-3.60 (m, 2H), 2.43-2.40 (m, 1H), 2.20-0.90 (m, 37H), 0.67 (s, 3H). LCMS Rt=1.402 min in 2 min chromatography, 10-80AB, MS ESI calcd. for $C_{26}H_{45}O_2$ [M+H]⁺ 389, found 371 $C_{26}H_{43}O$ [M+H-H₂O].

Step 11.

To a solution of Compound 4 (18 g, 46.3 mmol) in DCM (180 mL) was added DMP (58.5 g, 138 mmol) at 0° C. The reaction was stirred at 25° C. for 1 h. The mixture was poured into saturated Na₂S₂O₃ (100 mL) at 0° C. The mixture was extracted with EtOAc (3×100 mL). The combined organic layers was washed with saturated NaHCO₃ (2×150 mL), brine (100 mL), dried over Na₂SO₄, filtered and concentrated in vacuum to give crude product, which was purified by a silica gel column (PE/EtOAc=5/1) to give A10 (13 g, 73%) as an off white solid.

¹H NMR (400 MHz, CDCl₃) δ 9.76 (t, J=1.8 Hz, 1H), 5.33-5.27 (m, 1H), 2.46-2.31 (m, 3H), 2.10-0.72 (m, 34H), 0.67 (s, 3H).

Step 12.

To a solution of A10 (10 g, 25.8 mmol) in THF (100 mL) was added MeMgBr (51 mL, 154 mmol) at 0° C. under N₂. The reaction was stirred at 25° C. for 1 h. The reaction was quenched by saturated.NH₄Cl (30 mL) and extracted with EtOAc (3×100 mL). The combined organic layers were washed with brine (50 mL), dried over Na₂SO₄, filtered and concentrated in vacuum to give crude product, which was purified by a silica gel column (PE/EtOAc=10/1) to give A11 (4.1 g, 40%) as an off white solid. ¹H NMR (400 MHz, CDCl₃) δ 5.30-5.29 (m, 1H), 3.81-3.77 (m, 1H), 2.43-2.39 (m, 1H), 1.99-0.76 (m, 40H), 0.67 (s, 3H).

Step 13.

A mixture of A11 (400 mg, 0.993 mmol) was purified by SFC separation (Column: Chiralpak AD 250×30 mm I.D., 5 μm; Mobile phase: Supercritical CO₂/MeOH+NH₃H₂O=55/45; Flow rate: 60 ml/min; Wavelength:220 nm) to give Compound 5 (Peak 1, 120 mg, 30%) as an off white solid and Compound 6 (Peak 2, 150 mg, 38%) as an off white solid.

Compound 5:
¹H NMR (400 MHz, CDCl₃) δ 5.32-5.27 (m, 1H), 3.85-3.72 (m, 1H), 2.45-2.40 (m, 1H), 2.06-1.91 (m, 3H), 1.88-1.65 (m, 3H), 1.54-1.33 (m, 12H), 1.32-0.87 (m, 22H), 0.68 (s, 3H). LCMS Rt=1.267 min in 2 min chromatography, 30-90AB, MS ESI calcd. for $C_{27}H_{47}O_2$ [M+H]⁺ 403, found $C_{27}H_{45}O$ [M-H₂O+H]⁺ 385.

Compound 6:
¹H NMR (400 MHz, CDCl₃) δ 5.33-5.27 (m, 1H), 3.84-3.75 (m, 1H), 2.45-2.40 (m, 1H), 2.06-1.92 (m, 3H), 1.89-1.64 (m, 3H), 1.56-0.79 (m, 34H), 0.67 (s, 3H). LCMS Rt=1.262 min in 2 min chromatography, 30-90AB, MS ESI calcd. for $C_{27}H_{47}O_2$ [M+H]⁺ 403, found $C_{27}H_{45}O$ [M-H₂O+H]⁺ 385.

Example 4. Synthesis of Compounds 7 and 8

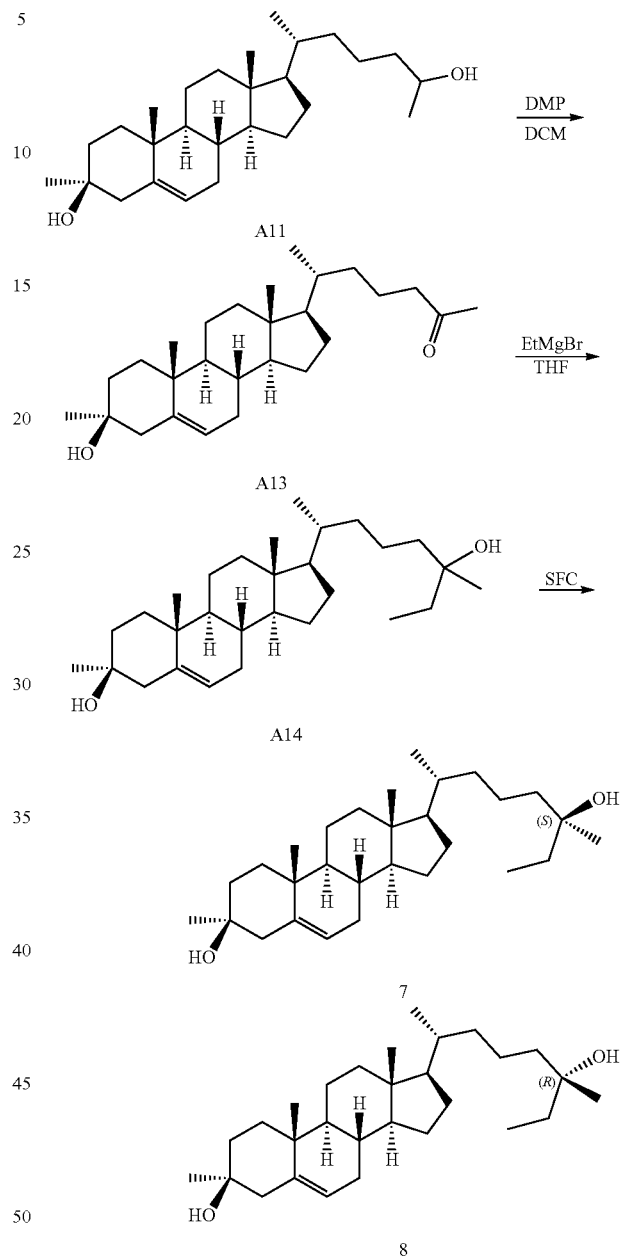

Step 1.

To a solution of A11 (3.6 g, 8.94 mmol) in DCM (40 mL) was added DMP (11.3 g, 26.8 mmol) at 0° C. The reaction was stirred at 25° C. for 1 h. The mixture was poured into saturated Na₂S₂O₃ (60 ml) at 0° C. and extracted with EtOAc (3×50 mL). The combined organic layers were washed with saturated aqueous NaHCO₃ (2×50 mL), brine (50 mL), dried over Na₂SO₄, filtered and concentrated in vacuum to give crude product, which was purified by a silica gel column (PE/EtOAc=15/1) to give A13 (1.4 g, 39%) as an off white solid. ¹H NMR (400 MHz, CDCl₃) δ 5.33-5.31 (m, 1H), 2.50-2.30 (m, 3H), 2.16 (s, 3H), 2.02-0.94 (m, 34H), 0.69 (s, 3H).

Step 2.

To a solution of A13 (288 mg, 0.718 mmol) in anhydrous THF (10 mL) at −10° C. under $N_2$ was added EtMgBr (3 M in diethyl ether, 1.43 mL, 4.30 mmol) dropwise. The mixture was stirred at 25° C. for 3 hrs. The mixture was quenched with saturated $NH_4Cl$ (10 mL), extracted with EtOAc (3×10 mL). The combined organic layer was dried over $Na_2SO_4$, filtered and concentrated. The residue was purified by silica gel column chromatography, eluting with DCM to give A14 (105 mg, 34%) as an off white solid.

Step 3.

A14 (105 mg, 0.244 mmol) was separated by SFC (Column: Chiralpak AD 250×30 mm I.D., 5 μm; Mobile phase: Supercritical $CO_2$/EtOH+$NH_3H_2O$=70/30; Flow rate: 60 ml/min; Wavelength:220 nm) to give Compound 7 (Peak 1, 21.4 mg, 28%) as an off white solid and Compound 8 (Peak 2, 12.4 mg, 16%) as an off white solid.

Compound 7:

$^1$H NMR (400 MHz, $CDCl_3$) δ 5.32-5.28 (m, 1H), 2.45-2.40 (m, 1H), 2.04-1.93 (m, 3H), 1.81-1.65 (m, 3H), 1.52-0.79 (m, 39H), 0.68 (s, 3H). LCMS Rt=1.378 min in 2 min chromatography, 30-90AB, MS ESI calcd. for $C_{29}H_{51}O_2$ [M+H]$^+$ 431, found $C_{29}H_{47}$ [M+H−2$H_2O$]$^+$ 395.

Compound 8:

$^1$H NMR (400 MHz, $CDCl_3$) δ 5.32-5.28 (m, 1H), 2.45-2.40 (m, 1H), 2.05-1.94 (m, 3H), 1.88-1.63 (m, 4H), 1.52-0.83 (m, 38H), 0.68 (s, 3H). LCMS Rt=1.374 min in 2 min chromatography, 30-90AB, MS ESI calcd. for $C_{29}H_{51}O_2$ [M+H]$^+$ 431, found $C_{29}H_{47}$ [M+H−2$H_2O$]$^+$ 395.

Example 5. Synthesis of Compounds 9 and 10

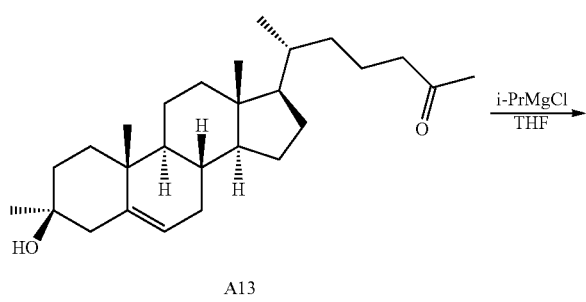

A13

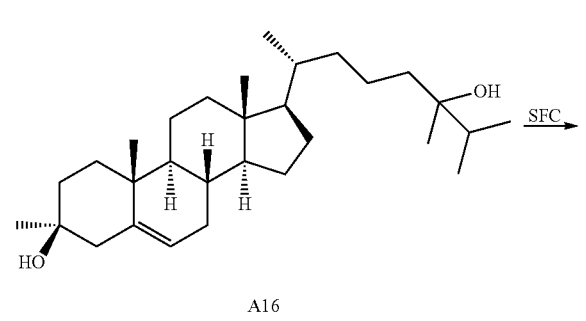

A16

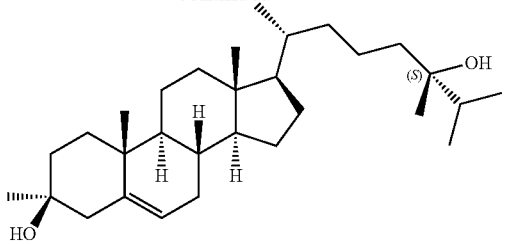

9

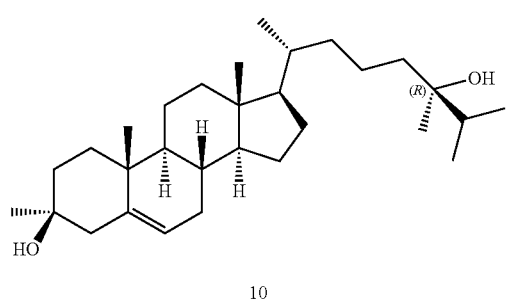

10

Step 1.

To a solution of A13 (500 mg, 1.24 mmol) in anhydrous THF (5 mL) at 0° C. under $N_2$ was added i-PrMgCl (2 M in THF, 6.2 mL, 12.3 mmol) dropwise. The reaction mixture was stirred at 25° C. for 16 hrs. The reaction mixture was cooled to 0° C., quenched with saturated $NH_4Cl$ (10 mL), extracted with EtOAc (3×10 mL). The combined organic layer was dried over $Na_2SO_4$, filtered and concentrated. The residue was purified by column chromatography on silica gel (DCM/Acetone=500/1) to give A16 (160 mg, 29%) as an off white solid.

Step 2.

A16 (100 mg, 0.224 mmol) was separated by SFC (Column: Chiralpak AD 250×30 mm I.D., 5 um; Mobile phase: Supercritical $CO_2$/EtOH+$NH_3H_2O$=65/35; Flow rate: 60 ml/min; Wavelength: 220 nm) to give Compound 9 (Peak 1, 26.2 mg, 26%) as an off white solid and Compound 10 (Peak 2, 18.8 mg, 19%) as an off white solid.

Compound 9:

$^1$H NMR (400 MHz, $CDCl_3$) δ 5.33-5.27 (m, 1H), 2.45-2.40 (m, 1H), 2.06-1.92 (m, 3H), 1.88-1.64 (m, 5H), 1.52-0.78 (m, 39H), 0.68 (s, 3H). LCMS Rt=1.444 min in 2 min chromatography, 30-90AB, MS ESI calcd. for $C_{30}H_{53}O_2$ [M+H]$^+$ 445, found $C_{30}H_{49}$ [M+H−2$H_2O$]$^+$ 409.

Compound 10:

$^1$HNMR (400 MHz, $CDCl_3$) δ 5.32-5.28 (m, 1H), 2.45-2.40 (m, 1H), 2.05-1.93 (m, 3H), 1.88-1.65 (m, 5H), 0.84-1.52 (m, 39H), 0.68 (s, 3H). LCMS Rt=1.442 min in 2 min chromatography, 30-90AB, MS ESI calcd. for $C_{30}H_{53}O_2$ [M+H]$^+$ 445, found $C_{30}H_{49}$ [M+H−2$H_2O$]$^+$ 409.

Example 6. Synthesis of Compounds 11 and 12

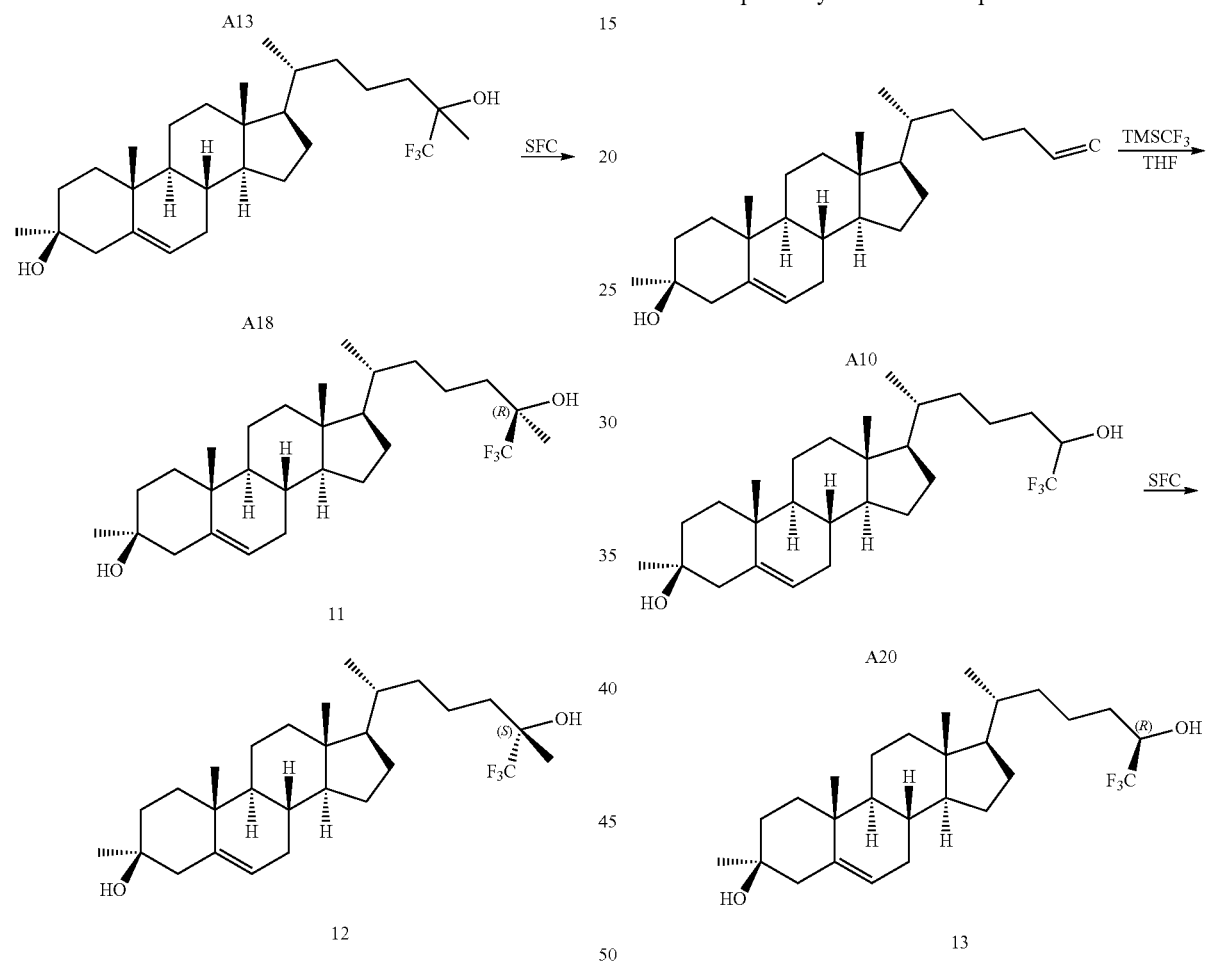

Step 1.

To a solution of A13 (300 mg, 0.748 mmol) in THF (5 mL) was added TMSCF$_3$ (106 mg, 0.748 mmol) at 25° C. The reaction was stirred at 25° C. for 1 h. TBAF (271 mg, 1.04 mmol) was added at 25° C. The reaction was poured into water, extracted with EtOAc (2×10 mL). The combined organic layers was washed with saturated NaHCO$_3$ (2×20 mL), brine (20 mL), dried over Na$_2$SO$_4$, filtered and concentrated in vacuum to give A18 (100 mg) as an off white solid. Step 2. A18 (100 mg. 212 μmol) was purified by SFC separation (Column: Chiralpak AD 250×30 mm I.D., 5 μm; Mobile phase: Supercritical CO$_2$/MeOH+NH$_3$H$_2$O=70/30; Flow rate: 60 ml/min; Wavelength:220 nm) to give Compound 11 (Peak 1, 25.6 mg, 26%) and Compound 12 (Peak 2, 30 mg, 30%) as off white solids.

Compound 11:

$^1$H NMR (400 MHz, CDCl$_3$) δ 5.33-5.28 (m, 1H), 2.45-2.40 (m, 1H), 2.06-1.93 (m, 3H), 1.90-1.61 (m, 6H), 1.56-1.38 (m, 9H), 1.35 (s, 3H), 1.32-0.82 (m, 19H), 0.68 (s, 3H). LCMS Rt=1.327 min in 2 min chromatography, 30-90 AB, MS ESI calcd. for C$_{28}$H$_{44}$F$_3$O [M–H$_2$O+H]$^+$ 453, found 453. Compound 12: $^1$H NMR (400 MHz, CDCl$_3$) δ 5.34-5.28 (m, 1H), 2.45-2.40 (m, 1H), 2.06-1.92 (m, 3H), 1.90-1.66 (m, 5H), 1.56-1.33 (m, 13H), 1.31-0.87 (m, 19H), 0.68 (s, 3H). LCMS Rt=1.320 min in 2 min chromatography, 30-90 AB, MS ESI calcd. for C$_{28}$H$_{44}$F$_3$O [M–H$_2$O+H]$^+$ 453, found 453.

Example 7. Synthesis of Compounds 13 and 14

Step 1.

To a solution A10 (400 mg, 1.03 mmol) in THF (5 mL) was added TMSCF$_3$ (365 mg, 2.57 mmol) at 25° C. The mixture was stirred at 25° C. for 1 h. TBAF (806 mg, 3.09 mmol) was added. The mixture was stirred at 25° C. for 1 h. The mixture was poured into water (30 mL), washed with saturated brine (2×20 mL), dried over $Na_2SO_4$ and concentrated in vacuum to give A20 (190 mg, 40%) as an off white solid. $^1$H NMR (400 MHz, $CDCl_3$) δ 5.33-5.28 (m, 1H), 4.00-3.85 (m, 1H), 2.50-2.35 (m, 1H), 2.11-1.93 (m, 4H), 1.89-1.61 (m, 5H), 1.53-1.35 (m, 8H), 1.31-1.05 (m, 11H), 1.01 (s, 9H), 0.68 (s, 3H). LCMS Rt=1.301 min in 2 min chromatography, 30-90 AB, MS ESI calcd. for $C_{27}H_{42}F_3O$ $[M-H_2O+H]^+$ 439, found 439.

Step 2.

A20 (190 mg, 0.416 mmol) was purified by SFC (Column: Chiralpak AD 250×30 mm I.D., 5 um; Mobile phase: Supercritical $CO_2$/MeOH+$NH_3H_2O$=65/35; Flow rate: 60 ml/min; Wavelength:220 nm) at 25° C. to give Compound 13 (Peak 1, 38.4 mg, 20%) and Compound 14 (Peak 2, 47.6 mg, 25%) as off white solids.

Compound 13:

$^1$H NMR (400 MHz, $CDCl_3$) δ 5.34-5.27 (m, 1H), 3.98-3.84 (m, 1H), 2.45-2.40 (m, 1H), 2.08-1.92 (m, 4H), 1.89-1.64 (m, 6H), 1.53-1.36 (m, 7H), 1.33-1.21 (m, 3H), 1.21-1.08 (m, 7H), 1.07-0.90 (m, 10H), 0.68 (s, 3H). LCMS Rt=1.302 min in 2 min chromatography, 30-90 AB, MS ESI calcd. for $C_{27}H_{44}F_3O_2$ $[M+H]^+$ 457, found $C_{27}H_{42}F_3O$ $[M+H-H_2O]^+$ 439. Compound 14: $^1$H NMR (400 MHz, $CDCl_3$) δ 5.34-5.28 (m, 1H), 3.95-3.89 (m, 1H), 2.45-2.40 (m, 1H), 2.06-1.92 (m, 4H), 1.89-1.59 (m, 7H), 1.54-1.34 (m, 8H), 1.32-1.21 (m, 2H), 1.20-1.05 (m, 8H), 1.04-0.90 (m, 8H), 0.68 (s, 3H). LCMS Rt=1.299 min in 2 min chromatography, 30-90 AB, MS ESI calcd. for $C_{27}H_{44}F_3O_2$ $[M+H]^+$ 457, found $C_{27}H_{42}F_3O$ $[M+H-H_2O]^+$ 439.

Example 8. Synthesis of Compound 17

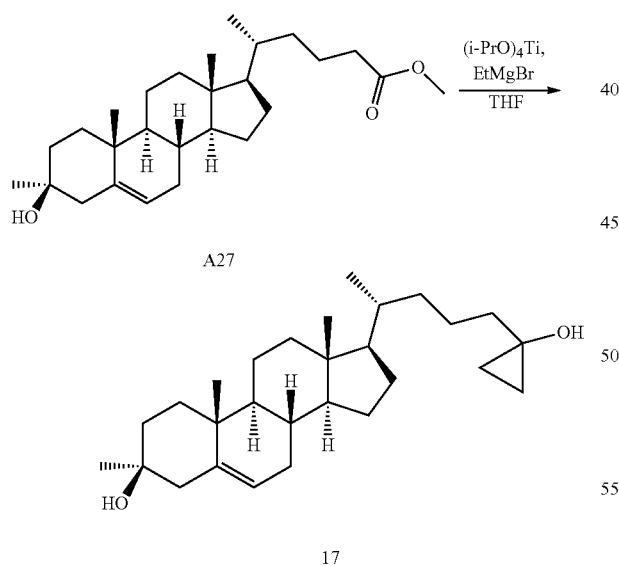

Step 1.

To a solution of A27 (500 mg, 1.20 mmol) and (i-PrO)$_4$Ti (341 mg, 1.20 mmol) in anhydrous THF (10 mL) under $N_2$ at 25° C. was added EtMgBr (3 M in diethyl ether, 1.39 mL, 4.19 mmol) dropwise. The mixture was stirred at 25° C. for 16 hrs. The reaction mixture was quenched with brine (15 mL), diluted with EtOAc (20 mL), filtered through a pad of Celite and the filtrate was extracted with EtOAc (2×20 mL). The combined organic layer was dried over anhydrous $Na_2SO_4$, filtered and concentrated. The residue was purified by column chromatography on silica gel (PE/EtOAc=20/1) to give Compound 17 (220 mg, 44%) as an off white solid. $^1$H NMR (400 MHz, $CDCl_3$) δ 5.33-5.27 (m, 1H), 2.50-2.40 (m, 1H), 2.06-1.92 (m, 3H), 1.88-1.63 (m, 5H), 1.54-1.34 (m, 10H), 1.29-0.90 (m, 19H), 0.76-0.65 (m, 5H), 0.47-0.40 (m, 2H). LCMS Rt=1.294 min in 2 min chromatography, 30-90AB, MS ESI calcd. for $C_{28}H_{47}O_2$ $[M+H]^+$ 415, found $C_{28}H_{45}O$ $[M+H-H_2O]^+$ 397.

Example 9. Synthesis of Compounds 18, 19, and 20

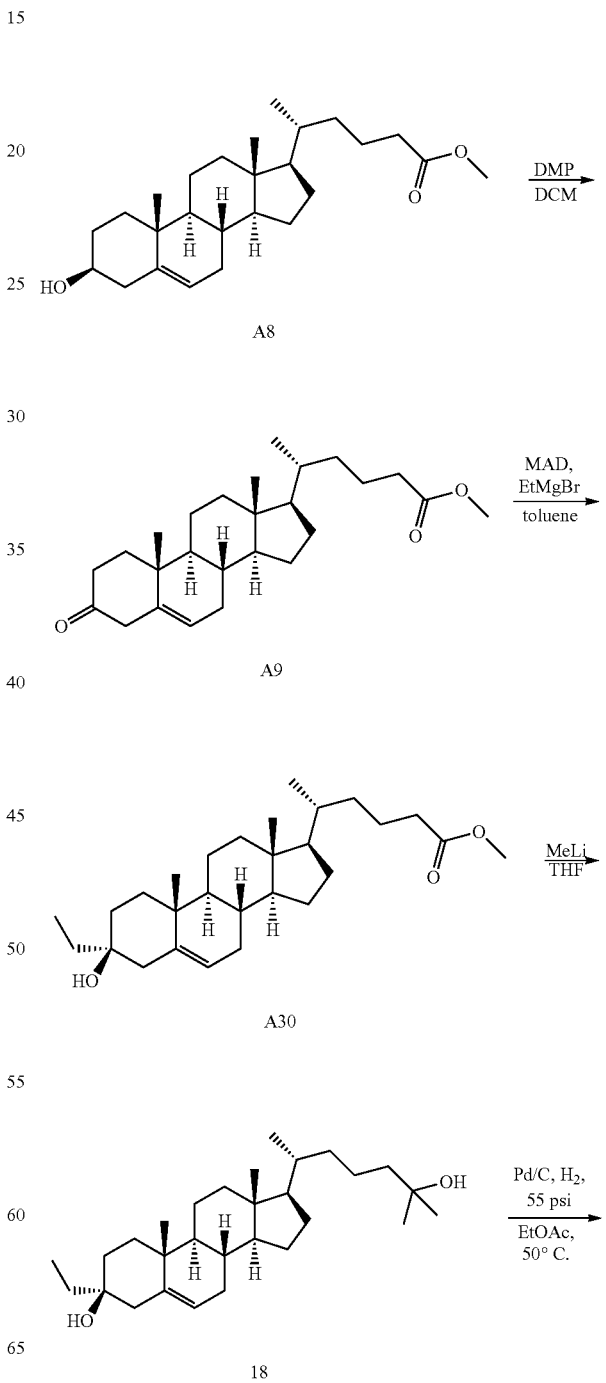

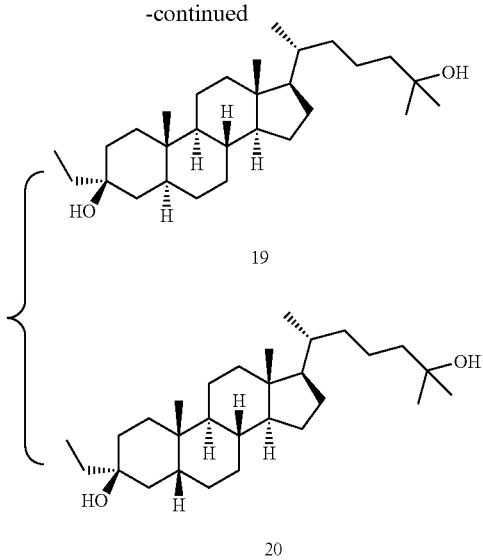

Step 1.

To a solution of A8 (1.4 g, 3.47 mmol) in DCM (20 mL) was added DMP (2.94 g, 6.94 mmol) at 25° C. The mixture was stirred at 25° C. for 2 hrs. The mixture was poured into saturated $Na_2S_2O_3$ (100 ml) at 0° C. and extracted with EtOAc (2×100 mL). The combined organic layers was washed with saturated $NaHCO_3$ (2×80 mL), brine (100 mL), dried over $Na_2SO_4$ and concentrated in vacuum to give A9 (1.5 g, crude) as an off white solid.

Step 2.

To a solution of BHT (4.93 g, 22.4 mmol) in toluene (20 mL) was added $AlMe_3$ (5.60 mL, 2 M in toluene, 11.2 mmol) dropwise at 0° C. The reaction mixture was stirred at 25° C. for 1.5 hrs. A solution of A9 (1.5 g, 3.74 mmol) in toluene (20 mL) was added at −70° C. The resulting mixture was stirred at −70° C. for 1 hour. EtMgBr (3.73 mL, 3.0 M in diethyl ether, 11.2 mmol) at −70° C. was added. The reaction mixture was stirred at −70° C. for another 1 hour. The reaction was quenched with $NH_4Cl$ (100 mL), extracted with EtOAc (2×100 mL). The combined organic layers were washed with brine (100 mL). The organic layer was dried over $Na_2SO_4$, filtered and concentrated under reduced pressure to give crude product, which was purified by silica gel chromatography eluted with PE/EtOAc=10/1 to give A30 (600 mg, 35%) as white solid. $^1$H NMR (400 MHz, $CDCl_3$) δ 5.31-5.26 (m, 1H), 3.67 (s, 3H), 2.41-2.19 (m, 3H), 2.07-1.91 (m, 3H), 1.88-1.61 (m, 5H), 1.55-1.33 (m, 11H), 1.31-1.01 (m, 10H), 1.00-0.80 (m, 7H), 0.67 (s, 3H).

Step 3.

To a solution of A30 (550 mg, 1.27 mmol) in THF (5 mL) was added MeLi (3.17 mL, 5.08 mmol) at −70° C. The mixture was stirred at −70° C. for 10 mins. The reaction was quenched with saturated $NH_4Cl$ (20 mL), extracted with EtOAc (2×20 mL). The combined organic layers were washed with brine (30 mL), dried over $Na_2SO_4$, filtered and concentrated under reduced pressure. This mixture was combined with another batch synthesized from 50 mg of the starting material. The residue was purified by silica gel chromatography (PE/EtOAc=10/1) to give Compound 18 (270 mg, 49% yield) as white solid. $^1$H NMR (400 MHz, $CDCl_3$) δ 5.28 (d, J=5.0 Hz, 1H), 2.36 (d, J=13.1 Hz, 1H), 2.08-1.91 (m, 3H), 1.89-1.69 (m, 3H), 1.65-1.60 (m, 3H), 1.51-1.32 (m, 8H), 1.30-1.17 (m, 11H), 1.15-1.01 (m, 8H), 0.99-0.81 (m, 9H), 0.68 (s, 3H). LCMS Rt=1.372 min in 2 min chromatography, 30-90 AB, MS ESI calcd. for $C_{29}H_{51}O_2$ [M+H]$^+$ 431, found $C_{29}H_{47}$ [M+H−2H$_2$O]$^+$ 395.

Step 4.

To a solution of Compound 18 (200 mg, 0.464 mmol) in EtOAc (10 mL) was added Pd/C (100 mg) at 25° C. The mixture was stirred under $H_2$ at 55° C. for 12 hrs. The reaction mixture was filtered and the filtered cake was washed with EtOAc (2×40 mL). The mixture was concentrated under reduced pressure to give crude product, which was purified by silica gel chromatography eluted with PE/EtOAc=10/1 to give Compound 19 (6.6 mg) and Compound 20 (10.2 mg) as off white solids.

Compound 19:

$^1$H NMR (400 MHz, $CDCl_3$) δ 2.02-1.95 (m, 1H), 1.94-1.72 (m, 4H), 1.52-1.31 (m, 14H), 1.27-1.16 (m, 14H), 1.14-0.99 (m, 7H), 0.97 (s, 3H), 0.95-0.89 (m, 6H), 0.65 (s, 3H). LCMS Rt=1.432 min in 2 min chromatography, 30-90 AB, MS ESI calcd. for $C_{29}H_{53}O_2$ [M+H]$^+$ 433, found $C_{29}H_{49}$ [M+H−2H$_2$O]$^+$ 397.

Compound 20:

$^1$H NMR (400 MHz, $CDCl_3$) δ 1.96 (d, J=12.5 Hz, 1H), 1.86-1.75 (m, 1H), 1.58-1.50 (m, 5H), 1.49-1.29 (m, 10H), 1.21 (s, 13H), 1.13-0.95 (m, 8H), 0.94-0.84 (m, 7H), 0.82 (s, 3H), 0.64 (s, 4H). LCMS Rt=1.431 min in 2 min chromatography, 30-90 AB, MS ESI calcd. for $C_{29}H_{53}O_2$ [M+H]$^+$ 433, found $C_{29}H_{49}$ [M+H−2H$_2$O]$^+$ 397.

Example 10. Synthesis of Compound 22

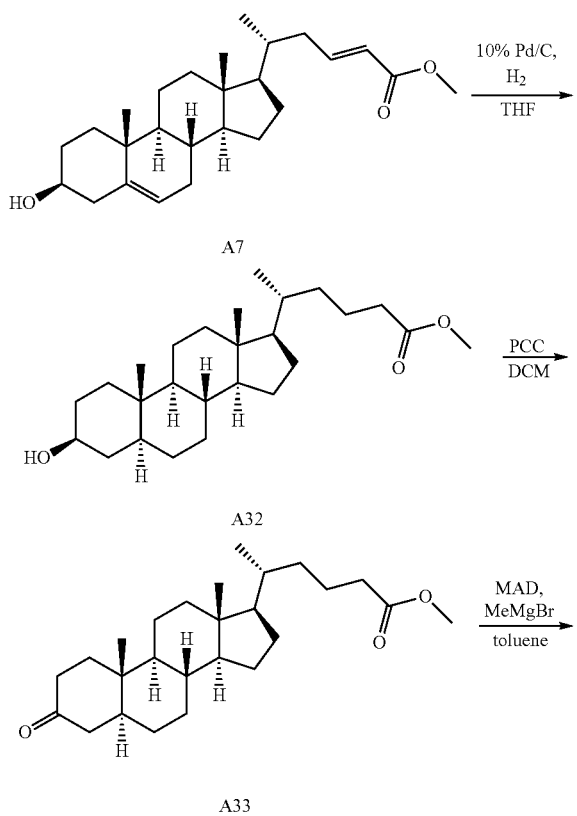

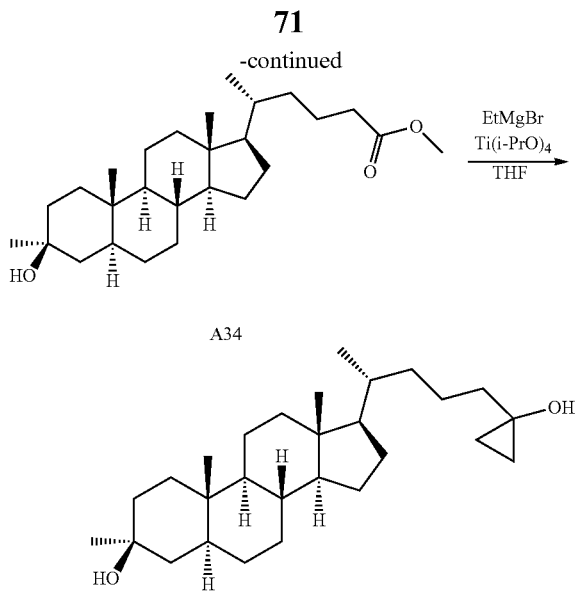

Step 4.

To a solution of A34 (300 mg, 0.716 mmol) and Ti(i-PrO)$_4$ (203 mg, 0.716 mmol) in THF (10 ml) was added EtMgBr (3 M in diethyl ether, 713 μL, 2.14 mmol). The mixture was stirred at 25° C. for 16 hours. The reaction mixture was quenched with saturated NH$_4$Cl (5 mL). The mixture was filtered through a pad of celite. The filtrate was extracted with EtOAc (2×20 mL). The combined organic layer was dried over Na$_2$SO$_4$, filtered and concentrated. The residue was purified by column chromatography on silica gel (PE/EtOAc=20/1-10/1) to give Compound 22 (77 mg, 26%) as an off white solid. $^1$H NMR (400 MHz, CDCl$_3$) δ 2.00-1.92 (m, 1H), 1.84-1.61 (m, 6H), 1.53-0.83 (m, 30H), 0.80 (s, 3H), 0.76-0.71 (m, 2H), 0.69-0.60 (m, 4H), 0.47-0.40 (m, 2H). LCMS Rt=1.317 min in 2 min chromatography, 30-90AB, MS ESI calcd. for C$_{28}$H$_{49}$O$_2$ [M+H]$^+$ 417, found C$_{28}$H$_{47}$O [M+H-H$_2$O]$^+$ 399.

Example 11. Synthesis of Compounds 23 and 24

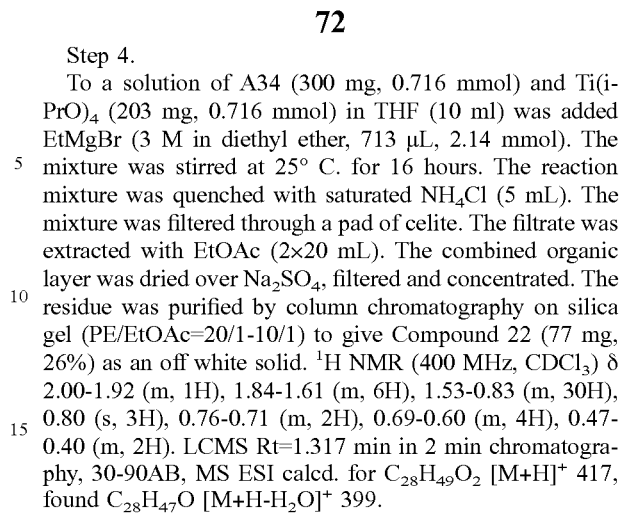

Step 1.

To a solution of A7 (3 g, 7.48 mmol) in THF (30 mL) was added Pd/C (10%, 600 mg).

The mixture was degassed and purged with H$_2$ three times. The resulting mixture was stirred at 25° C. under H$_2$ for 16 hrs. The reaction mixture was filtered through a pad of Celite, and the filtrate was concentrated to give A32 (3 g, 99%) as an off white solid. $^1$H NMR (400 MHz, CDCl$_3$) δ3.66 (s, 3H), 3.63-3.53 (m, 1H), 2.34-2.18 (m, 2H), 1.99-1.91 (m, 1H), 1.82-1.62 (m, 5H), 1.56-1.43 (m, 3H), 1.42-1.18 (m, 10H), 1.14-0.77 (m, 15H), 0.68-0.57 (m, 4H).

Step 2.

To a solution of A32 (3 g, 7.41 mmol) in DCM (30 mL) was added PCC (3.19 g, 14.8 mmol) and silica gel (4 g, 66.6 mmol) at 25° C. The mixture was stirred at 25° C. for 1.5 hrs. The mixture was filtered. The filtrate was concentrated in vacuum, purified by column chromatography on silica gel (PE/EtOAc=50/1 to 10/1) to give A33 (2.4 g) as an off white solid. $^1$H NMR (400 MHz, CDCl$_3$) δ 3.66 (s, 3H), 2.44-2.19 (m, 5H), 2.13-1.94 (m, 3H), 1.89-1.64 (m, 3H), 1.53-0.82 (m, 24H), 0.76-0.66 (m, 4H).

Step 3.

To a solution of BHT (7.88 g, 35.7 mmol) in toluene (25 mL) was added AlMe$_3$ (8.9 mL, 17.8 mmol, 2 M in toluene) at 0° C. under N$_2$. The mixture was stirred at 25° C. for 1 h. A solution of A33 (2.4 g, 5.96 mmol) in toluene (5 mL) at −70° C. was added. The mixture was stirred at −78° C. for 1 h. MeMgBr (5.93 mL, 17.8 mmol, 3M in diethyl ether) was added at −78° C. The mixture was stirred at −78° C. for 1 h. The reaction mixture was quenched with saturated citric acid (100 mL). The mixture was extracted with EtOAc (3×100 mL), washed with brine (3×300 mL), dried over Na$_2$SO$_4$, concentrated in vacuum to give a crude product, which was purified by column chromatography on silica gel (PE/EtOAc=30/1 to 10/1) to give A34 (2 g) as a yellow solid. A34: $^1$H NMR (400 MHz, CDCl$_3$) δ 3.67 (s, 3H), 2.36-2.18 (m, 2H), 2.01-1.92 (m, 1H), 1.86-1.77 (m, 1H), 1.72-1.61 (m, 3H), 1.55-1.46 (m, 4H), 1.40-1.21 (m, 13H), 1.18-0.99 (m, 7H), 0.95-0.86 (m, 5H), 0.81 (s, 3H), 0.70-0.60 (m, 4H). LCMS Rt=1.372 min in 2 min chromatography, 30-90 AB, MS ESI calcd. for C$_{27}$H$_{47}$O$_2$ [M+H]$^+$ 418.3, found 401 [M+H-H$_2$O]$^+$.

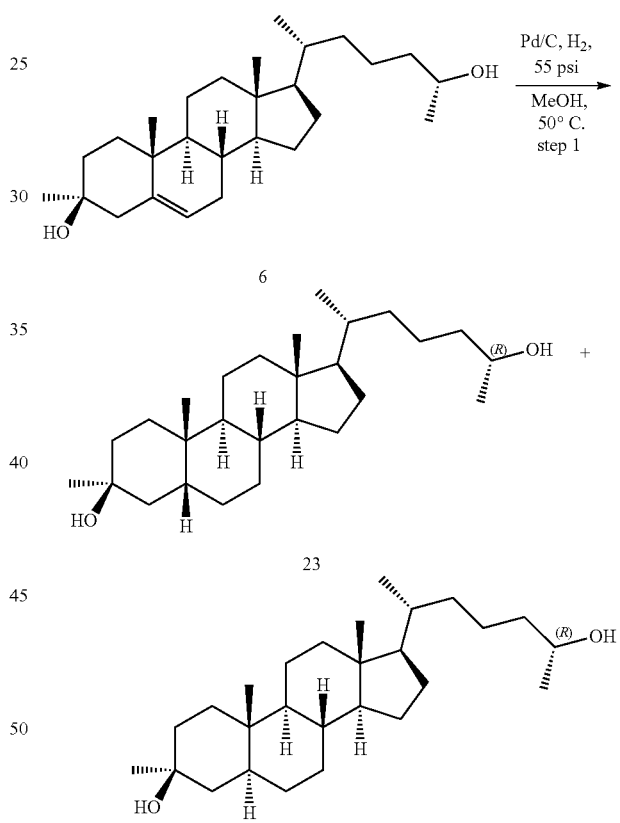

Step 1.

To a solution of Compound 6 (50 mg, 0.124 mmol) in MeOH (10 mL) was added Pd/C (10% wt, 26.6 mg, 24.8 mmol). After degassing for three times with H$_2$, the reaction mixture was stirred for 72 hrs at 50° C. under H$_2$ (55 Psi). The reaction was filtered and the filtrate was concentrated to give crude product, which was purified by a silica gel column (PE/EtOAc=15/1) to give Compound 23 (10 mg, 20%) as white solid and Compound 24 (10 mg, 20%) as white solid. Compound 23: $^1$HNMR (400 MHz, CDCl$_3$) δ 3.81-3.75 (m, 1H), 1.96-0.90 (m, 38H), 0.92 (s, 3H), 0.90 (d, J=6.4 Hz, 3H), 0.64 (s, 3H). LCMS Rt=1.293 min in 2.0 min chromatography, 30-90 AB, MS ESI calcd. for $C_{27}H_{49}O_2$ [M+H]$^+$ 405, found $C_{27}H_{45}$ [M−2H$_2$O+H]$^+$ 369.

Compound 24:

$^1$HNMR (400 MHz, CDCl$_3$) δ 3.80-3.75 (m, 1H), 2.00-1.90 (m, 1H), 1.90-1.75 (m, 1H), 1.75-0.70 (m, 38H), 0.80 (s, 3H), 0.70-0.60 (m, 4H). LCMS Rt=1.282 min in 2.0 min chromatography, 30-90 AB, MS ESI calcd. for $C_{27}H_{49}O_2$ [M+H]$^+$ 405, found $C_{27}H_{45}$ [M−2H$_2$O+H]$^+$ 369.

Example 12. Synthesis of Compounds 25 and 26

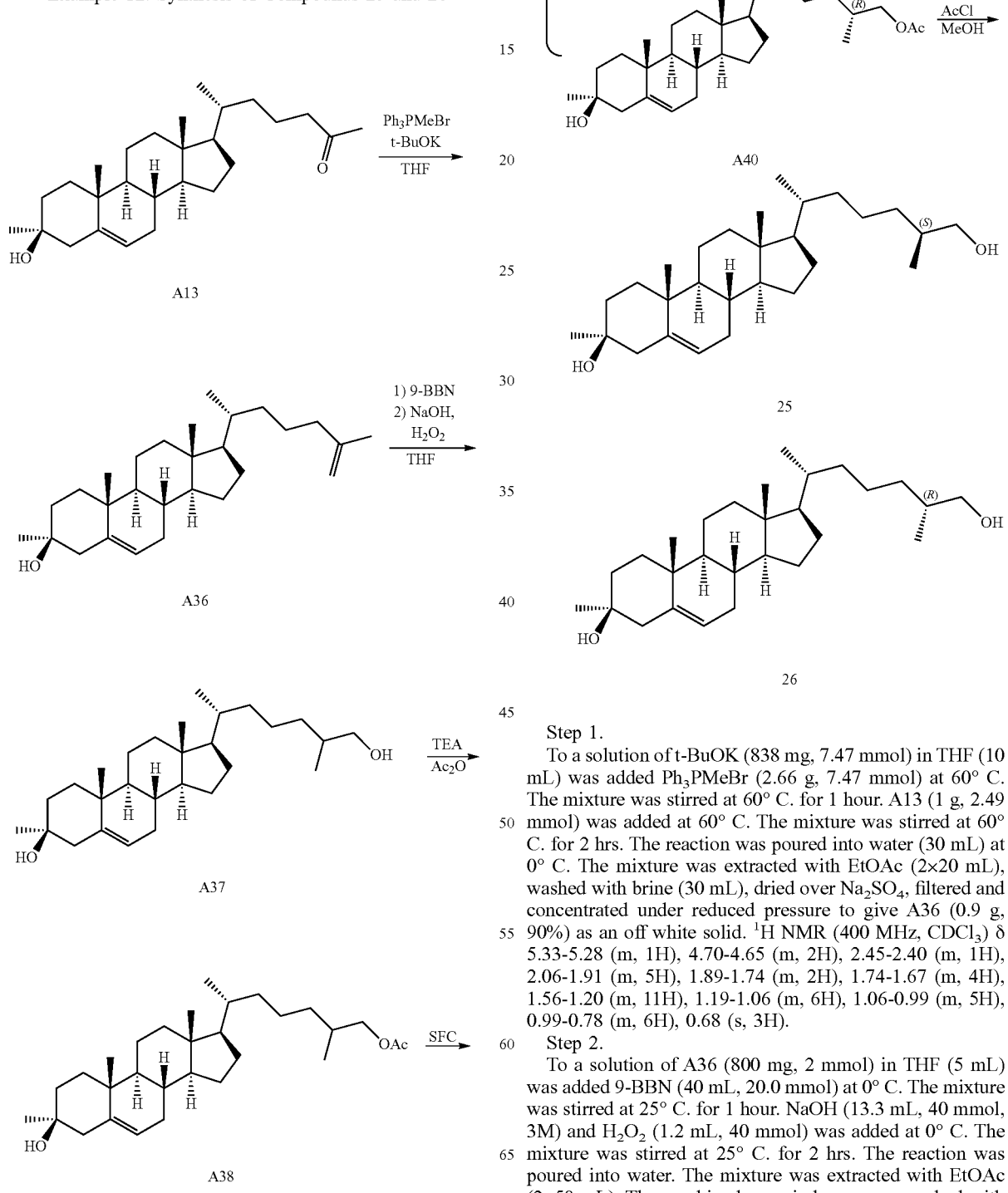

Step 1.

To a solution of t-BuOK (838 mg, 7.47 mmol) in THF (10 mL) was added Ph$_3$PMeBr (2.66 g, 7.47 mmol) at 60° C. The mixture was stirred at 60° C. for 1 hour. A13 (1 g, 2.49 mmol) was added at 60° C. The mixture was stirred at 60° C. for 2 hrs. The reaction was poured into water (30 mL) at 0° C. The mixture was extracted with EtOAc (2×20 mL), washed with brine (30 mL), dried over Na$_2$SO$_4$, filtered and concentrated under reduced pressure to give A36 (0.9 g, 90%) as an off white solid. $^1$H NMR (400 MHz, CDCl$_3$) δ 5.33-5.28 (m, 1H), 4.70-4.65 (m, 2H), 2.45-2.40 (m, 1H), 2.06-1.91 (m, 5H), 1.89-1.74 (m, 2H), 1.74-1.67 (m, 4H), 1.56-1.20 (m, 11H), 1.19-1.06 (m, 6H), 1.06-0.99 (m, 5H), 0.99-0.78 (m, 6H), 0.68 (s, 3H).

Step 2.

To a solution of A36 (800 mg, 2 mmol) in THF (5 mL) was added 9-BBN (40 mL, 20.0 mmol) at 0° C. The mixture was stirred at 25° C. for 1 hour. NaOH (13.3 mL, 40 mmol, 3M) and H$_2$O$_2$ (1.2 mL, 40 mmol) was added at 0° C. The mixture was stirred at 25° C. for 2 hrs. The reaction was poured into water. The mixture was extracted with EtOAc (2×50 mL). The combined organic layers was washed with saturated Na₂S₂O₃ (2×50 mL), brine (50 mL), dried over Na₂SO₄, filtered and concentrated in vacuum to give A37 (400 mg) as an off white solid.

$^1$H NMR (400 MHz, CDCl₃) δ 5.35-5.27 (m, 1H), 4.00-3.90 (m, 1H), 3.90-3.80 (m, 1H), 2.45-2.40 (m, 1H), 2.04-1.91 (m, 3H), 1.88-1.66 (m, 5H), 1.53-1.21 (m, 10H), 1.20-0.87 (m, 23H), 0.68 (s, 3H). Step 3. To a solution of A37 (500 mg, 1.19 mmol) in DCM (10 mL) was added TEA (240 mg, 2.38 mmol) and Ac₂O (181 mg, 1.78 mmol) at 25° C. The reaction was stirred at 25° C. for 2 hrs. The reaction was quenched by saturated NaHCO₃ (10 mL). The mixture was extracted with DCM (2×10 mL) washed with brine (2×10 mL), dried over Na₂SO₄, and concentrated to give A38 (450 mg, 82%) as an off white solid. $^1$H NMR (400 MHz, CDCl₃) δ 5.35-5.25 (m, 1H), 3.56-3.38 (m, 2H), 2.45-2.40 (m, 1H), 2.07-1.91 (m, 3H), 1.89-1.67 (m, 3H), 1.65-1.53 (m, 5H), 1.49-1.32 (m, 8H), 1.32-1.09 (m, 10H), 1.09-0.97 (m, 7H), 0.97-0.87 (m, 7H), 0.68 (s, 3H).

Step 4.

A38 (450 mg) was purified by SFC (Column: Chiralpak AD 250×30 mm I.D., 5 μm; Mobile phase: Supercritical CO₂/MeOH+NH₃H₂O=60/40; Flow rate: 60 ml/min; Wavelength:220 nm) to give A39 (200 mg) and A40 (150 mg) as off white solids.

Step 5.

To a solution of A39 (200 mg, 0.435 mmol) in MeOH (10 mL) was added AcCl (17.0 mg, 0.217 mmol) at 25° C. The mixture was stirred at 25° C. for 2 hrs. The reaction was poured into water (10 mL), extracted with THF (2×20 mL). The organic layer was washed with brine (30 mL), dried over Na₂SO₄ and concentrated to give Compound 25 (100 mg, 55%) as an off white solid. $^1$H NMR (400 MHz, CDCl₃) δ 5.33-5.28 (m, 1H), 3.57-3.36 (m, 2H), 2.46-2.38 (m, 1H), 2.05-1.92 (m, 3H), 1.87-1.57 (m, 6H), 1.52-1.34 (m, 7H), 1.28-1.20 (m, 3H), 1.18-0.89 (m, 22H), 0.68 (s, 3H). LCMS Rt=1.328 min in 2 min chromatography, 30-90 AB_E, MS ESI calcd. for C₂₈H₄₉O₂ [M+H]⁺ 417, found C₂₈H₄₇O [M+H-H₂O]⁺ 399.

Step 6.

To a solution of A40 (150 mg, 0.326 mmol) in MeOH (10 mL) was added AcCl (12.7 mg, 0.163 mmol) at 25° C. The mixture was stirred at 25° C. for 2 hrs. The reaction was poured into water (10 mL), extracted with THF (2×20 mL). The organic layer was washed with brine (30 mL), dried over Na₂SO₄ and concentrated to give crude product, which was purified by column chromatography on silica gel (PE/EtOAc=20/1 to 8/1) to give Compound 26 (90 mg, 66%) as an off white solid. $^1$H NMR (400 MHz, CDCl₃) δ 5.33-5.28 (m, 1H), 3.55-3.38 (m, 2H), 2.46-2.38 (m, 1H), 2.05-1.93 (m, 3H), 1.87-1.58 (m, 5H), 1.51-0.89 (m, 33H), 0.68 (s, 3H). LCMS Rt=1.320 min in 2 min chromatography, 30-90 AB_E, MS ESI calcd. for C₂₈H₄₉O₂ [M+H]⁺ 417, found C₂₈H₄₇O [M+H-H₂O]⁺ 399.

Example 13. Synthesis of Compound 33

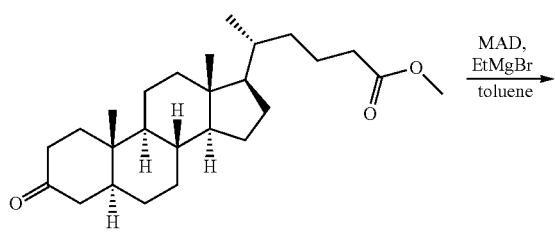

-continued

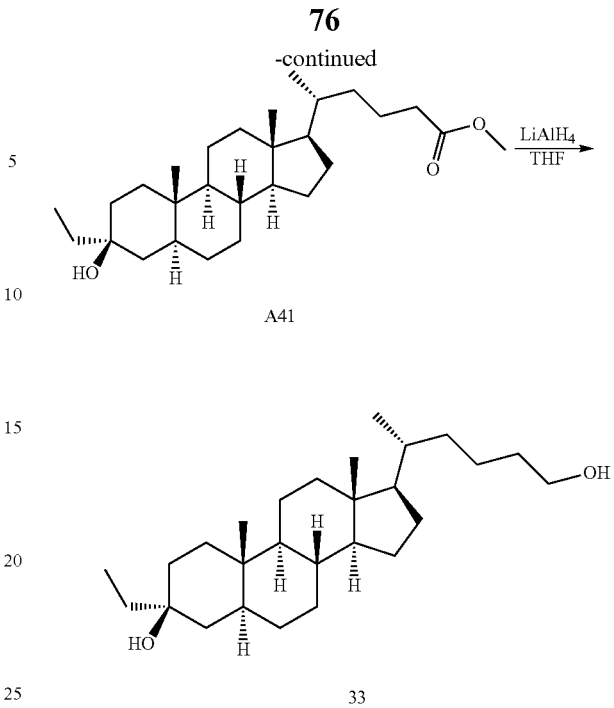

Step 1.

To a solution of BHT (32.6 g, 148 mmol) in toluene (100 mL) was added trimethylaluminum (37.2 mL, 2 M in toluene, 74.4 mmol) dropwise at 0° C. The reaction mixture was stirred at 15° C. for 1.5 hrs. A33 (10 g, 24.8 mL) in toluene (100 mL) was added dropwise at −70° C. The resulting mixture was stirred at −70° C. for 1 h. EtMgBr (28.4 mL, 3.0 M in diethyl ether, 74.4 mmol) was added dropwise at −70° C. The reaction mixture was stirred at −70° C. for another 1 h. The reaction mixture was poured into saturated aqueous critic acid (2 L). The aqueous extracted with EtOAc (3×1.5 L). The combined organic was washed with brine (2 L), dried over Na₂SO₄, filtered and concentrated under vacuum to give crude product, which was purified by silica gel chromatography eluted with PE:EtOAc=10:1 to give A41 (8 g, 75%) as a yellow solid. $^1$H NMR (400 MHz, CDCl₃) δ 3.66 (s, 3H), 2.30-2.15 (m, 2H), 2.00-1.90 (m, 1H), 1.85-1.60 (m, 5H), 1.50-1.15 (m, 15H), 1.14-0.80 (m, 18H), 0.69-0.55 (m, 4H). LCMS Rt=1.376 min in 2.0 min chromatography, 30-90 AB, purity 100%, MS ESI calcd. for C₂₈H₄₇O₂ [M+H—H₂O]⁺ 415, found 415.

Step 2.

To a solution of A41 (2 g, 4.62 mmol) in THF (50 mL) under N₂ at 0° C. was added LiAlH₄ (263 mg, 6.93 mmol) in portions. The reaction was stirred at 0° C. for 30 mins. The reaction was quenched with 1 M HCl (30 mL) at 0° C., extracted with EtOAc (3×30 mL). The combined organic phase was washed with brine (100 mL), dried over Na₂SO₄, filtered and concentrated to give crude Compound 33 (1.3 g, 70%) as an off white solid. 100 mg of crude Compound 33 was recrystallized from MeCN/DCM (10 mL/10 mL) to afford Compound 33 (30 mg) as an off white solid. $^1$H NMR (400 MHz, CDCl₃) δ 3.68-3.60 (m, 2H), 2.00-1.91 (m, 1H), 1.86-1.74 (m, 1H), 1.70-1.58 (m, 4H), 1.56-1.44 (m, 6H), 1.42-1.31 (m, 6H), 1.30-1.18 (m, 7H), 1.14-0.95 (m, 7H), 0.93-0.81 (m, 9H), 0.93-0.79 (m, 1H), 0.68-0.58 (m, 4H). LCMS Rt=1.279 min in 2.0 min chromatography, 30-90 AB, MS ESI calcd. for C₂₇H₄₇O [M+H-H₂O]⁺ 387, found 387.

Example 14. Synthesis of Compounds 34, 35, and 36

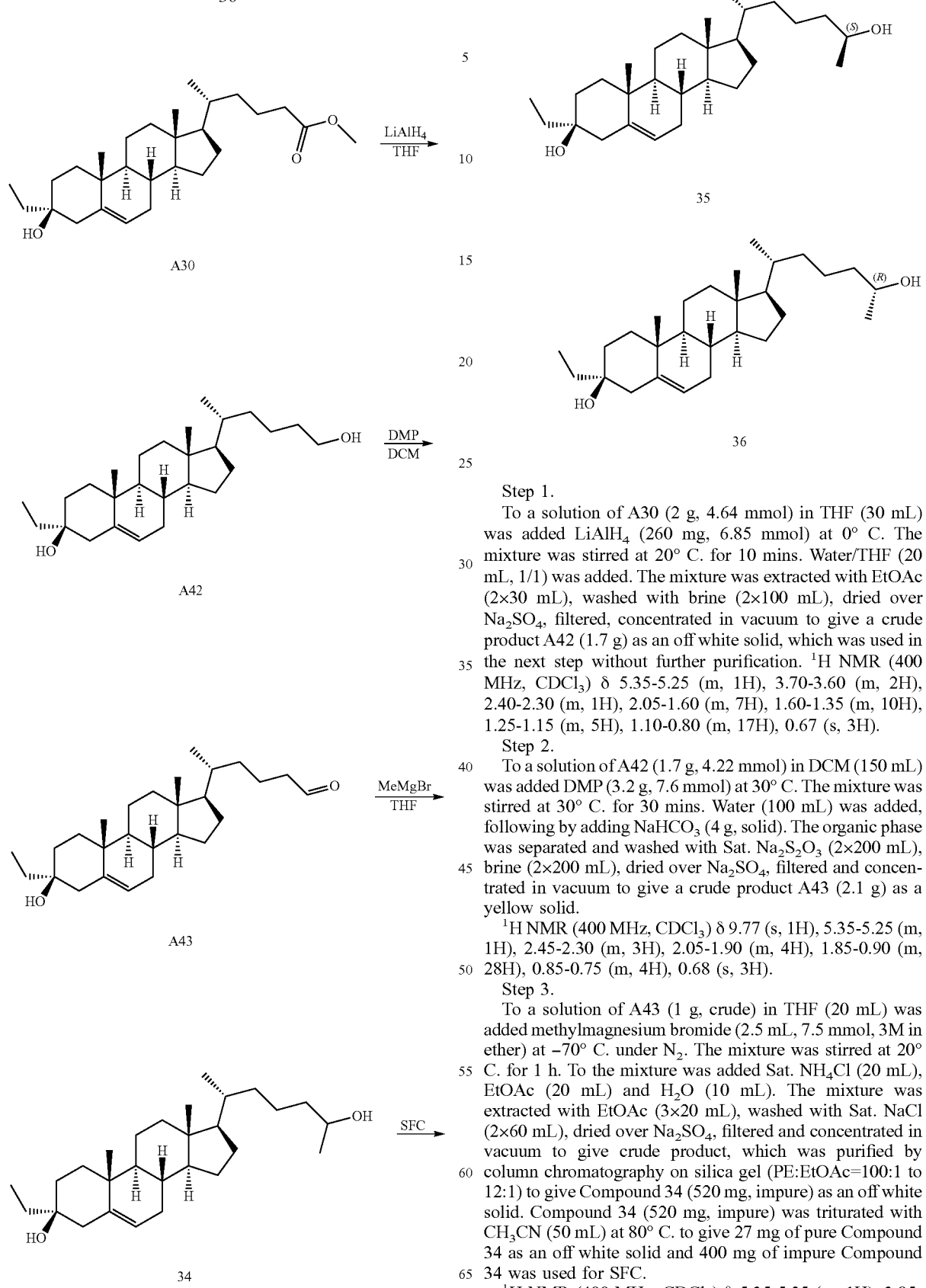

Step 1.

To a solution of A30 (2 g, 4.64 mmol) in THF (30 mL) was added LiAlH$_4$ (260 mg, 6.85 mmol) at 0° C. The mixture was stirred at 20° C. for 10 mins. Water/THF (20 mL, 1/1) was added. The mixture was extracted with EtOAc (2×30 mL), washed with brine (2×100 mL), dried over Na$_2$SO$_4$, filtered, concentrated in vacuum to give a crude product A42 (1.7 g) as an off white solid, which was used in the next step without further purification. $^1$H NMR (400 MHz, CDCl$_3$) δ 5.35-5.25 (m, 1H), 3.70-3.60 (m, 2H), 2.40-2.30 (m, 1H), 2.05-1.60 (m, 7H), 1.60-1.35 (m, 10H), 1.25-1.15 (m, 5H), 1.10-0.80 (m, 17H), 0.67 (s, 3H).

Step 2.

To a solution of A42 (1.7 g, 4.22 mmol) in DCM (150 mL) was added DMP (3.2 g, 7.6 mmol) at 30° C. The mixture was stirred at 30° C. for 30 mins. Water (100 mL) was added, following by adding NaHCO$_3$ (4 g, solid). The organic phase was separated and washed with Sat. Na$_2$S$_2$O$_3$ (2×200 mL), brine (2×200 mL), dried over Na$_2$SO$_4$, filtered and concentrated in vacuum to give a crude product A43 (2.1 g) as a yellow solid.

$^1$H NMR (400 MHz, CDCl$_3$) δ 9.77 (s, 1H), 5.35-5.25 (m, 1H), 2.45-2.30 (m, 3H), 2.05-1.90 (m, 4H), 1.85-0.90 (m, 28H), 0.85-0.75 (m, 4H), 0.68 (s, 3H).

Step 3.

To a solution of A43 (1 g, crude) in THF (20 mL) was added methylmagnesium bromide (2.5 mL, 7.5 mmol, 3M in ether) at −70° C. under N$_2$. The mixture was stirred at 20° C. for 1 h. To the mixture was added Sat. NH$_4$Cl (20 mL), EtOAc (20 mL) and H$_2$O (10 mL). The mixture was extracted with EtOAc (3×20 mL), washed with Sat. NaCl (2×60 mL), dried over Na$_2$SO$_4$, filtered and concentrated in vacuum to give crude product, which was purified by column chromatography on silica gel (PE:EtOAc=100:1 to 12:1) to give Compound 34 (520 mg, impure) as an off white solid. Compound 34 (520 mg, impure) was triturated with CH$_3$CN (50 mL) at 80° C. to give 27 mg of pure Compound 34 as an off white solid and 400 mg of impure Compound 34 was used for SFC.

$^1$H NMR (400 MHz, CDCl$_3$) δ 5.35-5.25 (m, 1H), 3.85-3.75 (m, 1H), 2.40-2.30 (m, 1H), 2.05-1.90 (m, 3H), 1.85-

1.55 (m, 6H), 1.55-1.30 (m, 10H), 1.25-0.90 (m, 20H), 0.85-0.75 (m, 3H), 0.67 (s, 3H). LCMS R$_t$=1.295 min in 2 min chromatography, 30-90AB_E, MS ESI calcd. for C$_{28}$H$_{47}$O [M−H$_2$O+H]$^+$ 399, found 399.

Step 3.

Compound 35 (400 mg, impure) was purified by SFC (Column: AD (250 mm*30 mm, 5 um); Condition: 0.1% NH$_3$H$_2$O MeOH, 40% B; FlowRate(ml/min): 60) to give Compound 35 (79 mg) and Compound 36 (59 mg) as an off white solid.

Compound 35:

$^1$H NMR (400 MHz, CDCl$_3$) δ 5.30-5.25 (m, 1H), 3.85-3.75 (m, 1H), 2.40-2.30 (m, 1H), 2.10-1.95 (m, 3H), 1.90-1.60 (m, 4H), 1.45-1.28 (m, 11H), 1.25-0.90 (m, 17H), 0.88-0.82 (m, 4H), 0.78 (t, J=7.2 Hz, 3H), 0.67 (s, 3H). LCMS R$_t$=1.295 min in 2 min chromatography, 30-90AB_E, MS ESI calcd. for [M−H$_2$O+H]$^+$ 399, found 399.

Compound 36:

$^1$H NMR (400 MHz, CDCl$_3$) δ 5.30-5.25 (m, 1H), 3.85-3.75 (m, 1H), 2.40-2.30 (m, 1H), 2.10-1.95 (m, 3H), 1.90-1.60 (m, 4H), 1.50-1.17 (m, 11H), 1.14-0.90 (m, 17H), 0.88-0.82 (m, 4H), 0.78 (t, J=7.2 Hz, 3H), 0.67 (s, 3H). LCMS R$_t$=1.295 min in 2 min chromatography, 30-90AB_E, MS ESI calcd. for C$_{28}$H$_{47}$O [M−H$_2$O+H]$^+$ 399, found 399.

Example 16. Synthesis of Compounds 37, 37-A, and 37-B

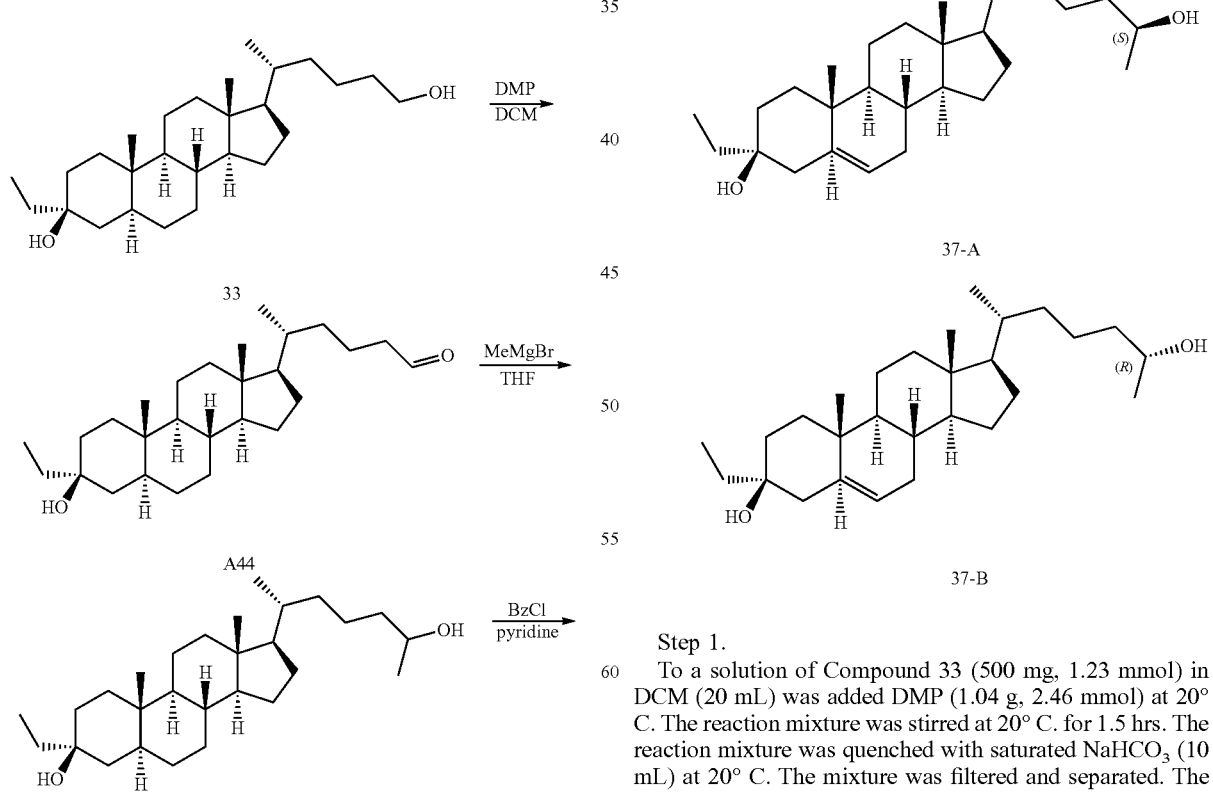

Step 1.

To a solution of Compound 33 (500 mg, 1.23 mmol) in DCM (20 mL) was added DMP (1.04 g, 2.46 mmol) at 20° C. The reaction mixture was stirred at 20° C. for 1.5 hrs. The reaction mixture was quenched with saturated NaHCO$_3$ (10 mL) at 20° C. The mixture was filtered and separated. The aqueous phase was extracted with DCM (20 mL). The combined organic phase was washed with saturated Na$_2$S$_2$O$_3$ (50 mL), brine (50 mL), dried over Na$_2$SO$_4$, filtered and concentrated to give A44 (500 mg, crude) as yellow solid. ¹H NMR (400 MHz, CDCl₃) δ 9.76 (s, 1H), 2.44-2.34 (m, 2H), 1.99-1.92 (m, 1H), 1.63-1.51 (m, 9H), 1.43-1.31 (m, 6H), 1.30-1.18 (m, 6H), 1.12-0.97 (m, 7H), 0.94-0.85 (m, 7H), 0.82 (s, 3H), 0.66-0.62 (m, 4H).

Step 2.

To a solution of A44 (500 mg, 1.24 mmol) in THF (20 mL) under N₂ was added MeMgBr (2.06 mL, 3.0 M, 6.19 mmol) at 0° C. in one portion. After stirring at 20° C. for 30 min, the mixture was quenched by 50 mL of saturated NH₄Cl and extracted with 50 mL of EtOAc. The separated organic phase was washed with 100 mL of brine, dried over Na₂SO₄, filtered and concentrated. The residue was purified by Combi-flash (EtOAc in PE, 0%-40%) to afford Compound 37 (350 mg, 67%) as an off white solid. 27 mg was delivered. ¹H NMR (400 MHz, CDCl₃) δ 3.85-3.72 (m, 1H), 1.99-1.91 (m, 1H), 1.86-1.74 (m, 1H), 1.69-1.59 (m, 3H), 1.56-1.50 (m, 3H), 1.50-1.27 (m, 11H), 1.26-1.16 (m, 8H), 1.14-0.95 (m, 7H), 0.93-0.79 (m, 11H), 0.67-0.59 (m, 4H). LCMS Rt=1.297 min in 2.0 min chromatography, 30-90 AB, MS ESI calcd. for C₂₈H₄₇ [M+H−2H₂O]⁺ 383, found 383.

Step 3.

To a solution of Compound 37 (300 mg, 0.716 mmol) in pyridine (10 mL) was added benzoyl chloride (501 mg, 3.57 mmol). The reaction was stirred at 20° C. for 2 h. The reaction was diluted with H₂O (50 mL), extracted with EtOAc (3×20 mL). The combined organic phase was washed with 1N HCl (100 mL), brine (100 mL), dried over Na₂SO₄, filtered and concentrated. The residue was purified by Combi-flash (0%-15% of EtOAc in PE) to afford A45 (270 mg, 72%) as clear oil. ¹H NMR (400 MHz, CDCl₃) δ 8.10-8.00 (m, 2H), 7.60-7.50 (m, 1H), 7.50-7.40 (m, 2H), 5.70-5.55 (m, 1H), 2.00-1.90 (m, 1H), 1.85-1.15 (m, 23H), 1.10-0.75 (m, 20H), 0.70-0.50 (m, 4H).

Step 4.

A45 (270 mg, 0.516 mmol) was purified by SFC (Column: AD(250 mm*30 mm, 5 um); Condition: 0.1% NH₃.H₂O EtOH; Gradient 35% B; Gradient Time(min):30; FlowRate(ml/min): 60) to afford A46 (peak 1, 90 mg) as white solid and A47 (peak 2, 100 mg) as white solid

A46:

¹H NMR (400 MHz, CDCl₃) δ 8.10-8.00 (m, 2H), 7.60-7.50 (m, 1H), 7.50-7.40 (m, 2H), 5.70-5.55 (m, 1H), 2.00-1.60 (m, 6H), 1.55-1.25 (m, 14H), 1.20-1.10 (m, 7H), 1.10-0.75 (m, 17H), 0.70-0.50 (m, 4H).

A47:

¹H NMR (400 MHz, CDCl₃) δ 8.10-8.00 (m, 2H), 7.60-7.50 (m, 1H), 7.50-7.40 (m, 2H), 5.70-5.55 (m, 1H), 2.00-1.60 (m, 7H), 1.55-1.20 (m, 20H), 1.20-0.80 (m, 17H), 0.70-0.50 (m, 4H).

Step 5.

To a solution of A46; (90 mg, 0.17 mmol) ill THF (5 mL) was added MeOH (2 mL) and a solution of LiOH.H₂O (72 mg, 1.72 mmol) at 25° C. The mixture was stirred at 25° C. for 17 hours. Water (5 mL) was added. The mixture was extracted with EtOAc (2×8 mL), washed with brine (2×10 mL), dried over Na₂SO₄, filtered, concentrated in vacuum to give a crude product, which was purified by flash-column (0-30% of EtOAc in PE, 50 mins) to give Compound 37-A (28 mg, 39%) as a white solid. ¹H NMR (400 MHz, CDCl₃) δ 3.90-3.70 (m, 1H), 2.00-1.60 (m, 5H), 1.55-1.40 (m, 5H), 1.35-1.20 (m, 17H), 1.20-0.80 (m, 18H), 0.70-0.50 (m, 4H). HPLC R_f=6.82 min in 8 min chromatography, 30-90_AB_1.2 ml_E, MS MS ESI calcd. For C₂₈H₄₇ [M+H−2H₂O]+383, found 383.

Step 6.

To a solution of A47 (100 mg, 0.19 mmol) in THF (5 mL) was added MeOH (2 mL) and a solution of LiOH.H₂O (80 mg, 1.91 mmol) at 25° C. The mixture was stirred at 25° C. for 17 hours. Water (5 mL) was added. The mixture was extracted with EtOAc (2×8 mL), washed with brine (2×10 mL), dried over Na₂SO₄, filtered, concentrated in vacuum to give a crude product, which was purified by flash-column (0-30% of EtOAc in PE, 50 mins) to give Compound 37-B (57 mg, 71%) as a white solid. ¹H NMR (400 MHz, CDCl₃) δ 3.90-3.70 (m, 1H), 2.00-1.60 (m, 7H), 1.55-1.30 (m, 11H), 1.25-1.15 (m, 9H), 1.10-0.75 (m, 18H), 0.70-0.50 (m, 4H). HPLC R_f=6.78 min in 8 min chromatography, 30-90_AB_1.2 ml_E, MS MS ESI calcd. For C₂₈H₄₇ [M+H−2H₂O]+383, found 383.

Example 17. Synthesis of Compounds 38, 39 and 40

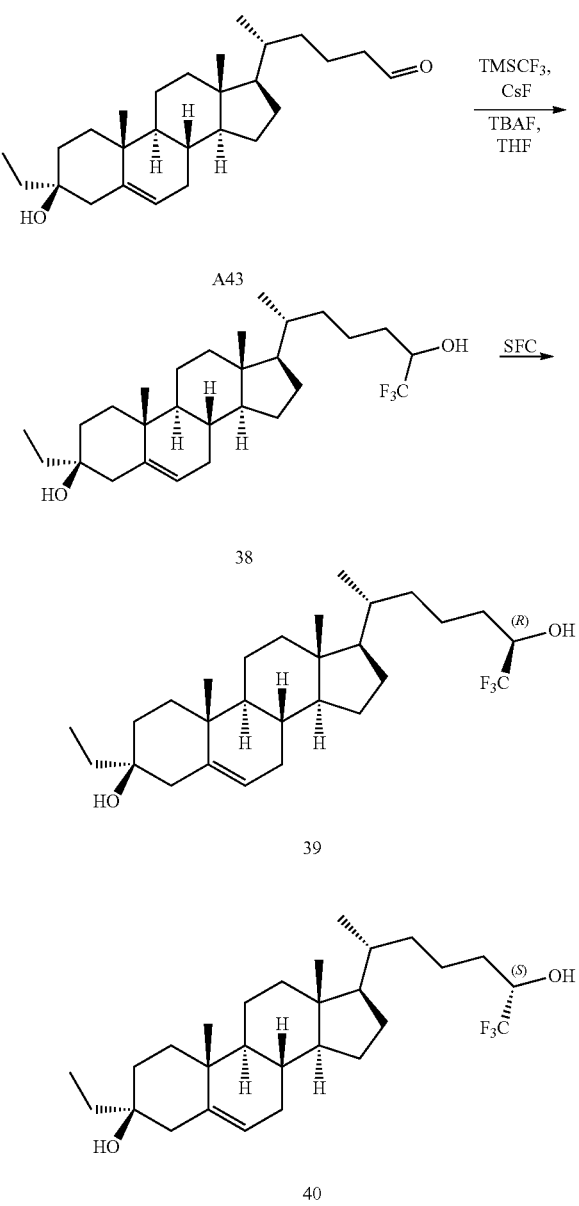

Step 1.

To a solution of A43 (1 g, crude) and CsF (200 mg, 1.31 mmol) in THF (15 mL) was added TMSCF₃ (1.76 g, 12.4 mmol) at 0° C. under nitrogen. The mixture was stirred at 20° C. for 1 h. TBAF (15 mL, 1M in THF) was added. The mixture was stirred at 20° C. for another 16 hours. The mixture was concentrated to 10 mL of the mixture in vacuum and DCM (30 mL) was added. The mixture was washed with water (3×50 mL), brine (2×50 mL), dried over Na₂SO₄, filtered and concentrated in vacuum to give a crude product, which was purified by flash column (0-25% of EtOAc in PE, 80 mins) to give Compound 38 (400 mg, crude) as an off white solid.

Compound 38 (400 mg, crude) was triturated with CH₃CN (30 mL) at 80° C. to give Compound 38 (310 mg) as an off white solid.

¹H NMR (400 MHz, CDCl₃) δ 5.32-5.25 (m, 1H), 3.95-3.85 (m, 1H), 2.40-2.30 (m, 1H), 2.10-1.60 (m, 10H), 1.55-1.30 (m, 9H), 1.25-0.90 (m, 17H), 0.85 (t, J=7.6 Hz, 3H), 0.67 (s, 3H). LCMS R$_f$=1.308 min in 2 min chromatography, 30-90AB_E, MS ESI calcd. for C₂₈H₄₄F₃O [M−H₂O+H]⁺ 453, found 453.

Step 2.

Compound 38 (300 mg) was purified by SFC (Column: AD (250 mm*30 mm, 5 um; Condition:0.1% NH₃H₂O IPA, 35% B; FlowRate(ml/min): 60;) to give Compound 39 (68 mg, 23%) and Compound 40 (39 mg, 13%) as an off white solid.

Compound 39:

¹H NMR (400 MHz, CDCl₃) δ 5.32-5.25 (m, 1H), 3.95-3.85 (m, 1H), 2.40-2.30 (m, 1H), 2.10-1.60 (m, 10H), 1.55-1.30 (m, 10H), 1.25-0.90 (m, 16H), 0.85 (t, J=7.6 Hz, 3H), 0.68 (s, 3H). LCMS R$_f$=1.307 min in 2 min chromatography, 30-90AB_E, MS ESI calcd. for C₂₈H₄₄F₃O [M−H₂O+H]⁺ 453, found 453.

Compound 40:

¹H NMR (400 MHz, CDCl₃) δ 5.32-5.25 (m, 1H), 3.95-3.85 (m, 1H), 2.40-2.30 (m, 1H), 2.10-1.60 (m, 10H), 1.55-1.25 (m, 13H), 1.20-0.90 (m, 13H), 0.85 (t, J=7.2 Hz, 3H), 0.68 (s, 3H). LCMS R$_f$=1.302 min in 2 min chromatography, 30-90AB_E, MS ESI calcd. for C₂₈H₄₄F₃O [M−H₂O+H]⁺ 453, found 453.

Example 18. Synthesis of Compound 41

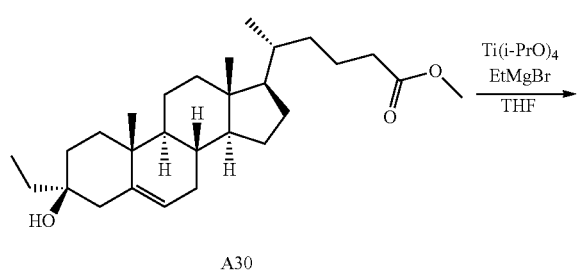

To a suspension of A30 (100 mg, 0.232 mmol) and Ti(i-PrO)₄ (65.9 mg, 0.232 mmol) in THF (10 mL) under N₂ was added EtMgBr (0.27 mL, 0.812 mmol) at 20° C. dropwise. After stirring at 20° C. for 1 h, the mixture was quenched by 0.4 mL of saturated NH₄Cl. The mixture was filtered. The filtrate was concentrated. The residue was purified by Combi-flash (EtOAc in PE, 0%-30%) to afford Compound 41 (42 mg, 42%) as an off white solid. ¹H NMR (400 MHz, CDCl₃) δ 5.33-5.23 (m, 1H), 2.41-2.31 (m, 1H), 2.07-1.91 (m, 3H), 1.88-1.67 (m, 3H), 1.66-1.57 (m, 3H), 1.53-1.35 (m, 11H), 1.33-1.00 (m, 11H), 0.99-0.81 (m, 8H), 0.76-0.71 (m, 2H), 0.67 (s, 3H), 0.47-0.41 (m, 2H). LCMS Rt=1.309 min in 2.0 min chromatography, 30-90 AB, MS ESI calcd. for C₂₉H₄₇O [M+H−H₂O]⁺ 411, found 411.

Example 19. Synthesis of Compound 42

To a suspension of A41 (150 mg, 0.346 mmol) and Ti(i-PrO)₄ (98.3 mg, 0.346 mmol) in THF (10 mL) under N₂ was added EtMgBr (0.4 mL, 1.21 mmol) at 20° C. dropwise. After stirring at 20° C. for 1 h, the mixture was quenched by 0.4 mL of saturated NH₄Cl. The mixture was filtered. The filtrate was concentrated. The residue was purified by Combi-flash (EtOAc in PE, 0%-30%) to afford Compound 42 (78 mg, 52%) as an off white solid. ¹H NMR (400 MHz, CDCl₃) δ 2.00-1.92 (m, 1H), 1.86-1.71 (m, 2H), 1.69-1.56 (m, 6H), 1.53-1.33 (m, 10H), 1.29-1.16 (m, 5H), 1.14-0.96 (m, 7H), 0.94-0.81 (m, 11H), 0.75-0.71 (m, 2H), 0.67-0.60 (m, 4H), 0.46-0.42 (m, 2H). LCMS Rt=1.343 min in 2.0 min chromatography, 30-90 AB, MS ESI calcd. for C$_{29}$H$_{47}$ [M+H−2H$_2$O]$^+$ 395, found 395.

Example 20. Synthesis of Compounds 43, 43-A, and 43-B

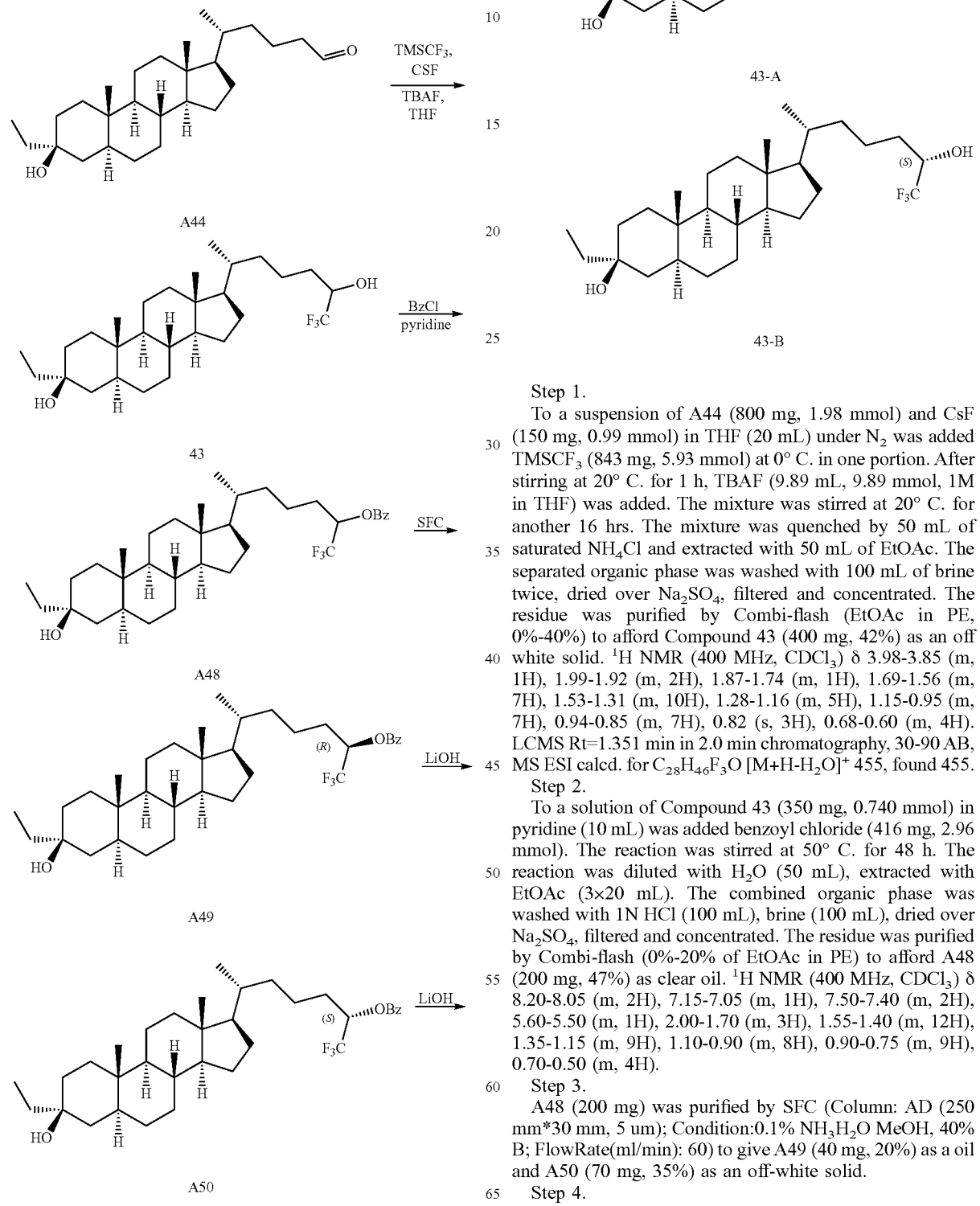

Step 1.

To a suspension of A44 (800 mg, 1.98 mmol) and CsF (150 mg, 0.99 mmol) in THF (20 mL) under N$_2$ was added TMSCF$_3$ (843 mg, 5.93 mmol) at 0° C. in one portion. After stirring at 20° C. for 1 h, TBAF (9.89 mL, 9.89 mmol, 1M in THF) was added. The mixture was stirred at 20° C. for another 16 hrs. The mixture was quenched by 50 mL of saturated NH$_4$Cl and extracted with 50 mL of EtOAc. The separated organic phase was washed with 100 mL of brine twice, dried over Na$_2$SO$_4$, filtered and concentrated. The residue was purified by Combi-flash (EtOAc in PE, 0%-40%) to afford Compound 43 (400 mg, 42%) as an off white solid. $^1$H NMR (400 MHz, CDCl$_3$) δ 3.98-3.85 (m, 1H), 1.99-1.92 (m, 2H), 1.87-1.74 (m, 1H), 1.69-1.56 (m, 7H), 1.53-1.31 (m, 10H), 1.28-1.16 (m, 5H), 1.15-0.95 (m, 7H), 0.94-0.85 (m, 7H), 0.82 (s, 3H), 0.68-0.60 (m, 4H). LCMS Rt=1.351 min in 2.0 min chromatography, 30-90 AB, MS ESI calcd. for C$_{28}$H$_{46}$F$_3$O [M+H-H$_2$O]$^+$ 455, found 455.

Step 2.

To a solution of Compound 43 (350 mg, 0.740 mmol) in pyridine (10 mL) was added benzoyl chloride (416 mg, 2.96 mmol). The reaction was stirred at 50° C. for 48 h. The reaction was diluted with H$_2$O (50 mL), extracted with EtOAc (3×20 mL). The combined organic phase was washed with 1N HCl (100 mL), brine (100 mL), dried over Na$_2$SO$_4$, filtered and concentrated. The residue was purified by Combi-flash (0%-20% of EtOAc in PE) to afford A48 (200 mg, 47%) as clear oil. $^1$H NMR (400 MHz, CDCl$_3$) δ 8.20-8.05 (m, 2H), 7.15-7.05 (m, 1H), 7.50-7.40 (m, 2H), 5.60-5.50 (m, 1H), 2.00-1.70 (m, 3H), 1.55-1.40 (m, 12H), 1.35-1.15 (m, 9H), 1.10-0.90 (m, 8H), 0.90-0.75 (m, 9H), 0.70-0.50 (m, 4H).

Step 3.

A48 (200 mg) was purified by SFC (Column: AD (250 mm*30 mm, 5 um); Condition:0.1% NH$_3$H$_2$O MeOH, 40% B; FlowRate(ml/min): 60) to give A49 (40 mg, 20%) as a oil and A50 (70 mg, 35%) as an off-white solid.

Step 4.

To a solution of A49 (40 mg) in THF (2 mL) was added MeOH (1 mL) and a solution of LiOH.H$_2$O (16.6 mg, 0.69 mmol) in $H_2O$ (1 mL) at 25° C. The mixture was stirred at 25° C. for 17 hours. The mixture as extracted with EtOAc (2×5 mL), washed with brine (2×10 mL), dried over $Na_2SO_4$, filtered, purified by flash column (0-30% of EtOAc in PE) to give 43-A (20 mg, impure) as an off-white solid, which was triturated with $CH_3CN$ (2 mL) at 25° C. then filter cake was dissolved in $CH_3CN$ (20 mL) at 80° C. The solution was concentrated in vacuum to give 43-A (6 mg, 31%) as an off-white solid. $^1H$ NMR (400 MHz, $CDCl_3$) δ 4.00-3.85 (m, 1H), 2.10-1.75 (m, 3H), 1.70-1.60 (m, 5H), 1.55-1.20 (m, 16H), 1.15-0.75 (m, 18H), 0.70-0.55 (m, 4H). LCMS $R_f$=1.319 min in 2 min chromatography, 30-90AB_E, MS ESI calcd. For $C_{28}H_{46}F_3O$ $[M+H-H_2O]^+$ 455, found 455.

Step 5.

To a solution of A50 (70 rug) in THF (3 was added MeOH (2 mL) and a solution of $LiOH.H_2O$ (50.7 mg, 1.2 mmol) in $H_2O$ (2 nit) at 25° C. The mixture was stirred at 25° C. for 17 hours. The mixture as extracted with EA (2×6 mL), washed with brine (2×10 mL), dried over $Na_2SO_4$, filtered, purified by flash column (0-30% of EtOAc in PE, 1 h) to give 43-B (40 mg, impure) as oil, which was re-crystallized from 4 mL of $CH_3CN$ at 80° C. to give 43-B (23 mg, 58%) as an off-white solid. $^1H$ NMR (400 MHz, $CDCl_3$) δ 4.00-3.85 (m, 1H), 2.10-1.75 (m, 3H), 1.70-1.60 (m, 5H), 1.55-1.20 (m, 16H), 1.15-0.75 (m, 18H), 0.70-0.55 (m, 4H). LCMS $R_f$=1.315 min in 2 min chromatography, 30-90AB_E, MS ESI calcd. For $C_{28}H_{46}F_3O$ $[M+H-H_2O]^+$ 455, found 455.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative neuroactive steroids that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for the region between δ (ppm) of about 0.5 to about 4 ppm) will be understood to be an exemplary interpretation of the NMR spectrum (e.g., exemplary peak integratations) of a compound. Exemplary general method for preparative HPLC: Column: Waters RBridge prep 10 μm C18, 19*250 mm. Mobile phase: acetonitrile, water ($NH_4HCO_3$) (30 L water, 24 g $NH_4HCO_3$, 30 mL $NH_3.H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 μm at 45 C.

NMDA Potentiation

NMDA potentiation was assessed using either whole cell patch clamp of mammalian cells which expressed NMDA receptors.

Whole-Cell Patch Clamp of Mammalian Cells (Lonworks Barracuda (IWB)

The whole-cell patch-clamp technique was used to investigate the effects of compounds on GluNN1/GluN2A glutamate receptors expressed in mammalian cells. The results are shown on Table 1.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 μg/ml penicillin G sodium, 100 μg/ml streptomycin sulphate, 100 μg/ml Zeocin, 5 μg/ml blasticidin and 500 μg/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeScienses). The measurements were performed using Ion Works Barracuda platform following this procedure:

Electrophysiological Procedures:
a) Intracellular solution (mM): 50 mM CsCl, 90 mM CsF, 2 mM $MgCl_2$, 5 mM EGTA, 10 mM HEPES. Adjust to pH 7.2 with CsOH.
b) Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).
c) Holding potential: −70 mV, potential during agonist/PAM application: −40 mV.

Recording Procedure:
a) Extracellular buffer will be loaded into the PPC plate wells (11 μL per well). Cell suspension will be pipetted into the wells (9 μL per well) of the PPC planar electrode.
b) Whole-cell recording configuration will be established via patch perforation with membrane currents recorded by on-board patch clamp amplifiers.
c) Two recordings (scans) will be performed. First, during pre-application of test article alone (duration of pre-application—5 min) and second, during test articles and agonist ($EC_{20}$ L-glutamate and 30 μM glycine) co-application to detect positive modulatory effects of the test article.

Test Article Administration: The first pre-application will consist of the addition of 20 μL of 2× concentrated test article solution and, second, of 20 μL of 1× concentrated test article and agonist at 10 μL/s (2 second total application time).

TABLE 1

| Structure | GluN2A PCA IWB Ephys % potentiation at 3 μM |
|---|---|
| Compound 1 | B |
| Compound 2 | A |
| Compound 4 | A |
| Compound 5 | A |
| Compound 6 | B |
| Compound 7 | A |
| Compound 8 | A |
| Compound 9 | A |
| Compound 10 | B |
| Compound 11 | A |
| Compound 12 | A |
| Compound 13 | A |
| Compound 14 | B |
| Compound 15 | A |
| Compound 17 | A |
| Compound 18 | B |
| Compound 19 | B |
| Compound 22 | B |
| Compound 23 | A |
| Compound 24 | B |
| Compound 25 | A |
| Compound 26 | A |

For Table 1, "A" indicates 10 to 100%, and "B" indicates potentiation of >100%; and "ND" indicates not determinable or not determined.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of the formula:

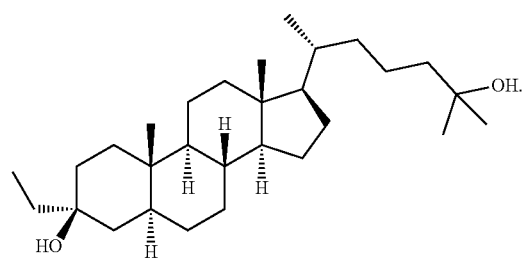

2. A pharmaceutical composition comprising a compound of the formula:

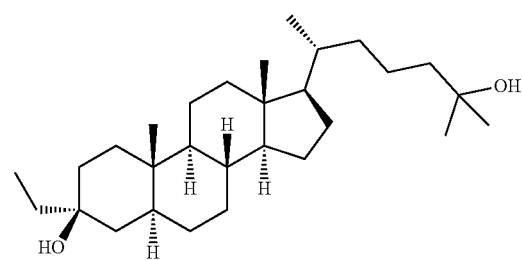

and a pharmaceutically acceptable excipient.

* * * * *